United States Patent
Mitani et al.

(12) 
(10) Patent No.: US 6,326,493 B1
(45) Date of Patent: *Dec. 4, 2001

(54) METALLOCENE COMPOUNDS, PROCESSES FOR THE PREPARATION THEREOF, CATALYST COMPONENTS FOR OLEFIN POLYMERIZATION, AND PROCESSES FOR THE PRODUCTION OF OLEFIN POLYMERS

(75) Inventors: Seiki Mitani, Kanagawa-ken; Masato Nakano; Jun Saito, both of Chiba-ken; Hiroshi Yamazaki, Saitama-ken; Keisuke Kimura, *deceased*, late of Chiba-ken, all of (JP), Toshihiro Kimura legal representitive

(73) Assignee: Chisso Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/449,638

(22) Filed: Nov. 30, 1999

Related U.S. Application Data

(63) Continuation-in-part of application No. 09/236,322, filed on Jan. 25, 1999, now Pat. No. 6,169,051.
(51) Int. Cl.[7] .............................. C07F 17/00; B01J 31/00; C08F 4/02
(52) U.S. Cl. .............................. 546/4; 548/103; 548/403; 549/3; 549/206; 526/126; 526/160; 526/357; 526/943; 556/11; 556/12; 556/53; 502/103; 502/117; 502/120
(58) Field of Search .................................. 502/103, 117, 502/120; 526/126, 160, 357, 943; 556/11, 12, 53; 546/4; 548/103, 403; 549/3, 206; 987/2

(56) References Cited

U.S. PATENT DOCUMENTS 6,169,051 * 1/2001 Mitani et al. ........................ 502/103

FOREIGN PATENT DOCUMENTS 7-258282   10/1995   (JP) .
8-183814   7/1996    (JP) .

OTHER PUBLICATIONS

"Elastomeric Polypropylene from Unbridge 2–Arylindenyl Zirconocenes: Modeling Polymerization Behavior Using ansa–Metallocene Analogues" by Petoff et al., J. Am. Chem. Soc, 1998, vol. 120, pp. 11316–11322.

"Polymerization Catalysts with Cyclopentadienyl Ligands Ring–Fused to Pyrrole and Thiophene Heterocycles" by Ewen et al., J. Am. Chem. Soc., 1998, vol. 120, pp. 10786–10787.

* cited by examiner

*Primary Examiner*—Porfirio Nazario-Gonzalez
(74) *Attorney, Agent, or Firm*—McDermott, Will & Emery

(57) ABSTRACT

A metallocene compound is provided wherein to a transition metal compound is bonded a multidentate compound wherein a substituted cycloalkadienyl ring $CA^1$ having therein a heteroaromatic group Ra containing an oxygen, sulfur or nitrogen atom on a cycloalkadienyl ring, preferably the five-membered ring thereof, and an unsubstituted or substituted cycloalkadienyl group $CA^2$ or $—(R^1)N—$, $—O—$, $—S—$ or $—(R^1)P—$, preferably $CA^2$, more preferably a substituted cycloalkadienyl group identical with $CA^1$ are bonded through a divalent linking group. The metallocene compound is suitable as a principal ingredient of a catalyst for the polymerization of olefins, particularly achieving a very high effect in making the molecular weight of a polypropylene higher.

30 Claims, 3 Drawing Sheets

METALLOCENE COMPOUNDS, PROCESSES FOR THE PREPARATION THEREOF, CATALYST COMPONENTS FOR OLEFIN POLYMERIZATION, AND PROCESSES FOR THE PRODUCTION OF OLEFIN POLYMERS

This application claims priority from and is a continuation-in-part application of U.S. patent application Ser. No. 09/236,322, filed Jan. 25, 1999, now U.S. Pat. No. 6,169,051, which is incorporated herein by reference.

TECHNICAL FIELD

This invention relates to new metallocene compounds useful as a catalyst component for olefin polymerization. More particularly, the invention relates to metallocene compounds wherein a multidentate compound containing a cycloalkadienyl ring substituted by a heteroaromatic group is coordinated to a Group VIB transition metal atom of the Periodic Table, and also to the processes for the preparation thereof.

Further, the invention relates to catalysts for olefin polymerization containing said metallocene compounds and processes for the production of olefin polymers using them.

BACKGROUND ART

As a catalyst substituted for Ziegler-Natta catalysts which have been used in the polymerization of olefins, a part of the metallocene compounds is being used which consist of a complex compound wherein a multidentate compound containing a i-electron donor such as unsubstituted or substituted cycloalkadienyl groups is coordinated to a transition metal atom, the unsubstituted or substituted cycloalkadienyl groups including e.g., unsubstituted or substituted cyclopentadienyl groups, unsubstituted or substituted indenyl groups, unsubstituted or substituted tetrahydroindenyl groups, and unsubstituted or substituted fluorenyl groups.

In recent years, various metallocene compounds have been proposed having higher olefin polymerization activity per mole of a transition metal atom. It is known that the polymers of α-olefin having 3 or more carbon atoms, in particular, propylene polymers, prepared by using a chiral metallocene compound have high stereoregularity, the chiral metallocene compound being the compound wherein a multidentate compound having two substituted cycloalkadienyl groups bonded with a divalent linking group is coordinated to a transition metal atom (J. Am. Chem. Soc. 1998, 120, 11316–11322).

Further, the development of metallocene compounds with high olefin polymerization activity has continued. Various metallocene compounds have been proposed wherein a heteroatom is introduced into the substituent or cycloalkadiene ring in the substituted cycloalkadienyl group.

For instance, Japanese Patent Kokai 7-258282 discloses metallocene compounds wherein the 2-position of the indenyl group is substituted by a saturated group containing a heteroatom such as nitrogen, phosphorus, arsenic, antimony, bismuth or the like, specifically those wherein 2-pyrrolidino-1-indene is linked through a divalent linking group and coordinated to a transition metal atom.

Japanese Patent Kokai 8-183814 discloses chiral metallocene compounds wherein the 4-position of the indenyl group is substituted by unsubstituted or substituted 1-pyrrolyl group, 1-indolyl group or the like, specifically those wherein 4-(1-indolyl)-2-methylindene is linked through a divalent linking group and coordinated to a transition metal atom.

J. Am. Chem. Soc. 1998, 120, 10786–10787 discloses metallocene compounds wherein a heteroatom-containing cycloalkadiene having a thiophene ring or a pyrrol ring condensed to a cyclopentadiene ring is linked through a divalent linking group and coordinated to a transition metal atom.

DISCLOSURE OF THE INVENTION

As mentioned above, there are various proposals for introducing a heteroatom into a π-electron donor. Except for the compounds disclosed in Japanese Patent Kokai 8-183814, however, the metallocene compounds are not known wherein the substituted cycloalkadienyl group-containing compounds having a heteroaromatic group containing an oxygen atom, a sulfur atom or a nitrogen atom on a cycloalkadiene ring, particularly on the 5-membered ring thereof are coordinated to a transition metal atom.

The present invention provides a metallocene compound represented by the following formula (1)

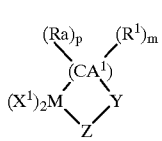

(1)

wherein $CA^1$ represents a cycloalkadienyl group selected from the group consisting of a cyclopentadienyl group, an indenyl group, a tetrahydroindenyl group, a benzoindenyl group, a fluorenyl group and an azulenyl group;

each $R^1$ represents independently a halogen atom, a hydrocarbon group of 1–20 carbons, a halogenated hydrocarbon group wherein a part or all of the hydrogen atoms in the hydrocarbon group are substituted by a halogen atom, a silyl group substituted by said hydrocarbon group or said halogenated hydrocarbon group, an amino group substituted by said hydrocarbon group or a monocyclic or polycyclic amino group;

each Ra represents independently a monocyclic or polycyclic heteroaromatic group containing a heteroatom selected from the group consisting of an oxygen atom, a sulfur atom and a nitrogen atom in a 5- or 6-membered ring, the heteroaromatic group being optionally substituted by $R^1$ as defined above;

p is an integer of 1–8;

m is 0 or an integer of 1–8;

Z represents a linking group selected from the group consisting of $(CA^2)(R^1)_m(Ra)_p$, $(CA^2)(Ra)_q(R^1)_n$, —O—, —S—, —$NR^1$— and —$PR^1$— wherein $CA^2$ represents an unsubstituted or substituted cycloalkadienyl group; Ra and $R^1$ have the same meanings as defined above, Ra may be identical with or different from said Ra on $CA^1$ and $R^1$ may be identical with or different from said $R^1$ on $CA^1$; and q and n are each independently 0 or an integer of 1–8;

Y represents a divalent linking group selected from the group consisting of —$C(R^2)_2$—, —$C_2(R^2)_4$—, —$C_6(R^2)_{10}$—, —$C_6(R^2)_4$—, —$Si(R^2)_2$—, —$Ge(R^2)_2$— and —$Sn(R^2)_2$— wherein each $R^2$ represents independently a hydrogen atom, a halogen atom, a hydrocarbon group of 1–20 carbons, a halogenated hydrocarbon group wherein a part or all of the hydrogen atoms in the hydrocarbon group are substituted by a halogen atom or a silyl group substituted by said hydrocarbon group or said halogenated hydrocarbon group;

M represents a transition metal atom selected from the group consisting of Ti, Zr and Hf; and each $X^1$ represents independently a halogen atom, a hydrocarbon group of 1–20 carbons, a halogenated hydrocarbon group wherein a part or all of the hydrogen atoms in the hydrocarbon group are substituted by a halogen atom or a silyl group substituted by said hydrocarbon group or said halogenated hydrocarbon group.

The present invention also provides a process for the preparation of said metallocene compound.

Further, the invention provides a catalyst for olefin polymerization comprising said metallocene compound and an aluminoxane. The invention further provides a process for the production of an olefin polymer wherein an olefin is polymerized in the presence of said olefin polymerization catalyst and in the presence or absence of an organic aluminum compound.

DETAILED DESCRIPTION

Figure 1:
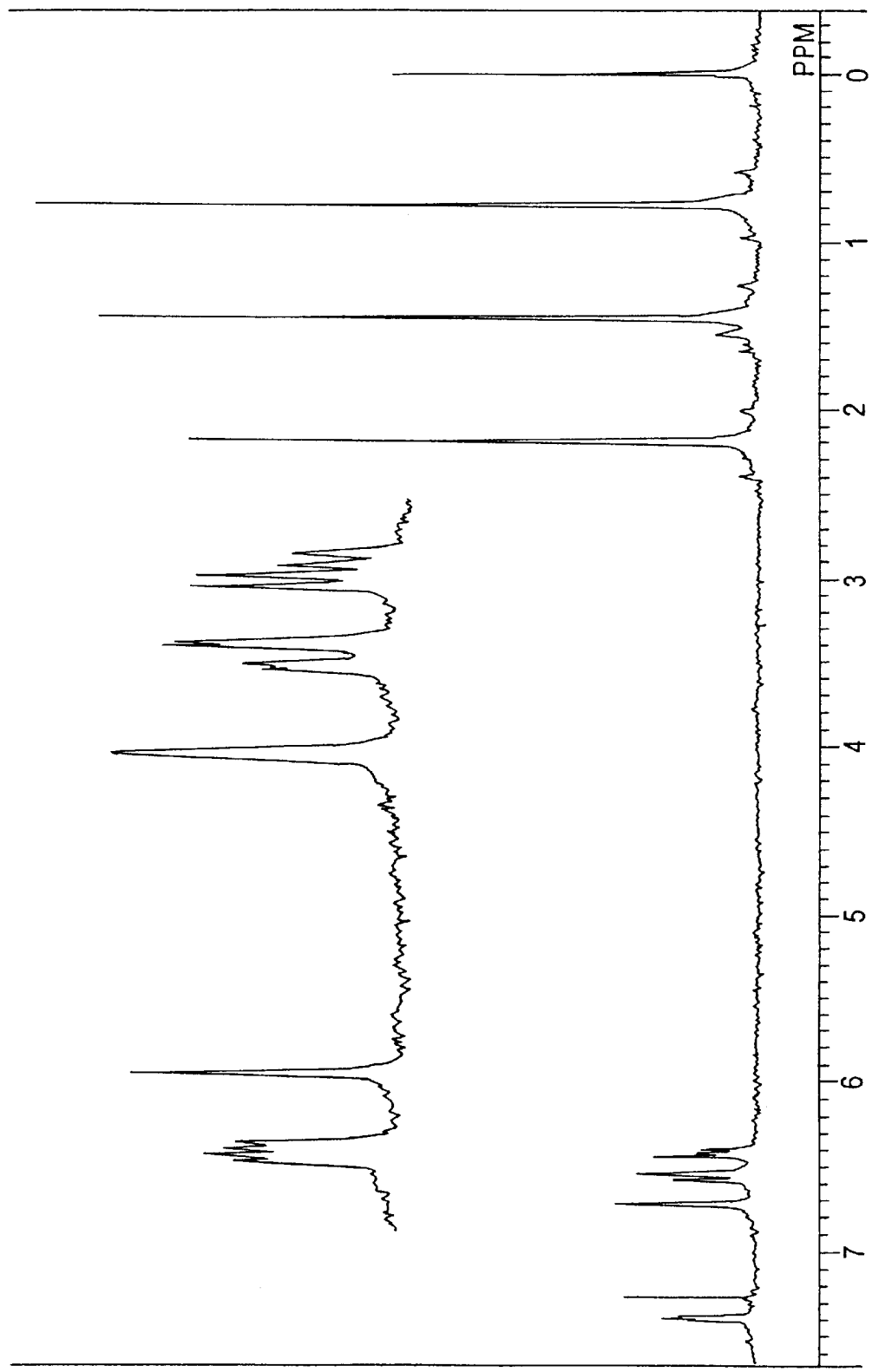
FIG. 1 is $^1$H-NMR chart determined in deuteriochloroform for compound No. 95 synthesized in Example 3, rac-dimethylsilylenebis[2-(2-furyl)-4,5-dimethylcyclopentadienyl]zirconium dichloride.

The metallocene compounds of the present invention represented by the formula (1) are largely classified into the compounds having a fundamental structure wherein Z is $(Ra)_p(R^1)_m(CA^1)$ or $(Ra)_q(R^1)_n(CA^2)$ and the compounds having a fundamental structure wherein Z is selected from —O—, —S—, —NR$^1$— and —PR$^1$—.

The cycloalkadienyl group CA includes a cyclopentadienyl group, an indenyl group, a tetrahydroindenyl group, a benzoindenyl group, a fluorenyl group or an azulenyl group.

In the present invention, one or more hydrogens in the cycloalkadienyl group CA$^1$ are substituted by the heteroaromatic group Ra which may be substituted by the substituent R$^1$ as defined above.

The heteroaromatic group Ra which substitutes a hydrogen atom on CA$^1$ and CA$^2$ is the groups containing as a heteroatom an oxygen atom, a sulfur atom or a nitrogen atom in the 5- or 6-membered ring. Preferable heteroaromatic groups include furyl, thienyl, pyridyl, benzofuryl, benzothienyl, quinolyl, pyrrolyl or indolyl having a bond at other positions than the 1-position, and those groups substituted by the substituent R$^1$ as recited later. In case of the heteroaromatic group being substituted by the substituent R$^1$, for example, furyl is preferably substituted at the 4- or 5-position, most preferably at the 5-position. Where CA$^1$ and CA$^2$ are respectively substituted by one or more Ra, each Ra may be identical or different.

Preferably, the heteroaromatic group Ra substitutes a hydrogen atom on the 5-membered ring in the cycloalkadienyl group CA$^1$. More preferably, the group Ra substitutes a hydrogen atom at the 2- and/or 3-position of the cyclopentadienyl group. Preferable substituted cycloalkadienyl group CA$^1$ includes a substituted cyclopentadienyl group, a substituted indenyl group, a substituted tetrahydroindenyl and a substituted benzoindenyl group, more preferably a substituted cyclopentadienyl group and a substituted indenyl group.

p indicates the number of substitution by the heteroaromatic group Ra on the cycloalkadienyl group CA$^1$, and is an integer of 1 to 8, preferably 1 to 4, more preferably 1 or 2.

CA$^2$ in $(Ra)_q(R^1)_n(CA^2)$ selected for the group Z is an unsubstituted or substituted cycloalkadienyl group. The cycloalkadienyl group CA$^2$ includes a cyclopentadienyl group, an indenyl group, a tetrahydroindenyl group, a benzoindenyl group and a fluorenyl group. The substituted cycloalkadienyl groups CA$^2$ are those wherein one or more hydrogen atoms on the cycloalkadienyl group are substituted by either or both of the heteroaromatic group Ra and the substituent R$^1$.

For the case where CA$^2$ is the cycloalkadienyl group substituted by the heteroaromatic group Ra, it is preferable that the heteroaromatic group Ra substitutes a hydrogen atom on the 5-membered ring in the cycloalkadienyl group.

q indicates the number of substitution by the heteroaromatic group Ra on CA$^2$, and is 0 or an integer of 1 to 8, preferably 1 to 4, more preferably 1 or 2.

The substituents R$^1$ on CA$^1$ and CA$^2$ include a halogen atom, e.g., fluorine, chlorine, bromine or iodine; a hydrocarbon group of 1–20 carbons, e.g., an alkyl group of 1–20 carbons, an aryl group of 6–20 carbons, an aralkyl group of 7–20 carbons, an alkoxy group of 1–20 carbons, an aryloxy group of 6–20 carbons or an aralkyloxy group of 7–20 carbons; a halogenated hydrocarbon group wherein a part or all of the hydrogen atoms in said hydrocarbon group are substituted by said halogen atom; a silyl group trisubstituted by said hydrocarbon group and/or said halogenated hydrocarbon group; an amino group di-substituted by said hydrocarbon group; and a monocyclic or polycyclic amino group. Where CA$^1$ and CA$^2$ are respectively substituted by one or more R$^1$, each R$^1$ may be identical or different.

m and n indicate the number of substitution by R$^1$ on CA$^1$ and CA$^2$, and are respectively 0 or an integer of 1 to 8, preferably 1 to 4, more preferably 1 or 2.

The alkyl group of 1–20 carbons includes, for example, a straight- or branched-chain alkyl group, e.g., methyl, ethyl, propyl, i-propyl, n-butyl, i-butyl, tert-butyl, sec-butyl, pentyl, hexyl, heptyl, octyl, 2-ethylhexyl, nonyl, decyl, dodecyl or octadecyl; and a cyclic alkyl group which may be substituted by said chain alkyl group, e.g., cyclopropyl, cycloheptyl or cyclohexyl.

The aryl group of 6–20 carbons may be unsubstituted or substituted by said alkyl group, which includes, for example, phenyl, naphthyl, anthryl, tolyl, xylyl and trimethylphenyl. The aralkyl group of 7–20 carbons may be unsubstituted or substituted by said alkyl group, which includes, for example, benzyl, naphthylmethyl, anthrylmethyl, (methylphenyl)methyl, (dimethylphenyl)methyl, (trimethylphenyl)methyl, (ethylphenyl)methyl, (propylphenyl)methyl and (butylphenyl)methyl.

The alkoxy group of 1–20 carbons includes chain and cyclic alkoxy groups wherein the alkyl moiety is said alkyl group, e.g., methoxy, ethoxy, propoxy, isopropoxy, butoxy, t-butoxy, hexyloxy or cyclohexyloxy. The aryloxy group of 6–20 carbons includes substituted or unsubstituted aryloxy groups wherein the aryl moiety is said aryl group, e.g., phenoxy, naphthyloxy or anthryloxy. The aralkyloxy group of 7–20 carbons includes aralkyloxy groups wherein the aralkyl moiety is said aralkyl group, e.g., benzyloxy.

The halogenated hydrocarbon groups are those wherein a part or all of the hydrogen atoms in said hydrocarbon groups are substituted by said halogen atom, which include halogenated alkyl groups, halogenated aryl groups, halogenated aralkyl groups, halogenated alkoxy groups, halogenated aryloxy groups and halogenated aralkyloxy groups, e.g., monochloromethyl, dichloromethyl, trichloromethyl, perfluoroethyl, monochlorophenyl, difluorophenyl or monochlorobenzyl.

The substituted silyl groups are those substituted by said hydrocarbon group and/or said halogenated hydrocarbon group, e.g., trimethylsilyl, triethylsilyl, triphenylsilyl, trimethoxysilyl, tribenzylsilyl, triethoxysilyl, dimethylphenoxysilyl, dimethylvinylsilyl and allyldimethylsilyl.

The substituted amino groups are those substituted by said hydrocarbon group, e.g., dimethylamino, diethylamino and methylethylamino. The monocyclic or polycyclic amino groups may be saturated or unsaturated, which include, e.g., 1-pyrrolidyl, 1-pyrrolyl and 1-indolyl.

The divalent linking group Y includes $-C(R^2)_2-$, e.g., methylene; $-C_2(R^2)_4-$, e.g., ethylene; $-C_6(R^2)_{10}-$, e.g., cyclohexylene; $-C_6(R^2)_4-$, e.g., phenylene; $-Si(R^2)_2-$, e.g., silylene; $-Ge(R^2)_2-$, e.g., germanylene; and $-Sn(R^2)_2-$, e.g., stanylene wherein $R^2$ is as defined above.

Preferred linking group Y is $-C(R^2)_2-$, e.g., methylene, dichloromethylene, dimethylmethylene and diphenylmethylene; $-C_2(R^2)_4-$, e.g., ethylene, tetrachloroethylene, tetramethylethylene, tetraethylethylene and dimethyldiphenylethylene; $-Si(R^2)_2-$, e.g., dichlorosilylene, dimethylsilylene and diethylsilylene; and $-Ge(R^2)_2-$, e.g., dichlorogermanylene and dimethylgermanylene.

The transition metal atom M is selected from the group consisting of Ti, Zr and Hf.

The substituent $X^1$ for M is a hydrogen atom, a halogen atom, a similar hydrocarbon or halogenated hydrocarbon group as defined above for the substituent $R^1$, preferably a halogen atom, more preferably chlorine.

The metallocene compound of formula (1) wherein Z is $(CA^2)(R^1)_n(Ra)_q$ can be represented by the following formula (2)

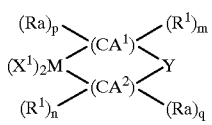

(2)

wherein each symbol has the meaning as defined above.

$CA^1$ and $CA^2$ in the formula may be identical or different. In addition to the identity of $CA^1$ with $CA^2$, the compound of the following formula (2A) wherein Z is $(Ra)_p(R^1)_m(CA^1)$ in formula (1) shows high olefin polymerization activity excellent as the below-mentioned catalyst for olefin polymerization.

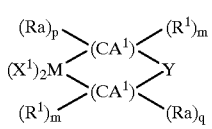

(2A)

wherein each symbol has the meaning as defined above. This compound (2A) includes a racemic form consisting of a stereostructurally unsymmetrical compound with respect to the plane containing M and its enantiomer, a mesa form consisting of a stereostructurally symmetrical compound with respect to the plane containing M, and the mixture thereof.

The metallocene compounds wherein concrete combination of $CA^1$ and $CA^2$ is specified are represented by the following formulas (2a) to (2g).

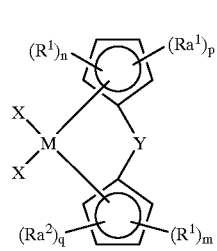

(2a)

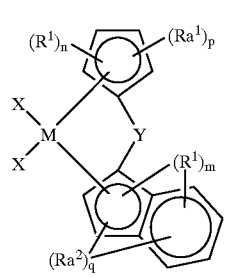

(2b)

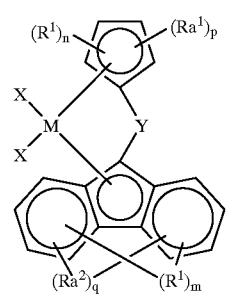

(2c)

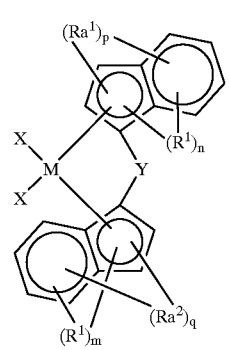

(2d)

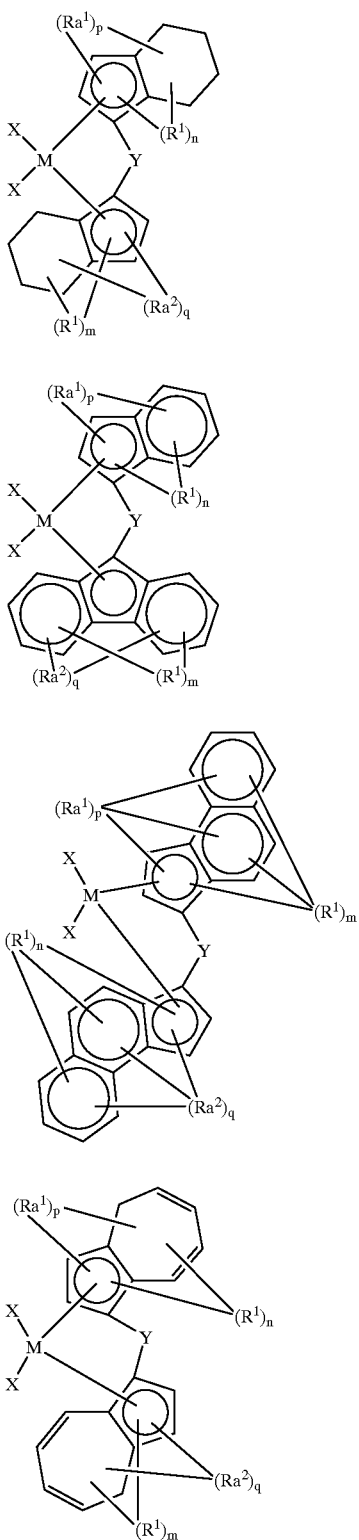

(2e)

(2f)

(2g)

(2h)

Further, concrete examples of metallocene compounds represented by formula (2a) are shown in the attached Tables 2–9 and 23, concrete examples of metallocene compounds represented by formula (2d) are shown in the attached Tables 10–13 and 22, concrete examples of metallocene compounds represented by formula (2e) are shown in the attached Tables 14–17, concrete examples of metallocene compounds represented by formula (2g) are shown in the attached Tables 18, 19 and 24, and concrete examples of metallocene compounds represented by formula (2h) are shown in the attached Table 25, by way of indicating concrete groups corresponding to each symbol in each formula and without distinction of the racemic and meso forms.

For instance, the compound denoted by Number 1 in Table 2 represents ethylenebis[2-(2-furyl)-cyclopentadienyl][2'-(2-furyl)-cyclopentadienyl]zirconium dichloride, ethylenebis[2-(2-furyl)-cyclopentadienyl][5'-(2-furyl)-cyclopentadienyl]zirconium dichloride and the mixture thereof. For the compounds wherein the substituent $R^1$ is present on both $CA^1$ and $CA^2$, they represent the compounds having the relationship of the racemic form and the meso form from a substitution position of each substituent $R^1$ on $CA^1$ and $CA^2$, and the mixture thereof.

The abbreviations used in Tables 2–25 are as follows:

| | |
|---|---|
| Fu: furyl, | MeFu: methyl furyl, |
| Thie: thienyl, | Py: pyridyl, |
| BzFu: benzofuryl, | 1-MePyr: 1-methylpyrrolyl, |
| Me: methyl, | Et: ethyl, |
| i-Pr: isopropyl, | t-Bu: tert-butyl, |
| Ph: phenyl, | Np: naphthyl, |
| Tol: toluyl, | Bzl: benzyl, |
| OMe: methoxy, | OPh: phenoxy, |
| OBzl: benzyloxy, | TMS: trimethylsilyl, |
| Pyr: pyrrolyl, | Indo: indolyl, |
| Vi: vinyl | |

The combinations of $CA^1$ and $CA^2$ may be, in addition to the above, those of a substituted cyclopentadienyl group and a substituted tetrahydroindenyl group, a substituted cyclopentadienyl group and a substituted benzoindenyl group, a substituted indenyl group and a substituted tetrahydroindenyl group, a substituted indenyl group and a substituted benzoindenyl group, a substituted tetrahydroindenyl group and a substituted benzoindenyl group, a substituted tetrahydroindenyl group and a substituted fluorenyl group, and a substituted benzoindenyl group and a substituted fluorenyl group.

The metallocene compounds of formula (1) wherein Z is —($R^1$)N—, —O—, —S— and —($R^1$)P—, respectively are represented by the following formulas (3a)–(3d). Concrete examples of the compounds of formula (3a) are shown in the attached Tables 20 and 21, by way of indicating concrete groups corresponding to each symbol using the above abbreviations.

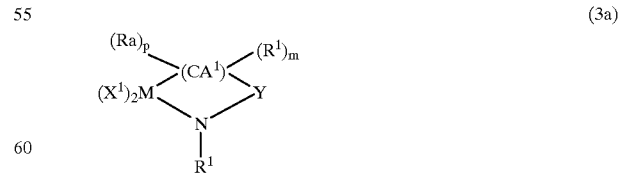

(3a)

(3b)

-continued

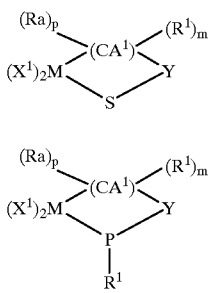

The metallocene compounds of the present invention can be prepared by the following methods.

(a) A substituted cycloalkadiene anion represented by the following formula (4Aa)

$$(Ra)_p(R^1)_m(CA^1)^-\text{—} \quad (4Aa)$$

wherein $CA^1$, Ra, $R^1$, p and m have respectively the meanings as defined above, is reacted with a binding agent represented by the following formula (5A), at a molar ratio of 2:1, $$X^2\text{—}Y\text{—}X^2 \quad (5A)$$

wherein Y has the meaning as defined above and $X^2$ represents a hydrogen atom or a halogen atom, said anion being prepared by reacting a substituted cycloalkadiene represented by the following formula (4A)

$$(Ra)_p(R^1)_m(CA^1)H \quad (4A)$$

with a metal salt type base to effect an anionization; or a substituted cycloalkadiene anion represented by formula (4Aa) is reacted with any one of the compounds represented by the following formulas (5B) to (5F), at a molar ratio of 1:1, $$X^2\text{—}Y\text{—}(CA^2)(R^1)_n(Ra)_q \quad (5B)$$

$$X^2\text{—}Y\text{—}(R^1)NH \quad (5C)$$

$$X^2\text{—}Y\text{—}OH \quad (5D)$$

$$X^2\text{—}Y\text{—}SH \quad (5E)$$

$$X^2\text{—}Y\text{—}(R^1)PH \quad (5F)$$

wherein Y, $CA^2$, Ra, $R^1$, n, q and $X^2$ have respectively the meanings as defined above, to form a compound represented by the following formula (6)

$$(Ra)_p(R^1)_m(CA^1)\text{—}Y\text{—}Z^1 \quad (6)$$

wherein $Z^1$ represents $(CA^1)(R^1)_m(Ra)_p$, $(CA^2)(R^1)_n(Ra)_q$, $(R^1)NH$, —OH, —SH or $(R^1)PH$.

(b) Subsequently, a dianion represented by the following formula (6A)

$$(Ra)_p(R^1)_m(CA^1)^-\text{—}Y\text{—}Z^-\text{—} \quad (6A)$$

wherein each symbol has the meaning as defined above, is reacted with a transition metal compound represented by the following formula (7)

$$(X^1)_2\text{—}M\text{—}(X^3)_2 \quad (7)$$

wherein M and $X^1$ have the meaning as defined above and $X^3$ represents hydrogen or a halogen atom, said dianion being prepared by reacting the compound represented by formula (6) with a metal salt type base to anionize each of the cycloalkadienyl ring and $Z^1$, thus preparing the metallocene compound represented by formula (1).

The compound represented by formula (2A) can be prepared by reacting the substituted cycloalkadiene anion represented by formula (4Aa) with the binding agent represented by formula (5A) at a molar ratio of 2:1 to obtain a bis-substituted cyclopentadiene of formula (6) wherein $Z^1$ is $(CA^1)(R^1)_m(Ra)_p$ and subsequently conducting said (b) step.

The compounds represented by formula (5B) can be prepared by reacting a substituted or unsubstituted cycloalkadiene anion represented by the following formula (4Ba)

$$(Ra)_q(R^1)_n(CA^2)^-\text{—} \quad (4Ba)$$

with a binding agent represented by formula (5A) at a molar ratio of 1:1, said anion being prepared by reacting a substituted or unsubstituted cycloalkadiene represented by the following formula (4B)

$$(Ra)_q(R^1)_n(CA^2)H \quad (4B)$$

with a metal salt type base to carry out an anionization. The compound of formula (SB) can produce the metallocene compounds of formula (2) wherein $CA^1$ and $CA^2$ are different each other.

The compounds represented by formula (5c): $X^2$—Y—$(R^1)NH$ are secondary amines wherein Y is a hydrocarbon group, a silylene group, a germanium group or a stannyl group.

The compounds represented by formula (5d): $X^2$—Y—OH are alcohols wherein Y is a hydrocarbon group, silanols wherein Y is a silylene group, germaniols wherein Y is a germanium group and stannyols wherein Y is a stannyl group.

The compounds represented by formula (5e): $X^2$—Y—SH are thiols derived from the alcohols of formula (5) by replacing with —SH.

The compounds represented by formula (5f): $X^2$—Y—$(R^1)PH$ are secondary phosphines wherein Y is as defined above.

In these compounds represented by formulas (5b)–(5f), $X^2$ is preferably a halogen atom.

The binding agents represented by formula (5A) include the compounds wherein Y is a hydrocarbon group, e.g., dichlorodimethylmethane, dichlorodiethylmethane, dichloro-di-n-propylmethane, dichloro-di-n-butylmethane, dichlorodiphenylmethane, dibromodimethylmethane, dibromodiethylmethane, dibromo-di-n-propylmethane, dibromo-di-n-butylmethane, dibromodiphenylmethane, dichlorotetramethylethane or dibromotetraethylethane; the compounds wherein Y is a silylene group, e.g., dichlorodimethylsilane, dichlorodiethylsilane, dichloro-di-n-propylsilane, dichloro-di-n-butylsilane, dichlorodiphenylsilane, dibromodimethylsilane, dibromodiethylsilane, dibromo-di-n-propylsilane, dibromo-di-n-butylsilane or dibromodiphenylsilane; the compounds wherein Y is a germanium group, e.g., dichlorogermaniumdimethyl, dichlorogermaniumdiethyl, dichlorogermanium-di-n-propyl, dichlorogermanium-di-n-butyl, dichlorogermaniumdiphenyl, dibromogermaniumdimethyl, dibromogermaniumdiethyl, dibromogermanium-di-n-propyl, dibromogermanium-di-n-butyl or dibromogermaniumdiphenyl; and similar compounds wherein Y is a stannyl group.

The substituted cycloalkadienes represented by said formulas (4A) and (4B) are substituted cyclopentadienes, substituted indenes, substituted tetrahydroindenes, substituted benzoindenes or substituted fluorenes wherein a hydrogen atom on the cycloalkadiene ring is substituted by a heteroaromatic group Ra and/or a substituent $R^1$.

These substituted cycloalkadienes can be prepared by reacting a heteroaromatic anion anionized by reacting a heteroaromatic compound with or without a halogen atom at the position bonding to the cycloalkadiene ring with a metal salt type base, with a cycloalken-one wherein a hydrogen atom on the cycloalkadiene ring to be substituted by the heteroaromatic group is substituted by an oxygen atom, thus converting into a keto form.

The transition metal compounds represented by formula (7) are metal tetrahalide compounds, e.g., titanium tetrachloride, titanium tetrabromide, titanium tetraiodide, titanium tetrafluoride, titanium trichloride, titanium tribromide, titanium triiodide, titanium trifluoride, zirconium tetrachloride, zirconium tetrabromide, zirconium tetraiodide, zirconium tetrafluoride, hafnium tetrachloride, hafnium tetrabromide, hafnium tetraiodide or hafnium tetrafluoride; and metal tri- or di-halide compounds wherein up to two of the halogen atoms are substituted by said hydrocarbon group, halogenated hydrocarbon group or silyl group, preferably metal tetrahalide compounds.

In the above-described processes, the anionization of substituted cycloalkadienes sustitued by the heteroaromatic group and the dianionization of the bis- or di-substituted cycloalkadienes mean the anionization of each 5-membered ring, i.e., cyclopentadiene ring. The former permits a linkage of two molecules by reaction with a binding agent subsequent to anionization, and the latter permits an intramolecular linkage for ring closure by is reaction with a transition metal compound subsequent to dianionization.

The metal salt type bases used in the anionization of the cyclopentadiene and aromatic rings in each step of the above-mentioned processes, include, for example, methyllithium, n-butyllithium, t-butyllithium, phenyllithium, lithium hydride, sodium hydride, potassium hydride, calcium hydride, lithium diisopropylamide, t-butyloxypotassium, methylmagnesium iodide, ethylmagnesium iodide, phenylmagnesium bromide and t-butylmagnesium bromide.

The anionization reaction of substituted cycloalkadienes substituted by the heteroaromatic group and bis- or di-substituted cycloalkadienes can be carried out with said metal salt type base in the presence of an amine compound which includes primary amines, e.g., methylamine, ethylamine, n-propyl-amine, isopropylamine, n-butylamine, tert-butylamine, aniline or ethylenediamine; secondary amines, e.g. dimethylamine, diethylamine, di-n-propylamine, diisopropylamine, di-n-butylamine, di-tert-butylamine, pyrrolidine, hexamethyldisilazane or diphenylamine; and tertiary amines, e.g. trimethylamine, triethylamine, tri-n-propylamine, triisopropylamine, tri-n-butylamine, tri-tert-butylamine, triphenylamine, N,N-dimethylaniline, N,N,N',N'-tetramethylethylenediamine, N-methylpyrrolidine or 4-dimethylaminopyridine.

Each of the above-mentioned reactions is usually carried out in an organic solvent at a reaction temperature between not lower than −100° C. and not higher than a boiling point of the solvent, preferably in the range of −70° C. to 100° C.

The solvents used in the reaction can be used without any limitation, if they are not reactive to the above starting compounds and reaction products and do not decompose them. Preferably, ethers, halogenated hydrocarbons or aromatic compounds are used. For ethers, preferable are relatively low-molecular ethers such as diethylether, diisopropylether and tetrahydrofuran, dimethoxyethane. Dichloromethane is preferable for halogenated hydrocarbons. For aromatic compounds, preferable are toluene, anisol and xylene. Further, a mixed solvent of these two or more compounds can be used.

The synthesis of the metallocene compounds represented by formula (2A) is mentioned below.

The bis-substituted cycloalkadiene prepared by reacting the substituted cycloalkadiene anion represented by formula (4Aa) with the binding agent represented by formula (5A) is generally formed as a mixture of a racemic form consisting of a compound having a steric structure unsymmetrical with respect to Y and the enantiomer thereof and a compound having a steric structure symmetrical with respect to Y.

Usually, the resultant reaction mixture to which water has been added, is allowed to stand to separate into an organic layer and a water layer, thus obtaining the bis-substituted cycloalkadiene as an organic layer. The bis-substituted cycloalkadiene can be used as it is in the form of a resulting solution for the subsequent step, but usually used after separation from the solution. For the purpose of separating the bis-substituted cycloalkadiene from the solution, the method of distilling off the solvent can be employed, for example. The separated cycloalkadiene is further purified by recrystallization, distillation, column chromatography or the like, and may be further separated into the racemic and meso forms, and each form may be further purified and used for the subsequent step.

The bis-substituted cycloalkadiene as prepared above is reacted with a metal salt type base to anionize each 5-membered ring, thereby forming the dianion represented by formula (4Ba), and then this bis-substituted cycloalkadiene dianion is reacted with the transition metal compound represented by formula (7) to achieve an intramolecular linkage for ring closure, thus forming a mixture of the racemic and meso forms of the metallocene compound represented by formula (2A).

Finally, each of the racemic and meso forms of the metallocene compounds is isolated from the above-mentioned reaction solution in the usual way and purified to obtain the racemic and meso metallocene compounds. Isolation and purification of the racemic and meso metallocene compounds can be effected by distilling the solvent off, if necessary, extraction with a suitable solvent, adsorption, filtration, recrystallization or the like. Usually, each compound is crystallized out by utilizing the difference in solubility of the compound in a solvent and then purified by recrystallization or the like.

Figure 3A:
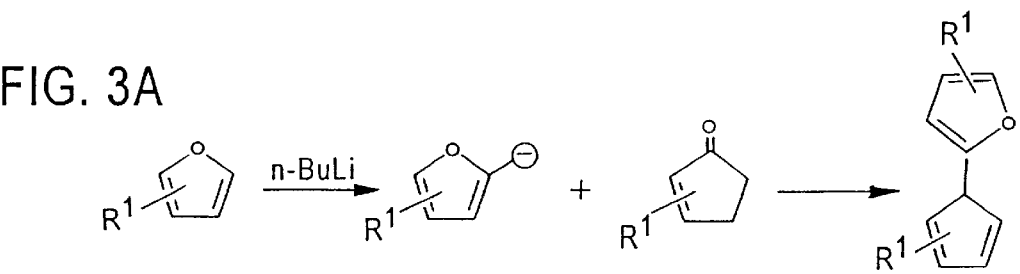
FIG. 3 is a scheme for synthesis illustrating an embodiment of the processes for the preparation of the metallocene compounds according to the present invention.
Figure 3B:
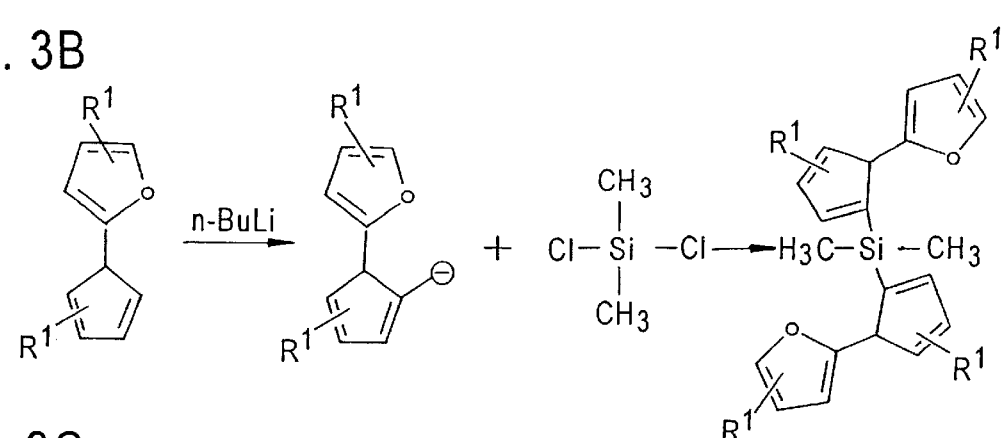
Figure 3C:
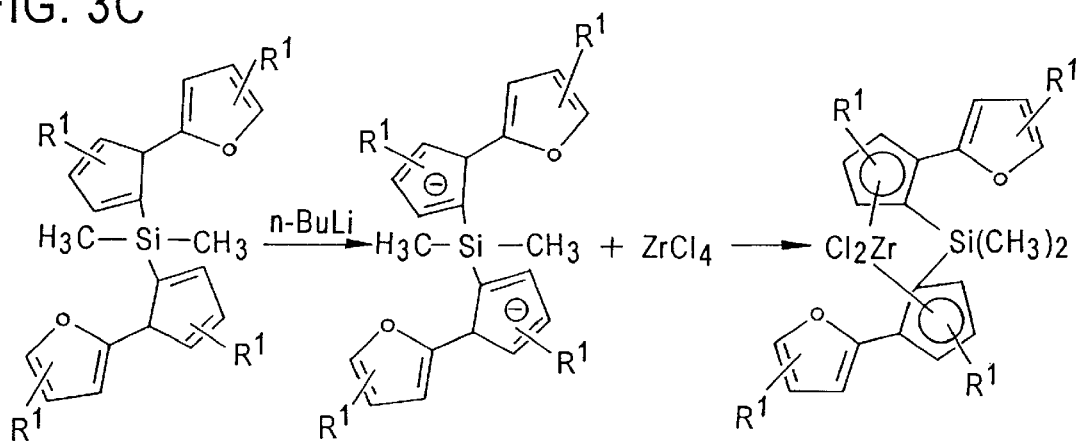

The scheme for the synthesis of dimethylsilylenebis[2-(2-furyl)-3,5-dimethylcyclopentadienyl]-zirconium dichloride (Compound No. 94 in the attached Table 3), represented by formula (2A) wherein $CA^1$ is a cyclopentadienyl group substituted by furyl and two methyl groups, Y is dimethylsilylene, M is zirconium and $X^1$ is chlorine, is shown in the attached FIG. 3.

The catalysts for olefin polymerization of the present invention contain the metallocene compound represented by formula (1) as a principal component. Preferably, the metallocene compounds represented by formula (2), and more preferably, the metallocene compounds represented by formula (2A) are used as the principal component.

The metallocene compounds represented by formula (2A) may be the racemic or meso forms isolated in said processes for the preparation, or may be those separated from the solution and purified in the form of the mixture without isolation of each form.

Other components constituting the catalyst for polymerization of olefin in combination with said metallocene compounds can include one or more compounds which are generally used in the polyolefin polymerization, selected from, for example, an aluminoxane, an ionic compound which can react with a metallocene compound to form an ionic complex and Lewis acid.

The aluminoxane is an organoaluminum compound represented by the following formula (8) or (9):

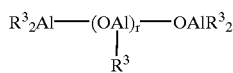

(8)

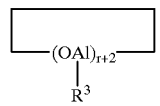

(9)

in which $R^3$ is a hydrocarbon group of 1–20 carbons, preferably 1–4 carbons and concretely represents methyl, ethyl, propyl, isopropyl, butyl or isobutyl, $R^3$ may be identical or different, and r is an integer of 1 to 1000, but said compound may be a mixture of aluminoxanes having different r values.

The ionic compounds are salts of cationic and anionic compounds. An anion has an action to cationize the metallocene compound by reaction therewith and to stabilize the cation species in the metallocene compound by formation of an ion pair. The anions include those of organoboron compounds, organoaluminum compounds or the like. The cations include metallic cations, organometallic cations, carbonium cations, tropium cations, oxonium cations, sulfonium cations, phosphonium cations and ammonium cations. Of these, preferable are ionic compounds containing a boron atom as an anion. Examples of those compounds include N,N-dimethylanilinium tetrakis(pentafluorophenyl) borate and trityltetrakis-(pentafluorophenyl)borate.

For Lewis acid, preferable is a boron-containing Lewis acid. Examples thereof include tri(n-butyl)boron, triphenyl boron, tris[3,5-bis(trifluoromethyl)-phenyl]boron, tris[(4-fluoromethyl)phenyl]boron, tris(3,5-difluorophenyl)boron, tris(2,4,6-trifluorophenyl)boron and tris(pentafluorophenyl) boron.

In addition to the above, known ionic compounds which can react with the metallocene compounds to form the ionic complexes and Lewis acids can be also used.

The proportion of the metallocene compounds and these catalyst components used is in such a range that the Al atom in the aluminoxane is 1–50,000 mols, preferably 50–20,000 mols per mol of the transition metal atom in the metallocene compound, when the aluminoxane is used as a catalyst component. When the ionic compound or Lewis acid is used as a catalyst component, the ionic compound or Lewis acid is in the range of 0.01–2,000 mols, preferably 0.1–500 mols, per mol of the transition metal atom in the metallocene compound.

In the present invention, another embodiment of the catalyst for olefin polymerization is composed of said metallocene compound, said aluminoxane and a support in the form of finely divided particles. Usually, each of the metallocene compound and the aluminoxane or a reaction product of the metallocene compound and the aluminoxane is used by supporting it on said support. The supports employed are finely divided inorganic or organic solid particles in the form of granules or spheres, the particle size of which is in the range of 5–300 µm, preferably 10–200 µm.

For the inorganic supports, preferable are metal oxides, e.g., $SiO_2$, $Al_2O_3$, MgO, $TiO_2$ and ZnO, or the mixture thereof. The supports containing as a principal component at least one selected from the group consisting of $SiO_2$, $Al_2O_3$ and MgO are especially preferable. More specifically, inorganic compounds can include $SiO_2$, $Al_2O_3$, MgO, $SiO_2$—$Al_2O_3$, $SiO_2$—MgO, $SiO_2$—$TiO_2$ and $SiO_2$—$Al_2O_3$—MgO. These inorganic oxide supports are usually calcined at a temperature of 100–1000° C. for 1–40 hrs.

The organic supports can include the polymers or copolymers of α-olefins of 2–12 carbons such as ethylene, propylene, 1-butene or 4-methyl-1-pentene, and the polymers or copolymers of styrene or styrene derivatives.

The process for the production of an olefin polymer according to the present invention comprises polymerizing an olefin in the presence of said catalyst for olefin polymerization. Preferably, an olefin is polymerized in the presence of the catalyst for olefin polymerization formed from metallocene compounds, aluminoxanes and said supports as well as organoaluminum compounds.

The term "polymerization" in the present specification is used in the sense to include a homopolymerization and copolymerization. The term "olefin polymer" includes a homopolymer of one olefin and a copolymer of two or more olefins.

In the present invention, the polymerizable olefins include straight-chain a-olefins, e.g., ethylene, propylene, 1-butene, 1-hexene, 1-pentene, 1-decene, 1-dodecene, 1-tetradecene, 1-hexadecene, 1-octadecene or 1-eicosene; branched-chain α-olefins, e.g., 3-methyl-l-butene, 4-methyl-1-pentene or 2-methyl-l-pentene; and the mixture of these two or more species.

The processes for the production of the olefin polymer according to the present invention can produce not only homopolymers of said olefins, but also random copolymers comprising, e.g., a combination of two components such as ethylene/propylene, propylene/1-butene, a combination of three components such as ethylene/propylene/1-butene, block copolymers by varying kinds of olefins which feed in a multistage polymerization.

The polymerization of a cyclic olefin, a diene, a styrene and the derivatives thereof and other polymerizable monomers having a double bond or the copolymerization with an α-olefin can be carried out by use of the above-mentioned processes for the production of olefin polymers.

The polymerizable cyclic olefins include, for example, cyclobutene, cyclopentene, cyclohexene, cycloheptene, norbornene, 5-methyl-2-norbornene, 5-ethyl-2-norbornene, phenylnorbornene and indanylnorbornene. The dienes include, for example, cyclic dienes, e.g., 5-methylene-2-norbornene, 5-ethylidene-2-norbornene, 5-propylidene-5-norbornene, dicyclopentadiene or 5-vinyl-2 -norbornene; and acyclic dienes, e.g., 1,3-butadiene, isoprene, 1,4-hexadiene, 4-methyl-1,4-hexadiene, 5-methyl-1,4-hexadiene, 5-methyl-1,5-heptadiene, 6-methyl-1,5-heptadiene, 1,7-octadiene, 6-methyl-1,7-octadiene, 7-methyl-1,6-octadiene, 1,8-nonadiene or 1,9-decadiene. The styrenes and their derivatives include, for example, styrene, p-chlorostyrene, p-methylstyrene, p-tert-butylstyrene, α-methylstyrene and vinylnaphthalene. Other polymerizable monomers having a double bond include, for example, vinylcyclohexane, vinyl chloride, 4-trimethylsiloxy-1,6-heptadiene, 5-(N,N-diisopropylamino)-1-pentene, methylmethacrylate and ethylacrylate.

The organoaluminum compounds coexistent with the olefin polymerization catalyst in the olefin polymerization system are triethylaluminum, triisopropylaluminum, triisobutylaluminum, tri-n-butylaluminum, tri-n- hexylaluminum, diisobutylaluminum hydride or the like and the mixture thereof, and triethylaluminum and triisobutylaluminum are preferably used.

In the processes for the production of olefin polymers according to the present invention, both of a liquid-phase polymerization and a vapor-phase polymerization can be employed as a process for the polymerization of olefins. In the liquid-phase polymerization, an inert hydrocarbon may be a solvent, and further a liquid olefin itself such as a liquid propylene and a liquid 1-butene can be used as a solvent. The solvents for polymerization include an aromatic hydrocarbon, e.g., benzene, toluene, ethylbenzene or xylene; an aliphatic hydrocarbon, e.g., butane, isobutane, pentane, hexane, heptane, octane, decane, dodecane, hexadecane or octadecane; an alicyclic hydrocarbon, e.g., cyclopentane, methylcyclopentane, cyclohexane or cyclooctane; and a petroleum cut, e.g., gasoline, kerosene or gas oil.

The polymerization process may employ either of batchwise, semi-continuous and continuous methods. Further, the polymerization may be carried out in two or more stages divided by changing the reaction conditions.

The metallocene compounds used in the polymerization process, particularly the metallocene compounds of formula (2A), may be either of an isolated racemic or meso form, or the separated and purified mixture thereof. In particular, the isolated racemic form achieves an extremely great effect in making the molecular weight of the produced polypropylene higher.

The concentration of the metallocene compound within the polymerization reaction system, with no particular limitation thereon, is preferably in the range of $10^{-2}$–$10^{-10}$ mol/l based on the transition metal.

The pressure of olefins in the polymerization reaction system, with no particular limitation thereon, is preferably in the range of normal pressure to 50 kg/cm$^2$. Further, the polymerization temperature, with no particular limitation thereon, is usually in the range of –50 to 250° C., preferably –30 to 100° C. The regulation of the molecular weight upon the polymerization can be effected by known means, for example, choice of the temperature or introduction of hydrogen.

The olefin polymers produced by the above-mentioned processes are provided for various forming or molding materials, through conventional process steps such as the deactivation treatment of catalyst, the treatment for catalyst residue, drying or the like.

EXAMPLE

Example 1

Synthesis of dimethylsilylenebis[3-(2-furyl)-2,5-dimethylcyclopentadienyl]zirconium dichloride (Compound No. 254)

(a1) Synthesis of 1-(2-furyl)-2,4-dimethylcyclopentadiene

A 500 ml glass reaction vessel was charged with 9.4 g (0.10 mol) of furan and 150 ml of tetrahydrofuran (THF) and cooled to –20° C. on a dry ice/methanol bath. To the mixture were added dropwise 90 ml (0.14 mmol) of an n-butyllithium/hexane solution of 1.54 mol/l. After the addition was completed, the mixture was raised to room temperature and stirred for 6 hrs. The mixture was again cooled to –20° C. on a dry ice/methanol bath and 30 ml of a THF solution containing 15.2 g (0.14 mol) of 2,4-dimethylcyclopenten-1-one were added dropwise. After the addition was completed, the mixture was raised to room temperature and stirred for 16 hrs.

The reaction solution was cooled to –20° C. on a dry ice/methanol bath and 10 ml of 2N-hydrochloric acid were added dropwise. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 20.3 g (92% yield) of a yellow liquid of 1-(2-furyl)-2,4-dimethylcyclopentadiene. The structure was identified by NMR.

(a2) Synthesis of dimethylbis[3-(2-furyl)-2,5-dimethylcyclopentadienyl]silane

A 500 ml glass reaction vessel was charged with 20.3 g (0.13 mol) of 1-(2-furyl)-2,4-dimethylcyclopentadiene and 130 ml of THF and cooled to –30° C. on a dry ice/methanol bath. To the mixture were added dropwise 85 ml (0.13 mmol) of an n-butyllithium/hexane solution of 1.54 mol/l. After the addition was completed, the mixture was raised to room temperature and stirred for 16 hrs. The mixture was again cooled to –30° C. on a dry ice/methanol bath and 30 ml of a THF solution containing 8.2 g (0.064 mol) of dimethyl dichlorosilane were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 7.7 g (33% yield) of dimethylbis[3-(2-furyl)-2,5-dimethylcyclopentadienyl]-silane as a yellow liquid. The structure was identified by NMR.

(b) Synthesis of dimethylsilylenebis[3-(2-furyl)-2,5-dimethylcyclopentadienyl]zirconium dichloride A 100 ml glass reaction vessel was charged with 2.0 g (0.050 mol) of potassium hydride (KH) and 40 ml of THF and cooled to –70° C. on a dry ice/methanol bath. To the mixture were added dropwise 40 ml of a THF solution containing 7.7 g (0.021 mol) of dimethylbis[3-(2-furyl)-2,5-dimethylcyclopentadienyl]silane as synthesized above. After the addition was completed, the mixture was returned to room temperature and stirred for 16 hrs. The reaction solution was allowed to stand and a supernatant solution was transferred into a 100 ml glass reaction vessel. The solvent in the supernatant solution was distilled off under reduced pressure, 15 ml of dichloromethane were added, and the reaction solution was solidified with liquid nitrogen, to which were added 45 ml of a dichloromethane suspension containing 6.2 g (0.027 mol) of tetrachlorozirconium. Subsequently, the mixture was raised to room temperature and stirred for 16 hrs. A part of the reaction solution was withdrawn and determined by $^1$H-NMR, by which it was found to be a mixture of a racemic form/meso form (molar ratio=58/42).

The solvent was distilled off under reduced pressure, the residue was extracted with hexane and recrystallized from toluene/hexane to obtain 90 mg (0.8% yield) of dimethylsilylenebis[3-(2-furyl)-2,5-dimethylcyclopentadienyl]zirconium dichloride (racemic form/meso form (molar ratio)=49/51).

$^1$H-NMR (CDCl$_3$) Racemic form δ: 1.04 (s, 6H), δ: 2.24 (s, 6H), δ: 2.31 (s, 6H), δ: 6.47 (m, 4H), δ: 7.06 (5, 2H), δ: 7.44 (dd, 2H), Meso form δ: 1.04 (s, 3H), δ: 1.06 (s, 3H), δ: 2.23 (s, 6H), δ: 2.35 (s, 6H), δ: 6.42 (d, 4H), δ: 6.94 (s, 2H), δ: 7.41 (t, 2H).

Example 2

Synthesis of dimethylsilylenebis[2-(2-furyl)-3,5-dimethylcyclopentadienyl]zirconium dichloride
(Compound No. 94)

(b) Synthesis of dimethylsilylenebis[2-(2-furyl)-3,5-dimethylcyclopentadienyl]zirconium dichloride A 100 ml glass reaction vessel was charged with 3.98 g (0.011 mol) of dimethylbis[2-(2-furyl)-4,5-dimethylcyclopentadienyl]silane synthesized by a similar procedure as in step (a) of Example 1 and 30 ml of THF, and cooled to −30° C. on a dry ice/methanol bath. To the mixture were added dropwise 15 ml (0.023 mmol) of an n-butyllithium/hexane solution of 1.52 mol/l. After the addition was completed, the mixture was raised to room temperature and stirred for 16 hrs. The solvent in the reaction solution was distilled off under reduced pressure, 10 ml of dichloromethane were added, and the reaction solution was solidified with liquid nitrogen, to which were added 30 ml of a dichloromethane suspension containing 2.5 g (0.011 mol) of tetrachloro-zirconium. Subsequently, the mixture was raised to room temperature and stirred for 16 hrs. A part of the reaction solution was withdrawn and determined by $^1$H-NMR, by which it was found to be a racemic form/meso form (molar ratio=77/23).

The solvent was distilled off under reduced pressure and the residue was extracted with hexane to afford 2.3 g of dimethylsilylenebis[2-(2-furyl)-3,5-dimethylcyclopentadienyl]zirconium dichloride (racemic form/meso form (molar ratio)=78/22, yield 40.6%). Recrystallization gave 140 mg of the racemic form (purity 99% or more).

Figure 2:
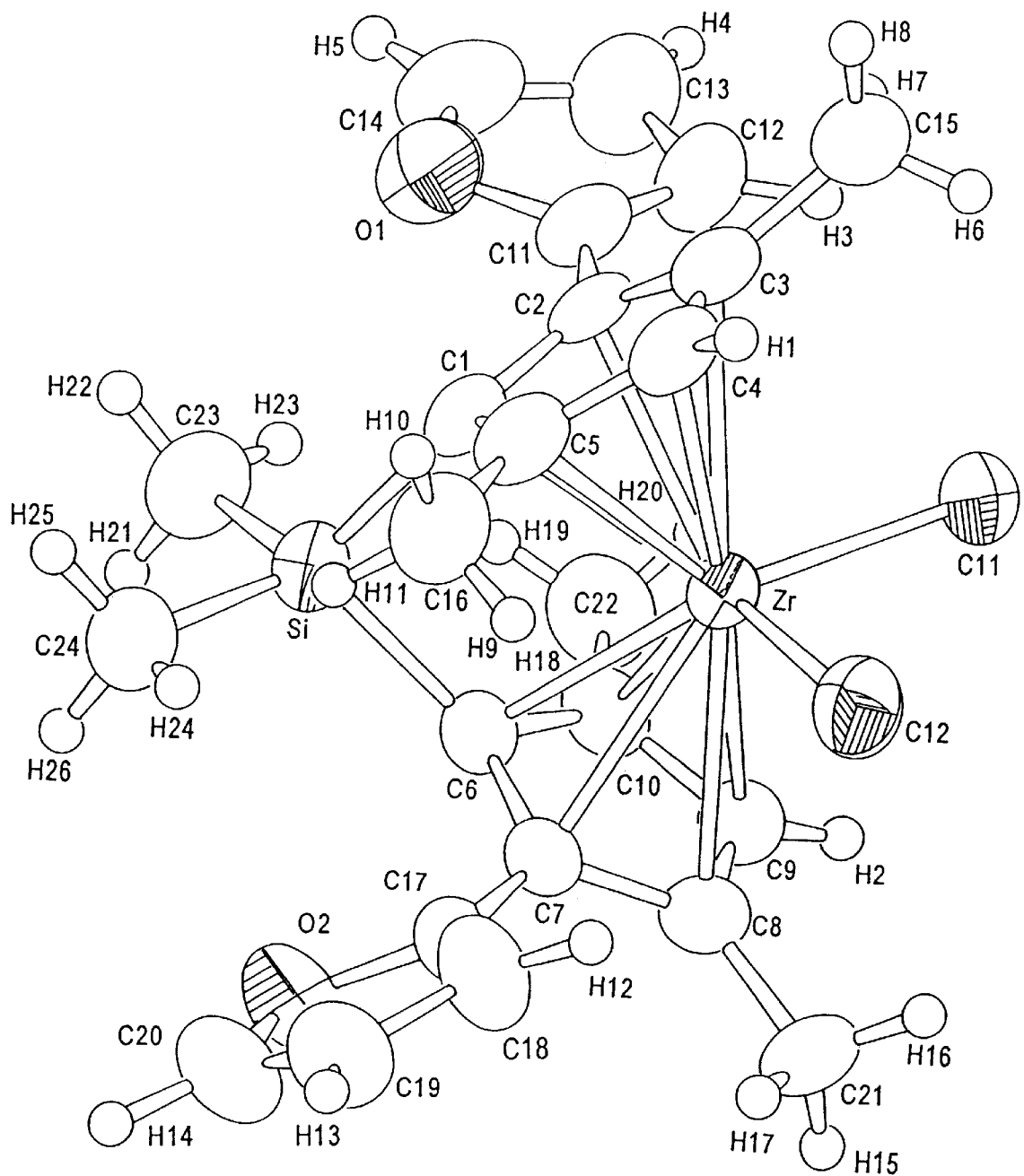
FIG. 2 is an ORTEP diagram obtained from a single crystal, X-ray structural analysis of compound No. 94 synthesized in Example 2, rac-dimethylsilylenebis[2-(2-furyl)-3,5-dimethylcyclopentadienyl]zirconium dichloride.

The ORTEP diagram of the resultant rac-dimethylsilylenebis[2-(2-furyl)-3,5-dimethylcyclopentadienyl]zirconium dichloride is shown in FIG. 2.

$^1$H-NMR (CDCl$_3$)

Racemic form δ: 0.62 (s, 6H), δ: 1.66 (s, 6H), δ: 2.27 (s, 6H), δ: 6.38 (dd, 2H), δ: 6.44 (dd, 2H), δ: 6.59 (s, 2H), δ: 7.42 (dd, 2H)

Meso form δ: 0.18 (s, 3H), δ: 1.06 (s, 3H), δ: 2.26 (s, 6H), δ: 2.36 (s, 6H), δ: 5.94 (dd, 2H), δ: 6.14 (dd, 2H), δ: 6.50 (s, 2H), δ: 7.14 (dd, 2H).

Example 3

Synthesis of dimethylsilylenebis[2-(2-furyl)-4,5-dimethylcyclopentadienyl]zirconium dichloride
(Compound No. 95)

(a1) Synthesis of 1-(2-furyl)-3,4-dimethylcyclopentadiene

A 1 l glass reaction vessel was charged with 21.0 g (0.31 mol) of furan and 400 ml of diethyl ether and cooled to −30° C. on a dry ice/methanol bath. To the mixture were added dropwise 200 ml (0.31 mmol) of an n-butyllithium/hexane solution of 1.53 mol/l. After the addition was completed, the mixture was raised to room temperature and stirred for 4 hrs. The mixture was again cooled to −30° C. on a dry ice/methanol bath and 100 ml of a diethyl ether solution containing 33.0 g (0.30 mol) of 3,4-dimethylcyclopenten-1-one were added dropwise. After the addition was completed, the mixture was returned to room temperature and stirred for 16 hrs.

To the reaction solution was added distilled water, this solution was transferred into a separatory funnel and washed three times with brine. Subsequently, the solution was shaken twice with 50 ml of 5N hydrochloric acid and washed with brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 24.6 g (51% yield) of 1-(2-furyl)-3,4-dimethylcyclopentadiene as a red liquid. The structure was identified by NMR.

(a2) Synthesis of dimethylbis[2-(2-furyl)-4,5-dimethylcyclopentadienyl]silane

A 1 l glass reaction vessel was charged with 24.3 g (0.15 mol) of 1-(2-furyl)-3,4-dimethylcyclopentadiene and 300 ml of THF and cooled to −30° C. on a dry ice/methanol bath. To the mixture were added dropwise 100 ml (0.15 mmol) of a n-butyllithium/hexane solution of 1.52 mol/l. After the addition was completed, the mixture was raised to room temperature and stirred for 3 hrs. The mixture was again cooled to −30° C. on a dry ice/methanol bath and 50 ml of of a THF solution containing 9.8 g (0.076 mol) of dimethyl dichlorosilane were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column and recrystallization with toluene/hexane gave 19.4 g (68% yield) of dimethylbis-[2-(2-furyl)-4,5-dimethylcyclopentadienyl]silane as yellow crystals.

(b) Synthesis of dimethylsilylenebis[2-(2-furyl)-4,5-dimethylcyclopentadienyl]zirconium dichloride A 500 ml glass reaction vessel was charged with 10.0 g (0.027 mol) of dimethylbis[2-(2-furyl)-4,5-dimethylcyclopentadienyl]silane and 200 ml of THF and cooled to −30° C. on a dry ice/methanol bath. To the mixture was added dropwise 35 ml (0.053 mmol) of an n-butyllithium/hexane solution of 1.52 mol/l. After the addition was completed, the mixture was raised to room temperature and stirred for 16 hrs. The solvent was distilled off under reduced pressure, 200 ml of toluene were added, and the solution was cooled to −70° C. on a dry ice/methanol bath. To the solution, 6.2 g (0.027 mol) of tetrachlorozirconium were added as it was solid. Subsequently, the mixture was raised to room temperature, stirred for 16 hrs. and heated at 80° C. for 4 hrs. A part of the reaction solution was withdrawn and determined by $^1$H-NMR, by which it was found to be a racemic form/meso form (molar ratio=61/39).

The solvent was distilled off under reduced pressure and the residue was extracted with hexane to afford 2.5 g of dimethylsilylenebis[2-(2-furyl)-4,5-dimethylcyclopentadienyl]zirconium dichloride (racemic form/meso form=58/42, 17.5% yield) as yellow powders. Further recrystallization gave 120 mg of the racemic form (purity 99% or more) and 170 mg of the meso form (purity 99% or more).

$^1$H-NMR (CDCl$_3$) (See, FIG. 1) Racemic form δ: 0.79 (s, 6H), δ: 1.45 (s, 6H), δ: 2.19 (s, 6H), δ: 6.41 (dd, 2H), δ: 6.55 (dd, 2H), δ: 6.72 (s, 2H), δ: 7.39 (dd, 2H)

Meso form δ: 0.62 (s, 3H), δ: 1.00 (s, 3H), δ: 2.02 (s, 6H), δ: 2.29 (s, 6H), δ: 6.12 (d, 4H), δ: 6.65 (d, 2H), δ: 7.13 (t, 2H).

Example 4

Synthesis of dimethylsilylenebis[3-(2-thienyl)-2,5-dimethylcyclopentadienyl]zirconium dichloride (Compound No. 274)

(a1) Synthesis of 1-(2-thienyl)-2,4-dimethylcyclopentadiene

A 200 ml glass reaction vessel was charged with 5.3 g (0.063 mol) of thiophene and 60 ml of THF and cooled to −10° C. on a dry ice/methanol bath. To the mixture were added dropwise 41 ml (0.064 mmol) of a n-butyllithium/hexane solution of 1.56 mol/l. After the addition was completed, the mixture was raised to room temperature and stirred for one hour. The mixture was again cooled to −20° C. on a dry ice/methanol bath and 30 ml of a THF solution containing 7.0 g (0.064 mol) of 2,4-dimethylcyclopenten-1-one were added dropwise. After the addition was completed, the mixture was raised to room temperature and stirred for 16 hrs.

The reaction solution was cooled to −20° C. on a dry ice/methanol bath and 7 ml of 2N-hydrochloric acid were added dropwise. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 9.7 g (87% yield) of a yellow-orange liquid of 1-(2-thienyl)-2,4-dimethylcyclopentadiene. The structure was identified by NMR.

(a2) Synthesis of dimethylbis[3-(2-thienyl)-2,5-dimethylcyclopentadienyl]silane

A 100 ml glass reaction vessel was charged with 3.53 g (0.020 mol) of 1-(2-thienyl)-2,4-dimethylcyclopentadiene as synthesized above and 40 ml of THF and cooled to −30° C. on a dry ice/methanol bath. To the mixture were added dropwise 14 ml (0.022 mmol) of an n-butyllithium/hexane solution of 1.56 mol/l. After the addition was completed, the mixture was raised to room temperature and stirred for 16 hrs. The mixture was again cooled to −30° C. on a dry ice/methanol bath and 20 ml of a THF solution containing 1.3 g (0.010 mol) of dimethyl dichlorosilane were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 1.3 g (16% yield) of a yellow liquid of dimethylbis[3-(2-thienyl)-2,5-dimethylcyclopentadienyl]silane. The structure was identified by NMR.

(b) Synthesis of dimethylsilylenebis[3-(2-thienyl)-2,5-dimethylcyclopentadienyl]zirconium dichloride A 100 ml glass reaction vessel was charged with 0.4 g (0.010 mol) of potassium hydride (KH) and 30 ml of THF and cooled to −70° C. on a dry ice/methanol bath. To the mixture were added dropwise 20 ml of a THF solution containing 1.2 g (0.0030 mol) of dimethylbis[3-(2-thienyl)-2,5-dimethylcyclopentadienyl]silane as synthesized above. After the addition was completed, the mixture was raised to room temperature and stirred for 16 hrs. The reaction solution was allowed to stand and a supernatant solution was transferred into a 100 ml glass reaction vessel. The solvent in the supernatant solution was distilled off under reduced pressure, 15 ml of dichloromethane were added, and the reaction solution was solidified with liquid nitrogen, to which were added 45 ml of a dichloromethane suspension containing 0.7 g (0.0031 mol) of tetrachlorozirconium. Subsequently, the mixture was raised to room temperature and stirred for 16 hrs. A part of the reaction solution was withdrawn and determined by $^1$H-NMR, by which it was found to be a racemic form/meso form (molar ratio=55/45).

The solvent was distilled off under reduced pressure, the residue was extracted with hexane and recrystallized with toluene/hexane to obtain 30 mg (2% yield) as yellow crystals of dimethylsilylenebis[3-(2-thienyl)-2,5-dimethylcyclopentadienyl)zirconium dichloride (racemic form/meso form (molar ratio)=60/40).

$^1$H-NMR (CDCl$_3$) Racemic form δ: 1.05 (s, 6H), δ: 2.25 (s, 6H), δ: 2.35 (s, 6H), δ: 6.99 (s, 2H), δ: 7.09 (dd, 2H), δ: 7.20 (dd, 2H), δ: 7.30 (dd, 2H)

Meso form δ: 1.05 (s, 3H), δ: 1.06 (s, 3H), δ: 2.26 (s, 6H), δ: 2.36 (s, 6H), δ: 6.87 (s, 2H), δ: 7.05 (dd, 2H), δ: 7.19 (dd, 2H), δ: 7.26 (dd, 2H).

Example 5

Synthesis of dimethylsilylenebis[2-(2-furyl)-indenyl]-zirconium dichloride (Compound No. 424)

(a1) Synthesis of 2-(2-furyl)-indene

A 500 ml glass reaction vessel was charged with 4.7 g (0.069 mol) of furan and 100 ml of THF and cooled to −50° C. on a dry ice/methanol bath. To the mixture were added dropwise 48 ml (0.073 mmol) of an n-butyllithium/hexane solution of 1.52 mol/l. After the addition was completed, the mixture was raised to room temperature and stirred for 3 hrs. The mixture was again cooled to −30° C. on a dry ice/methanol bath and 100 ml of a THF solution containing 9.1 g (0.069 mol) of 2-indanone were added dropwise. After the addition was completed, the mixture was raised to room temperature and stirred for 16 hrs.

The reaction solution was cooled to −20° C. on a dry ice/methanol bath and 10 ml of 2N-hydrochloric acid were added dropwise. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 3.2 g (25% yield) of 2-(2-furyl)-indene as colorless crystals. The structure was identified by NMR.

(a2) Synthesis of dimethylbis[2-(2-furyl)-indenyl]silane

A 200 ml glass reaction vessel was charged with 1.3 g (0.0070 mol) of 2-(2-furyl)-indene as synthesized above, 0.09 g (0.001 mol) of copper cyanide and 30 ml of THF and cooled to −50° C. on a dry ice/methanol bath. To the mixture were added dropwise 5.2 ml (0.0079 mmol) of an n-butyllithium/hexane solution of 1.52 mol/l. After the addition was completed, the mixture was raised to room temperature and stirred for 16 hrs. The mixture was again cooled to −50° C. on a dry ice/methanol bath and 20 ml of THF solution containing 0.5 g (0.0039 mol) of dimethyl dichlorosilane were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 1.1 g (72% yield) of dimethylbis[2-(2-furyl)-indenyl]silane as light green crystals.

(b) Synthesis of dimethylsilylenebis[2-(2-furyl)-indenyl]zirconium dichloride

A 100 ml glass reaction vessel was charged with 1.1 g (0.0025 mol) of dimethylbis[2-(2-furyl)-indenyl]silane as synthesized above and 30 ml of THF and cooled to −50° C. on a dry ice/methanol bath. To the mixture were added dropwise 3.6 ml (0.0055 mmol) of an n-butyllithium/hexane solution of 1.52 mol/l. After the addition was completed, the mixture was raised to room temperature and stirred for 16 hrs. The solvent in the reaction solution was distilled off under reduced pressure, 10 ml of dichloromethane were added, and the reaction solution was solidified with liquid nitrogen, to which were added 30 ml of a dichloromethane suspension containing 0.6 g (0.0026 mol) of tetrachlorozirconium. Subsequently, the mixture was raised to room temperature and stirred for 16 hrs. A part of the reaction solution was withdrawn and determined by $^1$H-NMR, by which it was found to be dimethylsilylenebis[2-(2-furyl)-indenyl]-zirconium dichloride (racemic form/meso form (molar ratio=75/25).

The solvent was distilled off under reduced pressure, the residue was extracted with toluene and recrystallized with toluene to obtain 140 mg (10% yield) of a racemic form (purity 99% or more) of dimethylsilylenebis-[2-(2-furyl)-indenyl)zirconium dichloride.

$^1$H-NMR (CDCl$_3$) Racemic form δ: 1.11 (s, 6H), δ: 6.41 (dd, 2H), δ: 6.48 (dd, 2H), δ: 6.72 (m, 2H), δ: 6.89 (m, 2H), δ: 6.97 (s, 2H), δ: 7.33 (m, 2H), δ: 7.52 (dd, 2H), δ: 7.55 (m, 2H).

Example 6

Polymerization of Propylene

A SUS autoclave was charged with 1 liter of toluene and a toluene solution of methylaluminoxane (MMAO3A, manufactured by Toso-Aczo Co. Ltd.) in an amount equivalent to Al/Zr (molar ratio)=10,000, to which was added separately each solution containing in 3 ml of a toluene solution, 1.35×10$^{-6}$ mol of the metallocene compound of Compound No. 254 (racemic form/meso form (molar ratio)=49/51) synthesized in Example 1, 0.62×10$^{-6}$ mol of the metallocene compound of Compound No. 94 (racemic form 99%) synthesized in Example 2, 0.55×10$^{-6}$ mol of the metallocene compound of Compound No. 95 (racemic form 99%) synthesized in Example 3, 1.61×10$^{-6}$ mol of the metallocene compound of Compound No. 274 (racemic form/meso form (molar ratio)=60/40) synthesized in Example 4, and 0.30 x 10–6 mol of the metallocene compound of Compound No. 424 (racemic form 99%) synthesized in Example 5, respectively, and each mixture was heated to 30° C. Into the autoclave was introduced propylene at a pressure of 0.3 MPaG and a polymerization was carried out for one hour. After the polymerization was completed, a polymer was filtered and a catalyst component was decomposed with 1 liter of hydrochloric acidic methanol. Subsequently, 1e filtration, washing and drying were carried out in order to obtain a polypropylene in an amount of 43.1 g, 42.7 g, 20.9 g, 33.6 g and 4.6 g, respectively.

The analytical values for the resultant polypropylene are shown in Table 1.

Example 7

Synthesis of dimethylsilylenebis[2-(2-thienyl)-4,5dimethylcyclopentadienyl]zirconium dichloride (a1) Synthesis of 1-(2-thienyl)-3,4-dimethylcyclopentadiene A 1 l glass reaction vessel was charged with 25.3 g (0.30 mol) of thiophene and 350 ml of THF and the mixture was cooled to −70° C. on a dry ice/methanol bath. To the mixture were added dropwise 200 ml (0.30 mol) of an n-butyllithium/hexane solution of 1.52 mol/l. After the addition was completed, the mixture was raised to room temperature and stirred for 16 hrs. The mixture was again cooled to −30° C. on a dry ice/methanol bath and 100 ml of a THF solution containing 33.0 g (0.30 mol) of 3,4-dimethylcyclopenten-1-one were added dropwise. After the addition was completed, the mixture was raised to room temperature and stirred for 16 hrs.

To the reaction solution was added distilled water. This solution was transferred into a separatory funnel and washed three times with brine. Subsequently, the solution was shaken twice with 50 ml of 5N hydrochloric acid and washed with brine until it was neutral. Anhydrous sodium sulfate was added and the solution was allowed to stand overnight and dried. Anhydrous sodium sulfate was filtered off and the solvent was distilled off under reduced pressure. Purification of the residue by a silica gel column gave 49.7 g (94% yield) of 1-(2-thienyl)-3,4-dimethyl-cyclopentadiene as a yellow solid. The structure was identified by NMR.

(a2) Synthesis of dimethylbis[2-(2-thienyl)-4,5-dimethylcyclopentadienyl]silane

A 1 l glass reaction vessel was charged with 49.0 g (0.28 mol) of 1-(2-thienyl)-3,4-dimethylcyclopentadiene and 400 ml of THF and the mixture was cooled to −30° C. on a dry ice/methanol bath. To the mixture were added dropwise 183 ml (0.28 mol) of an n-butyllithium/hexane solution of 1.52 mol/l. After the addition was completed, the mixture was raised slowly to room temperature and stirred for 2 hrs. The mixture was again cooled to −30° C. on a dry ice/methanol bath and 100 ml of a THF solution containing 17.9 g (0.14 mol) of dimethyl dichlorosilane were added dropwise. After the addition was completed, the mixture was raised slowly to room temperature and stirred for 16 hrs.

To the reaction solution was added distilled water. The suspended matter was filtered off, and the solution was then transferred into a separatory funnel and washed with brine until it was neutral. Anhydrous sodium sulfate was added and the reaction solution was allowed to stand overnight and dried. Anhydrous sodium sulfate was filtered off and the solvent was distilled off under reduced pressure. Purification of the residue by a silica gel column and recrystallization with toluene/hexane gave 35.1 g (62% yield) of dimethylbis[2-(2-thienyl)-4,5-dimethylcyclopentadienyl]silane as yellow crystals.

(b) Synthesis of dimethylsilylenebis[2-(2-thienyl)-4,5-dimethylcyclopentadienyl]zirconium dichloride A 500 ml glass reaction vessel was charged with 13.5 g (0.033 mol) of dimethylbis[2-(2-thienyl)-4,5-dimethylcyclopentadienyl]silane and 300 ml of diethyl ether and the mixture was cooled to −70° C. on a dry ice/methanol bath. To the mixture were added dropwise 43 ml (0.065 mol) of an n-butyllithium/hexane solution of 1.52 mol/l. After the addition was completed, the mixture was raised slowly to room temperature and stirred for 16 hrs. The solvent was distilled off under reduced pressure. To the residue was added 400 ml of toluene and the mixture was cooled to −70° C. on a dry ice/methanol bath. 7.7 g (0.033 mol) of zirconium tetrachloride in a solid state was added. Subsequently the mixture was raised slowly to room temperature, stirred for 16 hrs and heated at 80° C. in an oil bath.

Recrystallization with toluene/hexane gave 110 mg of dimethylsilylenebis[2-(2-thienyl)-4,5-dimethylcyclopentadienyl]zirconium dichloride as red crystals (racemic form, purity 99% or more).

$^1$H-NMR (CDCl$_3$) Racemic form δ: 0.81 (s, 6H), δ: 1.54 (s, 6H), δ: 2.22 (s, 6H), δ: 6.69 (s, 2H), δ: 6.94 (dd, 2H), δ: 7.11 (dd, 2H), δ: 7.27 (dd, 2H).

Polymerization of propylene using dimethylsilylenebis[2-(2-thienyl)-4,5-dimethylcyclopentadienyl]zirconium dichloride A SUS autoclave was charged successively with 1 liter of toluene, a toluene solution of methylaluminoxane (MMAO3A, manufactured by Toso-Aczo Co., Ltd.) (Al/Zr= 10,000) and 3 ml (1.05×10$^{-6}$ mol) of a toluene solution of dimethylsilylenebis[2-(2-thienyl)-4,5-dimethylcyclopentadienyl]zirconium dichloride, and the mixture was heated to 30° C. Into the autoclave was introduced propylene at a pressure of 0.3 MPaG and a polymerization was carried out for one hour. After the polymerization was completed, a catalyst component was decomposed with 1 liter of hydrochloric acidic methanol. Subsequently, filtration, washing and drying were carried out to obtain 1.88 g of polypropylene.

The analytical values for the resultant polypropylene are shown in Table 1.

Example 8

Synthesis of dimethylsilylenebis[2-(2-(5-methyl)furyl)-4,5-dimethylcyclopentadienyl]zirconium dichloride (a1) Synthesis of 1-(2-(5-methyl)furyl)-3,4-dimethylcyclopentadiene A 1 l glass reaction vessel was charged with 30.0 g (0.37 mol) of 2-methylfuran and 400 ml of THF and the mixture was cooled to −70° C. on a dry ice/methanol bath. To the mixture was added dropwise 236 ml (0.37 mol) of an n-butyllithium/hexane solution of 1.57 mol/l. After the addition was completed, the mixture was raised to room temperature and stirred for 16 hrs. The mixture was again cooled to −30° C. on a dry ice/methanol bath and 100 ml of a THF solution containing 40.8 g (0.37 mol) of 3,4-dimethylcyclopenten-1-one were added dropwise. After the addition was completed, the mixture was raised to room temperature and stirred for 16 hrs.

To the reaction solution was added distilled water. This solution was transferred into a separatory funnel and washed three times with brine. Subsequently, the solution was shaken twice with 50 ml of 0.5N hydrochloric acid and washed with brine until it was neutral. Anhydrous sodium sulfate was added and the solution was allowed to stand overnight and dried. Anhydrous sodium sulfate was filtered off and the solvent was distilled off under reduced pressure. Purification of the residue by a silica gel column gave 47.0 g (90% yield) of 1-(2-(5-metyl)furyl)-3,4-dimethylcyclopentadiene as a red liquid. The structure was identified by NMR.

(a2) Synthesis of dimethylbis[2-(2-(5-methyl)furyl)-4,5-dimethylcyclopentadienyl]silane A 1 l glass reaction vessel was charged with 47.0 g (0.27 mol) of 1-(2-(5-methyl)furyl)-3,4-dimethylcyclopentadiene, 1.0 g (0.008 mol) of coprous isocyanate and 400 ml of THF and the mixture was cooled to −70° C. on a dry ice/methanol bath. To the mixture were added dropwise 175 ml (0.27 mol) of an n-butyllithium/hexane solution of 1.57 mol/l. After the addition was completed, the mixture was raised to room temperature and stirred for 3 hrs. The mixture was again cooled to −40° C. on a dry ice/methanol bath and 50 ml of a THF solution containing 17.4 g (0.13 mol) of dimethyl dichlorosilane were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue by a silica gel column and recrystallization with toluene/hexane gave 37.7 g (75% yield) of dimethylbis-[2-(2-(5-methyl)furyl)-4,5-dimethylcyclopentadienyl]silane as yellow crystals.

(b) Synthesis of dimethylsilylenebis[2-(2-(5-methyl)furyl)-4,5-dimethylcyclopentadienyl]zirconium dichloride A 500 ml glass reaction vessel was charged with 10.0 g (0.027 mol) of dimethylbis[2-(2-(5-methyl)furyl)-4,5-dimethylcyclopentadienyl]silane and 150 ml of THF and the mixture was cooled to −70° C. on a dry ice/methanol bath. To the mixture were added dropwise 35 ml (0.055 mol) of an n-butyllithium/hexane solution of 1.57 mol/l. After the addition was completed, the mixture was raised to room temperature and stirred for 16 hrs. The solvent was distilled off under reduced pressure. To the residue was added 300 ml of toluene and the mixture was cooled to −70° C. on a dry ice/methanol bath. 6.3 g (0.027 mol) of zirconium tetrachloride in a solid state was added. Subsequently the mixture was raised to room temperature, stirred for 16 hrs and heated at 80° C. for 4 hrs. A part of the reaction solution was withdrawn and determined by $^1$H-NMR, by which it was found to be a mixture of a racemic form/meso form (molar ratio=55/45).

The solvent was distilled off under reduced pressure. The residue was extracted with hexane to obtain 7.8 g (51% yield) of dimethylsilylenebis[2-(2-(5-methyl)-furyl)-4,5-dimethylcyclopentadienyl]zirconium dichloride as yellow powders. Further recrystallization gave 520 mg of the racemic form (purity 99% or more) and 230 mg of the meso form (purity 99% or more). $^1$H-NMR (CDCl$_3$) Racemic form δ: 0.80 (s, 6H), δ: 1.49 (s, 6H), δ: 2.18 (s, 6H), δ: 2.31 (s, 6H), δ: 6.01 (dd, 2H), d: 6.41 (d, 2H), δ: 6.67 (s, 2H)

Meso form δ: 0.69 (s, 3H), δ: 0.99 (s, 3H), δ: 2.00 (s, 6H), δ: 2.19 (s, 6H), δ: 2.27 (s, 6H), δ: 6.12 (dd, 2H), δ: 5.73 (d, 2H), δ: 6.61 (s, 2H).

Polymerization of propylene using dimethylsilylenebis[2-(2-(5-methyl)furyl)-4,5-dimethylcyclopentadienyl]zirconium dichloride A SUS autoclave was charged successively with 1 liter of toluene, a toluene solution of methylaluminoxane (MMAO3A, manufactured by Toso-Aczo Co., Ltd.) (Al/Zr= 10,000) and 3 ml (1.08×10$^{-6}$ mol) of a toluene solution of dimethylsilylenebis[2-(2-(5-methyl)-furyl)-4,5-dimethylcyclopentadienyl]zirconium dichloride, and the mixture was heated to 30° C. Into the autoclave was introduced propylene at a pressure of 0.3 MPaG and a polymerization was carried out for one hour. After the polymerization was completed, a catalyst component was decomposed with 1 liter of hydrochloric acidic methanol. Subsequently, filtration, washing and drying were carried out to obtain 26.8 g of polypropylene.

The analytical values for the resultant polypropylene are shown in Table 1.

Example 9

Synthesis of dimethylsilylenebis[2-(2-(5-t-butyl)furyl)-4,5-dimethylcyclopentadienyl]zirconium dichloride (a1) Synthesis of 1-(2-(5-t-butyl)furyl)-3,4-dimethylcyclopentadiene A 1 l glass reaction vessel was charged with 25.0 g (0.20 mol) of 2-t-butylfuran and 300 ml of THF and cooled to −70° C. on a dry ice/methanol bath. To the mixture were added dropwise 135 ml (0.21 mmol) of an n-butyllithium/hexane solution of 1.54 mol/l. After the addition was completed, the mixture was raised to room temperature and stirred for 16 hrs. The mixture was again cooled to −30° C. on a dry ice/methanol bath and 100 ml of a THF solution containing 22.0 g (0.20 mol) of 3,4-dimethylcyclopenten-1-one were added dropwise. After the addition was completed, the mixture was raised to room temperature and stirred for 16 hrs.

To the reaction solution was added distilled water. This solution was transferred into a separatory funnel and washed three times with brine. Subsequently, the solution was shaken twice with 50 ml of 0.5N hydrochloric acid and washed with brine until it was neutral. Anhydrous sodium sulfate was added and the solution was allowed to stand overnight and dried. Anhydrous sodium sulfate was filtered off and the solvent was distilled off under reduced pressure. Purification of the residue by a silica gel column gave 37.9 g (88% yield) of 1-(2-(5 -t-butyl)furyl)3,4-dimethylcyclopentadiene as a red liquid. The structure was identified by NMR.

(a2) Synthesis of dimethylbis[2-(2-(5-t-butyl)furyl)-4,5-dimethylcyclopentadienyl]silane A 1 l glass reaction vessel was charged with 37.9 g (0.18 mol) of 1-(2-(5-t-butyl)furyl)-3,4-dimethylcyclopentadiene, 1.0 g (0.008 mol) of coprous isocyanate and 300 ml of THF and the mixture was cooled to −70° C. on a dry ice/methanol bath. To the mixture were added dropwise 120 ml (0.18 mol) of an n-butyllithium/hexane solution of 1.54 mol/l. After the addition was completed, the mixture was raised to room temperature and stirred for 3 hrs. The mixture was again cooled to −40° C. on a dry ice/methanol bath and 50 ml of a THF solution containing 11.3 g (0.088 mol) of dimethyl dichlorosilane were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue by a silica gel column and recrystallization with toluene/hexane gave 31.1 g (72% yield) of dimethylbis-[2-(2-(5-t-butyl)furyl)-4,5-dimethylcyclopentadienyl]silane as colorless crystals.

(b) Synthesis of dimethylsilylenebis[2-(2-(5-t-butyl)-furyl)-4,5-dimethylcyclopentadienyl]zirconium dichloride A 500 ml glass reaction vessel was charged with 12.0 g (0.025 mol) of dimethylbis[2-(2-(5-t-butyl)furyl)-4,5-dimethylcyclopentadienyl]silane and 150 ml of THF and the mixture was cooled to −70° C. on a dry ice/methanol bath. To the mixture were added dropwise 33 ml (0.051 mol) of an n-butyllithium/hexane solution of 1.54 mol/l. After the addition was completed, the mixture was raised to room temperature and stirred for 16 hrs. The solvent was distilled off under reduced pressure. To the residue was added 300 ml of toluene and the mixture was cooled to −70° C. on a dry ice/methanol bath. 5.8 g (0.025 mol) of zirconium tetrachloride in a solid state were added. Subsequently the mixture was raised to room temperature and stirred for 3 days. A part of the reaction solution was withdrawn and determined by $^1$H-NMR, by which it was found to be a mixture of a racemic form/meso form (molar ratio=50/50).

The solvent was distilled off under reduced pressure. The residue was extracted with hexane to obtain 12.9 g (81% yield) of dimethylsilylenebis[2-(2-(5-t-butyl)furyl)-4,5-dimethylcyclopentadienyl]zirconium dichloride as yellow powders. Further recrystallization gave 770 mg of the racemic form (purity 99% or more) and 170 mg of the meso form (purity 99% or more). $^1$H-NMR (CDCl$_3$) Racemic form δ: 0.78 (s, 6H), δ: 1.29 (s, 18H), δ: 1.55 (s, 6H), δ: 2.20 (s, 6H), δ: 5.92 (d, 2H), δ: 6.42 (d, 2H), δ: 6.68 (s, 2H)

Meso form δ: 0.57 (s, 3H), δ: 0.99 (s, 3H), δ: 1.24 (s, 18H), δ: 2.01 (s, 6H), δ: 2.28 (s, 6H), δ: 5.68 (d, 2H), δ: 5.99 (d, 2H), δ: 6.63 (s, 2H).

Polymerization of propylene using dimethylsilylenebis[2-(2-(5-t-butyl)furyl)-4,5-dimethylcyclopentadienyl]zirconium dichloride A SUS autoclave was charged successively with 1 liter of toluene, a toluene solution of methylaluminoxane (MMAO3A, manufactured by Toso-Aczo Co., Ltd.) (Al/Zr= 10,000) and 3 ml of a toluene solution of dimethylsilylenebis[2-(2-(5-t-butyl)furyl)-4,5-dimethylcyclopentadienyl]zirconium dichloride (1.02×10$^{-6}$ mol), and the mixture was heated to 30° C. Into the autoclave was introduced propylene at a pressure of 0.3 MPaG and a polymerization was carried out for one hour. After the polymerization was completed, a catalyst component was decomposed with 1 liter of hydrochloric acidic methanol. Subsequently, filtration, washing and drying were carried out to obtain 33.1 g of polypropylene.

The analytical values for the resultant polypropylene are shown in Table 1.

Example 10

Synthesis of dimethylsilylenebis[2-(2-(5-trimethylsilyl)-furyl)-4,5-dimethylcyclopentadienyl] zirconium dichloride (a1) Synthesis of 1-(2-(5-trimethylsilyl)furyl)-3,4-dimethylcyclopentadiene A 1 l glass reaction vessel was charged with 23.0 g (0.16 mol) of 2-trimethylsilylfuran and 200 ml of THF and the mixture was cooled to −70° C. on a dry ice/methanol bath. To the mixture were added dropwise 100 ml (0.16 mmol) of an n-butyllithium/hexane solution of 1.57 mol/l. After the addition was completed, the mixture was raised to room temperature and stirred for 16 hrs. The mixture was again cooled to −30° C. on a dry ice/methanol bath and 100 ml of a THF solution containing 17.3 g (0.16 mol) of 3,4-dimethylcyclopenten-1-one were added dropwise. After the addition was completed, the mixture was raised to room temperature and stirred for 16 hrs.

To the reaction solution was added distilled water. This reaction solution was transferred into a separatory funnel and washed three times with brine. This solution was then shaken twice with 50 ml of 0.5N hydrochloric acid and washed with brine until it was neutral. Anhydrous sodium sulfate was added and the solution was allowed to stand overnight and dried. Anhydrous sodium sulfate was filtered off and the solvent was distilled off under reduced pressure. Purification of the residue by a silica gel column gave 31.5 g (85% yield) of 1-(2-(5-trimethylsilyl)furyl)-3,4-dimethylcyclopentadiene as a yellow liquid. The structure was identified by NMR.

(a2) Synthesis of dimethylbis[2-(2-(5-trimethylsilyl)furyl)4,5-dimethylcyclopentadienyl]silane A 1 l glass reaction vessel was charged with 31.5 g (0.14 mol) of 1-(2-(5-trimethylsilyl)furyl)-3,4- dimethylcyclopentadiene, 1.0 g (0.008 mol) of coprous isocyanate and 300 ml of THF and the mixture was cooled to −70° C. on a dry ice/methanol bath. To the mixture was added dropwise 90 ml (0.14 mmol) of an n-butyllithium/hexane solution of 1.57 mol/l. After the addition was completed, the mixture was raised to room temperature and stirred for 16 hrs. The mixture was again cooled to −30° C. on a dry ice/methanol bath and 50 ml of a THF solution containing 8.7 g (0.067 mol) of dimethyl dichlorosilane were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue by a silica gel column and recrystallization with toluene/hexane gave 24.7 g (70% yield) of dimethylbis[2-(2-(5-trimethylsilyl)furyl)-4,5-dimethylcyclopentadienyl]silane as pale yellow crystals. Synthesis of dimethylsilylenebis[2-(2-(5-trimethylsilyl)furyl)-4,5-dimethylcyclopentadienyl]zirconium dichloride A 500 ml glass reaction vessel was charged with 12.0 g (0.023 mol) of dimethylbis[2-(2-(5-trimethylsilyl)furyl)-4,5-dimethyl-cyclopentadienyl]silane and 150 ml of THF and cooled to −70° C. on a dry ice/methanol bath. To the mixture was added dropwise 31 ml (0.049 mmol) of an n-butyllithium/hexane solution of 1.57 mol/l. After the addition was completed, the mixture was raised to room temperature and stirred for 16 hrs. The solvent was distilled off. To the residue were added 300 ml of toluene and the mixture was cooled to −70° C. on a dry ice/methanol bath. 5.4 g (0.023 mol) of zirconium tetrachloride in a solid state was added. After the addition was completed, the mixture was raised to room temperature and stirred for 3 days. A part of the reaction solution was withdrawn and determined by $^1$H-NMR, by which it was found to be a mixture of a racemic form/meso form (molar ratio=75/25).

The solvent was distilled off under reduced pressure and the residue was extracted with hexane to afford 12.0 g (76% yield) of dimethylsilylenebis[2-(2-(5-trymethylsilyl)furyl)-4,5-dimethylcyclopentadienyl]zirconium dichloride as yellow powders. Further recrystallization gave 2.0 g of the racemic form (purity 99% or more).

$^1$H-NMR (CDCl$_3$) Racemic form δ: 0.28 (s, 18H), d: 0.79 (s, 6H), δ: 1.45 (s, 6H), δ: 2.18 (s, 6H), δ: 6.56 (d, 2H), δ: 6.61 (d, 2H), δ: 6.71 (s, 2H)

Meso form δ: 0.23 (s, 18H), δ: 0.47 (s, 3H), δ: 1.00 (s, 3H), δ: 2.02 (s, 6H), δ: 2.28 (s, 6H), δ: 6.10 (d, 2H), δ: 6.30 (d, 2H),o: 6.64 (s, 2H).

Polymerization of propylene using dimethylsilylenebis[2-(2-(5-trimethylsilyl)furyl)-4,5-dimethylcyclopentadienyl]zirconium dichloride A SUS autoclave was charged successively with 1 liter of toluene, a toluene solution of methylaluminoxane (MMAO3A, manufactured by Toso-Aczo Co., Ltd.) (Al/Zr= 10,000) and 3 ml (0.97×10$^{-6}$ mol) of a toluene solution of dimethylsilylene-bis[2-(2-(5-trimethylsilyl)furyl)-4,5-dimethylcyclopentadienyl]-zirconium dichloride, and the mixture was heated to 30° C. Into the autoclave was introduced propylene at a pressure of 0.3 MPaG and a polymerization was carried out for one hour. After the polymerization was completed, a catalyst component was decomposed with 1 liter of hydrochloric acidic methanol. Subsequently, filtration, washing and drying were carried out to obtain 39.3 g of polypropylene.

The analytical values for the resultant polypropylene are shown in Table 1.

Example 11

Synthesis of dimethylsilylenebis[2-(2-(4,5-dimethyl)furyl)4,5-dimethylcyclopentadienyl]zirconium dichloride (a1) Synthesis of 1-(2-(4,5-dimethyl)furyl)-3,4-dimethylcyclopentadiene A 1 l glass reaction vessel was charged with 17.0 g (0.18 mol) of 2,3-dimethylfuran and 300 ml of THF and cooled to −70° C. on a dry ice/methanol bath. To the mixture were added dropwise 115 ml (0.18 mol) of an n-butyllithium/hexane solution of 1.54 mol/l. After the addition was completed, the mixture was raised to room temperature and stirred for 16 hrs. The mixture was again cooled to −30° C. on a dry ice/methanol bath and 100 ml of a THF solution containing 19.5 g (0.18 mol) of 3,4-dimethylcyclopenten-1-one were added dropwise. After the addition was completed, the mixture was raised to room temperature and stirred for 16 hrs.

To the reaction solution was added distilled water. This reaction solution was transferred into a separatory funnel and washed three times with brine. This solution was then shaken twice with 50 ml of 0.5N hydrochloric acid and washed with brine until it was neutral. Anhydrous sodium sulfate was added and the solution was allowed to stand overnight and dried. Anhydrous sodium sulfate was filtered off and the solvent was distilled off under reduced pressure. Purification of the residue by a silica gel column gave 30.6 g (92% yield) of 1-(2-(4,5-dimethyl)furyl)-3,4-dimethylcyclopentadiene as orange crystals. The structure was identified by NMR.

(a2) Synthesis of dimethylbis[2-(2-(4,5-dimethyl)furyl)-4,5-dimethylcyclopentadienyl]silane A 1 l glass reaction vessel was charged with 30.0 g (0.16 mol) of 1-(2-(4,5-dimethyl)furyl)-3,4-dimethylcyclopentadiene, 1.0 g (0.008 mol) of coprous isocyanate and 300 ml of THF and the mixture was cooled to −70° C. on a dry ice/methanol bath. To the mixture were added dropwise 108 ml (0.16 mol) of an n-butyllithium/hexane solution of 1.57 mol/l. After the addition was completed, the mixture was raised to room temperature and stirred for 16 hrs. The mixture was again cooled to −30° C. on a dry ice/methanol bath and 50 ml of a THF solution containing 10.3 g (0.080 mol) of dimethyl-dichlorosilane were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue by a silica gel column and recrystallization with toluene/hexane gave 21.3 g (62% yield) of dimethylbis[2-(2-(4,5-dimethyl)furyl)-4,5-dimethylcyclopentadienyl]silane as pale yellow crystals.

(b) Synthesis of dimethylsilylenebis[2-(2-(4,5-dimethyl)furyl)-4,5-dimethylcyclopentadienyl]zirconium dichloride A 500 ml glass reaction vessel was charged with 12.0 g (0.025 mol) of dimethylbis[2-(2-(4,5-dimethyl)furyl)4,5-dimethylcyclopentadienyl]silane and 150 ml of THF and the mixture was cooled to −70° C. on a dry ice/methanol bath. To the mixture were added dropwise 33 ml (0.051 mmol) of an n-butyllithium/ hexane solution of 1.54 mol/l. After the addition was completed, the mixture was raised to room temperature and stirred for 16 hrs. The solvent was distilled off. To the residue were added 300 ml of toluene is and the mixture was cooled to −70° C. on a dry ice/methanol bath. 5.8 g (0.025 mol) of zirconium tetrachloride in a solid state was added. Subsequently, the mixture was raised to room temperature and stirred for 3 days. A part of the reaction solution was withdrawn and determined by $^1$H-NMR, by which it was found to be a mixture of a racemic form/meso form (molar ratio=62/38).

The solvent was distilled off under reduced pressure and the residue was extracted with hexane to afford 12.9 g (62% yield) of dimethylsilylenebis[2-(2-(4,5-dimethyl)furyl)-4,5-dimethylcyclopentadienyl]zirconium dichloride as yellow powders. Further recrystallization gave 770 mg of the racemic form (purity 99% or more) and 170 mg of the meso form (purity 99% or more).

$^1$H-NMR (CDCl$_3$) Racemic form δ: 0.80 (s, 6H), δ: 1.49 (s, 6H), δ: 1.92 (s, 6H), δ: 1.99 (s, 6H), δ: 2.18 (s, 6H), δ: 6.30 (s, 2H), δ: 6.64 (s, 2H)

Meso form δ: 0.72 (s, 3H), δ: 0.98 (s, 3H), d: 1.81 (s, 6H), δ: 2.10 (s, 6H), δ: 2.22 (s, 6H), δ: 2.26 (s, 6H), δ: 5.88 (s, 2H),δ: 6.58 (s, 2H).

Polymerization of propylene using dimethylsilylenebis[2-(2-(4,5-dimethyl)furyl)-4,5-dimethylcyclopentadienyl]zirconium dichloride A SUS autoclave was charged successively with 1 liter of toluene, a toluene solution of methylaluminoxane (MMAO3A, manufactured by Toso-Aczo Co., Ltd.) (Al/Zr= 10,000) and 3 ml (1.05×10$^{-6}$ mol) of a toluene solution of dimethylsilylenebis[2-(2-(4,5-dimethyl)furyl)-4,5-dimethylcyclopentadienyl]zirconium dichloride, and the mixture was heated to 30° C. Into the autoclave was introduced propylene 20 at a pressure of 0.3 MPaG and a polymerization was carried out for one hour. After the polymerization was completed, a catalyst component was decomposed with 1 liter of hydrochloric acidic methanol. Subsequently, filtration, washing and drying were carried out to obtain 13.3 g of polypropylene.

The analytical values for the resultant polypropylene are shown in Table 1.

Example 12

Synthesis of dimethylsilylenebis[2-(2-benzofuryl)-4,5-dimethylcyclopentadienyl]zirconium dichloride (a1) Synthesis of 1-(2-benzofuryl)-3,4-dimethylcyclopentadiene A 1 l glass reaction vessel was charged with 34.4 g (0.29 mol) of benzofuran and 400 ml of THF and the mixture was cooled to −70° C. on a dry ice/methanol bath. To the mixture were added dropwise 180 ml (0.28 mol) of an n-butyllithium/hexane solution of 1.53 mol/l. After the addition was completed, the mixture was raised to room temperature and stirred for 16 hrs. The mixture was again cooled to −30° C. on a dry ice/methanol bath and 100 ml of a THF solution containing 30.0 g (0.27 mol) of 3,4-dimethylcyclopenten-1-one were added dropwise. After the addition was completed, the mixture was raised to room temperature and stirred for 16 hrs.

To the reaction solution was added distilled water. This reaction solution was transferred into a separatory funnel and washed three times with brine. This solution was then shaken twice with 30 ml of 2N hydrochloric acid and washed with brine until it was neutral. Anhydrous sodium sulfate was added and the reaction solution was allowed to stand overnight and dried. Anhydrous sodium sulfate was filtered off and the solvent was distilled off under reduced pressure. Purification of the residue by a silica gel column gave 54.3 g (95% yield) of 1-(2 -benzofuryl)-3,4-dimethylcyclopentadiene as pale yellow crystals. The structure was identified by NMR.

(a2) Synthesis of dimethylbis[2-(2-benzofuryl)-4,5-dimethylcyclopentadienyl]silane A 1 l glass reaction vessel was charged with 54.3 g (0.26 mol) of 1-(2-benzofuryl)-3,4-dimethylcyclopentadiene, 1.5 g (0.012 mol) of coprous isocyanate and 400 ml of THF and the mixture was cooled to −70° C. on a dry ice/methanol bath. To the mixture were added dropwise 170 ml (0.26 mol) of an n-butyllithium/hexane solution of 1.53 mol/l. After the addition was completed, the mixture was raised to room temperature and stirred for 16 hrs. The mixture was again cooled to −70° C. on a dry ice/methanol bath and 100 ml of a THF solution containing 16.6 g (0.13 mol) of dimethyl dichlorosilane were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue by a silica gel column and recrystallization with toluene/hexane gave 19 g (46% yield) of dimethylbis[2 -(2-benzofuryl)-4,5-dimethylcyclopentadienyl]silane as pale yellow crystals.

(b) Synthesis of dimethylsilylenebis[2-(2-benzofuryl)-4,5-dimethylcyclopentadienyl]zirconium dichloride A 500 ml glass reaction vessel was charged with 15.0 g (0.031 mol) of dimethylbis[2-(2-benzofuryl)-4,5-dimethylcyclopentadienyl]silane and 300 ml of THF and the mixture was cooled to −70° C. on a dry ice/methanol bath. To the mixture were added dropwise 41 ml (0.063 mol) of an n-butyllithium/hexane solution of 1.53 mol/l. After the addition was completed, the mixture was raised to room temperature and stirred for 16 hrs. The solvent was distilled off. To the residue were added 400 ml of toluene and the mixture was cooled to −70° C. on a dry ice/methanol bath. 7.2 g (0.031 mol) of zirconium tetrachloride in a solid state was added. Subsequently, the mixture was raised to room temperature and stirred for 3 days. A part of the reaction solution was withdrawn and determined by $^1$H-NMR, by which it was found to be a mixture of a racemic form/meso form (molar ratio=40/60).

The solvent was distilled off under reduced pressure and the residue was extracted with hexane to afford 6.0 g (30% yield) of dimethylsilylenebis[2-(2-benzofuryl)-4,5-dimethylcyclopentadienyl]zirconium dichloride as yellow powders. Further recrystallization gave 510 mg of the racemic form (purity 99% or more).

$^1$H-NMR (CDCl$_3$) Racemic form δ: 0.92 (s, 6H), δ: 1.46 (s, 6H), δ: 2.22 (s, 6H), δ: 6.89 (s, 2H), δ: 6.97 (s, 2H), δ: 7.22–7.31 (m, 4H), δ: 6.96 (d, 2H), δ: 7.57 (d, 2H)

Meso form δ: 0.94 (s, 3H), δ: 1.08 (s, 3H), δ: 2.08 (s, 6H), δ: 2.34 (s, 6H), δ: 6.37 (s, 2H), δ: 6.82 (s, 2H), δ: 6.79–6.86 (m, 4H), δ: 6.93–6.96 (m, 2H), δ: 7.03 (d, 2H).

Polymerization of propylene using dimethylsilylenebis[2-(2-benzofuryl)-4,5-dimethylcyclopentadienyl]zirconium dichloride A SUS autoclave was charged successively with 1 liter of toluene, a toluene solution of methylaluminoxane (MMAO3A, manufactured by Toso-Aczo Co., Ltd.) (Al/Zr= 10,000) and 3 ml ($1.55 \times 10^{-6}$ mol) of a toluene solution of dimethylsilylenebis(2-(2-benzofuryl)-4,5-dimethylcyclopentadienyl]zirconium dichloride, and the mixture was heated to 30° C. Into the autoclave was introduced propylene at a pressure of 0.3 MPaG and a polymerization was carried out for one hour. After the polymerization was completed, a catalyst component was decomposed with 1 liter of hydrochloric acidic methanol. Subsequently, filtration, washing and drying were carried out to obtain 14.3 g of polypropylene.

The analytical values for the resultant polypropylene are shown in Table 1.

Example 12

Synthesis of dimethylsilylenebis[2-(2-thienyl)-indenyl]zirconium dichloride (a1) Synthesis of 2-(2-thienyl)-indene A 500 ml glass reaction vessel was charged with 12.8 g (0.15 mol) of thiophene and 200 ml of THF and the mixture was cooled to −70° C. on a dry ice/methanol bath. To the mixture were added dropwise 100 ml (0.15 mol) of an n-butyllithium/hexane solution of 1.53 mol/l. After the addition was completed, the mixture was raised to room temperature and stirred for 3 hrs. The mixture was again cooled to −20° C. on a dry ice/methanol bath and 200 ml of a THF solution containing 20.0 g (0.15 mol) of 2-indanone were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the reaction solution was allowed to stand overnight and dried. Anhydrous sodium sulfate was filtered off and the solvent was distilled off under reduced pressure. To the residue were added 200 ml of toluene and 0.5 g of P-toluenesulfonic acid. The mixture was heated under reflux while removing water that was distilling out. The reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue by a silica gel column gave 3.2 g (25% yield) of 2-(2-thienyl)-indene as pale yellow-green crystals. The structure was identified by NMR.

(a2) Synthesis of dimethylbis[2-(2-thienyl)-indenyl]silane

A 200 ml glass reaction vessel was charged with 10.0 g (0.051 mol) of 2-(2-thienyl)-indene, 0.87 g (0.0072 mol) of coprous cyanide and 210 ml of THF and the mixture was cooled to −70° C. on a dry ice/methanol bath. To the mixture were added dropwise 36 ml (0.057 mol) of an n-butyllithium/hexane solution of 1.57 mol/l. After the addition was completed, the mixture was raised to room temperature and stirred for 16 hrs. The mixture was again cooled to −70° C. on a dry ice/methanol bath and 140 ml of a THF solution containing 3.7 g (0.028 mol) of dimethyl dichlorosilane were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the reaction solution was allowed to stand overnight and dried. Anhydrous sodium sulfate was filtered off and the solvent was distilled off under reduced pressure. Purification of the residue by a silica gel column gave 7.3 g (64% yield) of dimethylbis[2-(2-thienyl)-indenyl]silane as pale yellow-green crystals.

(b) Synthesis of dimethylsilylenebis[2-(2-thienyl)-indenyl]zirconium dichloride

A 100 ml glass reaction vessel was charged with 12.4 g (0.027 mol) of dimethylbis[2-(2-thienyl)-indenyl]-silane and 30 ml of THF and the mixture was cooled to −70° C. on a dry ice/methanol bath. To the mixture were added dropwise 35 ml (0.055 mol) of an n-butyllithium/hexane solution of 1.57 mol/l. After the addition was completed, the mixture was raised to room temperature and stirred for 16 hrs. The solvent was distilled off. To the residue were added 400 ml of toluene and the mixture was cooled to −70° C. on a dry ice/methanol bath. 6.3 g (0.027 mol) of zirconium tetrachloride were added. Subsequently, the mixture was raised to room temperature and stirred for 16 hrs. A part of the reaction solution was withdrawn and determined by $^1$H-NMR, by which it was found to be a mixture of a racemic form/meso form (molar ratio=75/25).

The solvent was distilled off under reduced pressure and the residue was extracted with toluene to afford 100 mg (0.6% yield) of the racemic form (purity 99% or more).

$^1$H-NMR (CDCl$_3$) Racemic form δ: 1.03 (s, 6H), δ: 7.04 (s, 2H), δ: 6.80–7.63 (m, 14H). Polymerization of propylene using dimethylsilylenebis[2-(2-thienyl)-indenyl] zirconium dichiloride A SUS autoclave was charged successively with 1 liter of toluene, a toluene solution of methylaluminoxane (MMAO3A, manufactured by Toso-Aczo Co., Ltd.) (Al/Zr= 10,000) and 3 ml ($2.71 \times 10^{-6}$ mol) of a toluene solution of dimethylsilylenebis[2-(2-thienyl)-indenyl]zirconium dichloride, and the mixture was heated to 30° C. Into the autoclave was introduced propylene at a pressure of 0.3 MPaG and a polymerization was carried out for one hour. After the polymerization was completed, a catalyst component was decomposed with 1 liter of hydrochloric acidic methanol. Subsequently, filtration, washing and drying were carried out to obtain 1.88 g of polypropylene.

The analytical values for the resultant polypropylene are shown in Table 1.

In Table 1, "Amount of racemic form" indicates the amount of a racemic form in the metallocene complex used as the catalyst in the polymerization of propylene. In case of a mixture of a racemic/meso form being used as the catalyst, the amount of the mixture used was indicated in parenthesis. The amount of a racemic form in the mixture was calculated from a molar ratio of a racemic/meso form determined by NMR for the mixture, and the calculated value was indicated in the table. In case of propylene being polymerized using a mixture of a racemic/meso form as the catalyst, the amount of an isotactic polypropylene component obtained by removing an atactic polypropylene component from the polymerization product was indicated as "yield" in the table. "Activity" was calculated from the values shown in "amount of racemic form" and "yield".

TABLE 1

Analytical Values for Polypropylene

| Metallocene compound of Example No. | Amount of racemic form × 10⁻⁶ mol | Yield g | Activity kg-pp/ mmol-M-h | Mw × 10⁴ | Mw/Mn | Tm °C. | Mmmm |
|---|---|---|---|---|---|---|---|
| 1 Me$_2$Si[3-(2-Furyl)-2,5-Me$_2$—Cp]$_2$ZrCl$_2$ | 0.65 (1.35) | 43.1 | 67 | 13.3 | 1.77 | 153.6 | 0.941 |
| 2 Me$_2$Si[2-(2-Furyl)-3,5-Me$_2$—Cp]$_2$ZrCl$_2$ | 0.62 | 42.7 | 69 | 48.3 | 1.91 | 156.9 | 0.956 |
| 3 Me$_2$Si[2-(2-Furyl)-4,5-Me$_2$—Cp]$_2$ZrCl$_2$ | 0.55 | 20.9 | 38 | 47.8 | 2.01 | 154.0 | 0.943 |
| 4 Me$_2$Si[3-(2-Thienyl)-2,5-Me$_2$—Cp]$_2$ZrCl$_2$ | 0.97 (1.61) | 33.6 | 35 | 23.8 | 1.77 | 148.9 | 0.938 |
| 5 Me$_2$Si[2-(2-Furyl)-Indenyl]ZrCl$_2$ | 0.30 | 4.6 | 15 | 128 | 2.30 | 148.0 | 0.925 |
| 7 Me$_2$Si(2-2-Thienyl)-4,5-Me$_2$—Cp)$_2$ZrCl$_2$ | 1.05 | 1.88 | 1.8 | 9.75 | 1.83 | 77.1 | 0.460 |
| 8 Me$_2$Si(2-(2-(5-Me)-Furyl)-4,5-Me$_2$—Cp)$_2$ZrCl$_2$ | 1.08 | 26.8 | 25 | 63.5 | 2.02 | 154.8 | 0.954 |
| 9 Me$_2$Si(2-(2-(5-t-Bu)-Furyl)-4,5-Me$_2$—Cp)$_2$ZrCl$_2$ | 1.02 | 33.1 | 32 | 58.5 | 2.20 | 152.0 | 0.940 |
| 10 Me$_2$Si(2-(2-(5-TMS)-Furyl)-4,5-Me$_2$—Cp)$_2$ZrCl$_2$ | 0.97 | 39.3 | 40 | 63.3 | 1.91 | 151.5 | 0.941 |
| 11 Me$_2$Si(2-(2-(4,5-Me$_2$)-Furyl)-4,5-Me$_2$—Cp)$_2$ZrCl$_2$ | 1.05 | 13.3 | 13 | 55.8 | 2.06 | 155.9 | 0.959 |
| 12 Me$_2$Si(2-(2-BenzoFuryl)-4,5-Me$_2$—Cp)$_2$ZrCl$_2$ | 1.55 | 14.3 | 9.2 | 37.6 | 1.83 | 151.7 | 0.935 |
| 13 Me$_2$Si(2-(2-Thienyl)-Ind)$_2$ZrCl$_2$ | 2.71 | 10.7 | 4.0 | 42.1 | 1.91 | 136.7 | 0.866 |

TABLE 2

| | | | CA¹: Cyclopentadienyl | | | CA²: Cyclopentadienyl | | | |
|---|---|---|---|---|---|---|---|---|---|
| No. | M | X | Ra | R¹ | p + m | Ra | R¹ | q + n | Y |
| 1 | Zr | Cl | 2-(2-Fu) | — | 1 | 2-(2-Fu) | — | 1 | —CH$_2$— |
| 2 | Zr | Cl | 2-(2-Fu) | — | 1 | 2-(2-Fu) | — | 1 | —C(Me)$_2$— |
| 3 | Zr | Cl | 2-(2-Fu) | 5-Me | 2 | 2-(2-Fu) | 5-Me | 2 | —C(Me)$_2$— |
| 4 | Zr | Cl | 2-(2-Fu) | 4-Me | 2 | 2-(2-Fu) | 4-Me | 2 | —C(Me)$_2$— |
| 5 | Zr | Cl | 2-(2-Fu) | 4-OMe | 2 | 2-(2-Fu) | 4-OMe | 2 | —C(Me)$_2$— |
| 6 | Zr | Cl | 2-(2-Fu) | 4-OPh | 2 | 2-(2-Fu) | 4-OPh | 2 | —C(Me)$_2$— |
| 7 | Zr | Cl | 2-(2-Fu) | 4-Bzl | 2 | 2-(2-Fu) | 4-Bzl | 2 | —C(Me)$_2$— |
| 8 | Zr | Cl | 2-(2-Fu) | 4-Tol | 2 | 2-(2-Fu) | 4-Tol | 2 | —C(Me)$_2$— |

TABLE 2-continued

| | | | CA¹: Cyclopentadienyl | | | CA²: Cyclopentadienyl | | | |
|---|---|---|---|---|---|---|---|---|---|
| No. | M | X | Ra | R¹ | p + m | Ra | R¹ | q + n | Y |
| 9 | Zr | Cl | 2-(2-Fu) | 4-OBzl | 2 | 2-(2-Fu) | 4-OBzl | 2 | —C(Me)$_2$— |
| 10 | Zr | Cl | 2-(2-Fu) | 4-TMS | 2 | 2-(2-Fu) | 4-TMS | 2 | —C(Me)$_2$— |
| 11 | Zr | Cl | 2-(2-Fu) | 4-(1-Pyr) | 2 | 2-(2-Fu) | 4-(1-Pyr) | 2 | —C(Me)$_2$— |
| 12 | Zr | Cl | 2-(2-Fu) | 4-(1-Indo) | 2 | 2-(2-Fu) | 4-(1-Indo) | 2 | —C(Me)$_2$— |
| 13 | Zr | Cl | 2-(2-Fu) | 3-Me | 2 | 2-(2-Fu) | 3-Me | 2 | —C(Me)$_2$— |
| 14 | Zr | Cl | 2-(2-Fu) | 3-Me, 5-Me | 3 | 2-(2-Fu) | 3-Me, 5-Me | 3 | —C(Me)$_2$— |
| 15 | Zr | Cl | 2-(2-Fu) | 4-Me, 5-Me | 3 | 2-(2-Fu) | 4-Me, 5-Me | 3 | —C(Me)$_2$— |
| 16 | Zr | Cl | 2-(2-Fu) | 4-Et, 5-Me | 3 | 2-(2-Fu) | 4-Et, 5-Me | 3 | —C(Me)$_2$— |
| 17 | Zr | Cl | 2-(2-Fu) | 4-(i-Pr), 5-Me | 3 | 2-(2-Fu) | 4-(i-Pr), 5-Me | 3 | —C(Me)$_2$— |
| 18 | Zr | Cl | 2-(2-Fu) | 4-(t-Bu), 5-Me | 3 | 2-(2-Fu) | 4-(t-Bu), 5-Me | 3 | —C(Me)$_2$— |
| 19 | Zr | Cl | 2-(2-Fu) | 4-Ph, 5-Me | 3 | 2-(2-Fu) | 4-Ph, 5-Me | 3 | —C(Me)$_2$— |
| 20 | Zr | Cl | 2-(2-Fu) | 3-Ph, 5-Me | 3 | 2-(2-Fu) | 3-Ph, 5-Me | 3 | —C(Me)$_2$— |
| 21 | Zr | Cl | 2-(2-Fu) | 4-Me, 5-Me | 3 | 2-(2-Fu) | 4-Me, 5-Me | 3 | —C(Et)$_2$— |
| 22 | Zr | Cl | 2-(2-Fu) | 4-Me, 5-Me | 3 | 2-(2-Fu) | 4-Me, 5-Me | 3 | —C(Ph)$_2$— |
| 23 | Zr | Me | 2-(2-Fu) | 4-Me, 5-Me | 3 | 2-(2-Fu) | 4-Me, 5-Me | 3 | —C(Me)$_2$— |
| 24 | Zr | Bzl | 2-(2-Fu) | 4-Me, 5-Me | 3 | 2-(2-Fu) | 4-Me, 5-Me | 3 | —C(Me)$_2$— |
| 25 | Hf | Cl | 2-(2-Fu) | 4-Me, 5-Me | 3 | 2-(2-Fu) | 4-Me, 5-Me | 3 | —C(Me)$_2$— |
| 26 | Ti | Cl | 2-(2-Fu) | 4-Me, 5-Me | 3 | 2-(2-Fu) | 4-Me, 5-Me | 3 | —C(Me)$_2$— |
| 27 | Hf | Cl | 2-(2-Fu) | 3-Me, 5-Me | 3 | 2-(2-Fu) | 3-Me, 5-Me | 3 | —C(Me)$_2$— |
| 28 | Ti | Cl | 2-(2-Fu) | 3-Me, 5-Me | 3 | 2-(2-Fu) | 3-Me, 5-Me | 3 | —C(Me)$_2$— |
| 29 | Zr | Cl | 2-(3-Fu) | 4-Me, 5-Me | 3 | 2-(3-Fu) | 4-Me, 5-Me | 3 | —C(Me)$_2$— |
| 30 | Zr | Cl | 2-(3-Fu) | 3-Me, 5-Me | 3 | 2-(3-Fu) | 3-Me, 5-Me | 3 | —C(Me)$_2$— |
| 31 | Zr | Cl | 2-[2-(3-Me—Fu)] | 4-Me, 5-Me | 3 | 2-[2-(3-Me—Fu)] | 4-Me, 5-Me | 3 | —C(Me)$_2$— |
| 32 | Zr | Cl | 2-[2-(3-Me—Fu)] | 3-Me, 5-Me | 3 | 2-[2-(3-Me—Fu)] | 3-Me, 5-Me | 3 | —C(Me)$_2$— |
| 33 | Zr | Cl | 2-(2-Thie) | 4-Me, 5-Me | 3 | 2-(2-Thie) | 4-Me, 5-Me | 3 | —C(Me)$_2$— |
| 34 | Zr | Cl | 2-(2-Thie) | 3-Me, 5-Me | 3 | 2-(2-Thie) | 3-Me, 5-Me | 3 | —C(Me)$_2$— |
| 35 | Zr | Cl | 2-(2-Py) | 4-Me, 5-Me | 3 | 2-(2-Py) | 4-Me, 5-Me | 3 | —C(Me)$_2$— |
| 36 | Zr | Cl | 2-(2-Py) | 3-Me, 5-Me | 3 | 2-(2-Py) | 3-Me, 5-Me | 3 | —C(Me)$_2$— |
| 37 | Zr | Cl | 2-(2-BzFu) | 4-Me, 5-Me | 3 | 2-(2-BzFu) | 4-Me, 5-Me | 3 | —C(Me)$_2$— |
| 38 | Zr | Cl | 2-(2-BzFu) | 3-Me, 5-Me | 3 | 2-(2-BzFu) | 3-Me, 5-Me | 3 | —C(Me)$_2$— |
| 39 | Zr | Cl | 2-[2-(1-Me—Pyr)] | 4-Me, 5-Me | 3 | 2-[2-(1-Me—Pyr)] | 4-Me, 5-Me | 3 | —C(Me)$_2$— |
| 40 | Zr | Cl | 2-[2-(1-Me—Pyr)] | 3-Me, 5-Me | 3 | 2-[2-(1-Me—Pyr)] | 3-Me, 5-Me | 3 | —C(Me)$_2$— |

TABLE 3

| | | | CA¹: Cyclopentadienyl | | | CA²: Cyclopentadienyl | | | |
|---|---|---|---|---|---|---|---|---|---|
| No. | M | X | Ra | R¹ | p + m | Ra | R¹ | q + n | Y |
| 41 | Zr | Cl | 2-(2-Fu) | — | 1 | 2-(2-Fu) | — | 1 | —CH$_2$CH$_2$— |
| 42 | Zr | Cl | 2-(2-Fu) | — | 1 | 2-(2-Fu) | — | 1 | —C$_2$(Me)$_4$— |
| 43 | Zr | Cl | 2-(2-Fu) | 5-Me | 2 | 2-(2-Fu) | 5-Me | 2 | —C$_2$(Me)$_4$— |
| 44 | Zr | Cl | 2-(2-Fu) | 4-Me | 2 | 2-(2-Fu) | 4-Me | 2 | —C$_2$(Me)$_4$— |
| 45 | Zr | Cl | 2-(2-Fu) | 4-OMe | 2 | 2-(2-Fu) | 4-OMe | 2 | —C$_2$(Me)$_4$— |
| 46 | Zr | Cl | 2-(2-Fu) | 4-OPh | 2 | 2-(2-Fu) | 4-OPh | 2 | —C$_2$(Me)$_4$— |
| 47 | Zr | Cl | 2-(2-Fu) | 4-Bzl | 2 | 2-(2-Fu) | 4-Bzl | 2 | —C$_2$(Me)$_4$— |
| 48 | Zr | Cl | 2-(2-Fu) | 4-Tol | 2 | 2-(2-Fu) | 4-Tol | 2 | —C$_2$(Me)$_4$— |
| 49 | Zr | Cl | 2-(2-Fu) | 4-OBzl | 2 | 2-(2-Fu) | 4-OBzl | 2 | —C$_2$(Me)$_4$— |
| 50 | Zr | Cl | 2-(2-Fu) | 4-TMS | 2 | 2-(2-Fu) | 4-TMS | 2 | —C$_2$(Me)$_4$— |
| 51 | Zr | Cl | 2-(2-Fu) | 4-(1-Pyr) | 2 | 2-(2-Fu) | 4-(1-Pyr) | 2 | —C$_2$(Me)$_4$— |
| 52 | Zr | Cl | 2-(2-Fu) | 4-(1-Indo) | 2 | 2-(2-Fu) | 4-(1-Indo) | 2 | —C$_2$(Me)$_4$— |
| 53 | Zr | Cl | 2-(2-Fu) | 3-Me | 2 | 2-(2-Fu) | 3-Me | 2 | —C$_2$(Me)$_4$— |
| 54 | Zr | Cl | 2-(2-Fu) | 3-Me, 5-Me | 3 | 2-(2-Fu) | 3-Me, 5-Me | 3 | —C$_2$(Me)$_4$— |
| 55 | Zr | Cl | 2-(2-Fu) | 4-Me, 5-Me | 3 | 2-(2-Fu) | 4-Me, 5-Me | 3 | —C$_2$(Me)$_4$— |
| 56 | Zr | Cl | 2-(2-Fu) | 4-Et, 5-Me | 3 | 2-(2-Fu) | 4-Et, 5-Me | 3 | —C$_2$(Me)$_4$— |
| 57 | Zr | Cl | 2-(2-Fu) | 4-(i-Pr), 5-Me | 3 | 2-(2-Fu) | 4-(i-Pr), 5-Me | 3 | —C$_2$(Me)$_4$— |
| 58 | Zr | Cl | 2-(2-Fu) | 4-(t-Bu), 5-Me | 3 | 2-(2-Fu) | 4-(t-Bu), 5-Me | 3 | —C$_2$(Me)$_4$— |
| 59 | Zr | Cl | 2-(2-Fu) | 4-Ph, 5-Me | 3 | 2-(2-Fu) | 4-Ph, 5-Me | 3 | —C$_2$(Me)$_4$— |
| 60 | Zr | Cl | 2-(2-Fu) | 3-Ph, 5-Me | 3 | 2-(2-Fu) | 3-Ph, 5-Me | 3 | —C$_2$(Me)$_4$— |
| 61 | Zr | Cl | 2-(2-Fu) | 4-Me, 5-Me | 3 | 2-(2-Fu) | 4-Me, 5-Me | 3 | —C$_2$(Et)$_4$— |
| 62 | Zr | Cl | 2-(2-Fu) | 4-Me, 5-Me | 3 | 2-(2-Fu) | 4-Me, 5-Me | 3 | —C$_2$(Ph)$_4$— |
| 63 | Zr | Me | 2-(2-Fu) | 4-Me, 5-Me | 3 | 2-(2-Fu) | 4-Me, 5-Me | 3 | —C$_2$(Me)$_4$— |
| 64 | Zr | Bzl | 2-(2-Fu) | 4-Me, 5-Me | 3 | 2-(2-Fu) | 4-Me, 5-Me | 3 | —C$_2$(Me)$_4$— |
| 65 | Hf | Cl | 2-(2-Fu) | 4-Me, 5-Me | 3 | 2-(2-Fu) | 4-Me, 5-Me | 3 | —C$_2$(Me)$_4$— |
| 66 | Ti | Cl | 2-(2-Fu) | 4-Me, 5-Me | 3 | 2-(2-Fu) | 4-Me, 5-Me | 3 | —C$_2$(Me)$_4$— |
| 67 | Hf | Cl | 2-(2-Fu) | 3-Me, 5-Me | 3 | 2-(2-Fu) | 3-Me, 5-Me | 3 | —C$_2$(Me)$_4$— |
| 68 | Ti | Cl | 2-(2-Fu) | 3-Me, 5-Me | 3 | 2-(2-Fu) | 3-Me, 5-Me | 3 | —C$_2$(Me)$_4$— |
| 69 | Zr | Cl | 2-(3-Fu) | 4-Me, 5-Me | 3 | 2-(3-Fu) | 4-Me, 5-Me | 3 | —C$_2$(Me)$_4$— |
| 70 | Zr | Cl | 2-(3-Fu) | 3-Me, 5-Me | 3 | 2-(3-Fu) | 3-Me, 5-Me | 3 | —C$_2$(Me)$_4$— |
| 71 | Zr | Cl | 2-[2-(3-Me—Fu)] | 4-Me, 5-Me | 3 | 2-[2-(3-Me—Fu)] | 4-Me, 5-Me | 3 | —C$_2$(Me)$_4$— |
| 72 | Zr | Cl | 2-[2-(3-Me—Fu)] | 3-Me, 5-Me | 3 | 2-[2-(3-Me—Fu)] | 3-Me, 5-Me | 3 | —C$_2$(Me)$_4$— |
| 73 | Zr | Cl | 2-(2-Thie) | 4-Me, 5-Me | 3 | 2-(2-Thie) | 4-Me, 5-Me | 3 | —C$_2$(Me)$_4$— |

TABLE 3-continued

| | | | CA¹: Cyclopentadienyl | | | CA²: Cyclopentadienyl | | | |
|---|---|---|---|---|---|---|---|---|---|
| No. | M | X | Ra | R¹ | p + m | Ra | R¹ | q + n | Y |
| 74 | Zr | Cl | 2-(2-Thie) | 3-Me, 5-Me | 3 | 2-(2-Thie) | 3-Me, 5-Me | 3 | —C$_2$(Me)$_4$— |
| 75 | Zr | Cl | 2-(2-Py) | 4-Me, 5-Me | 3 | 2-(2-Py) | 4-Me, 5-Me | 3 | —C$_2$(Me)$_4$— |
| 76 | Zr | Cl | 2-(2-Py) | 3-Me, 5-Me | 3 | 2-(2-Py) | 3-Me, 5-Me | 3 | —C$_2$(Me)$_4$— |
| 77 | Zr | Cl | 2-(2-BzFu) | 4-Me, 5-Me | 3 | 2-(2-BzFu) | 4-Me, 5-Me | 3 | —C$_2$(Me)$_4$— |
| 78 | Zr | Cl | 2-(2-BzFu) | 3-Me, 5-Me | 3 | 2-(2-BzFu) | 3-Me, 5-Me | 3 | —C$_2$(Me)$_4$— |
| 79 | Zr | Cl | 2-[2-(1-Me—Pyr)] | 4-Me, 5-Me | 3 | 2-[2-(1-Me—Pyr)] | 4-Me, 5-Me | 3 | —C$_2$(Me)$_4$— |
| 80 | Zr | Cl | 2-[2-(1-Me—Pyr)] | 3-Me, 5-Me | 3 | 2-[2-(1-Me—Pyr)] | 3-Me, 5-Me | 3 | —C$_2$(Me)$_4$— |

TABLE 4

| | | | CA¹: Cyclopentadienyl | | | CA²: Cyclopentadienyl | | | |
|---|---|---|---|---|---|---|---|---|---|
| No. | M | X | Ra | R¹ | p + m | Ra | R¹ | q + n | Y |
| 81 | Zr | Cl | 2-(2-Fu) | — | 1 | 2-(2-Fu) | — | 1 | —SiH$_2$— |
| 82 | Zr | Cl | 2-(2-Fu) | — | 1 | 2-(2-Fu) | — | 1 | —Si(Me)$_2$— |
| 83 | Zr | Cl | 2-(2-Fu) | 5-Me | 2 | 2-(2-Fu) | 5-Me | 2 | —Si(Me)$_2$— |
| 84 | Zr | Cl | 2-(2-Fu) | 4-Me | 2 | 2-(2-Fu) | 4-Me | 2 | —Si(Me)$_2$— |
| 85 | Zr | Cl | 2-(2-Fu) | 4-OMe | 2 | 2-(2-Fu) | 4-OMe | 2 | —Si(Me)$_2$— |
| 86 | Zr | Cl | 2-(2-Fu) | 4-OPh | 2 | 2-(2-Fu) | 4-OPh | 2 | —Si(Me)$_2$— |
| 87 | Zr | Cl | 2-(2-Fu) | 4-Bzl | 2 | 2-(2-Fu) | 4-Bzl | 2 | —Si(Me)$_2$— |
| 88 | Zr | Cl | 2-(2-Fu) | 4-Tol | 2 | 2-(2-Fu) | 4-Tol | 2 | —Si(Me)$_2$— |
| 89 | Zr | Cl | 2-(2-Fu) | 4-OBzl | 2 | 2-(2-Fu) | 4-OBzl | 2 | —Si(Me)$_2$— |
| 90 | Zr | Cl | 2-(2-Fu) | 4-TMS | 2 | 2-(2-Fu) | 4-TMS | 2 | —Si(Me)$_2$— |
| 91 | Zr | Cl | 2-(2-Fu) | 4-(1-Pyr) | 2 | 2-(2-Fu) | 4-(1-Pyr) | 2 | —Si(Me)$_2$— |
| 92 | Zr | Cl | 2-(2-Fu) | 4-(1-Indo) | 2 | 2-(2-Fu) | 4-(1-Indo) | 2 | —Si(Me)$_2$— |
| 93 | Zr | Cl | 2-(2-Fu) | 3-Me | 2 | 2-(2-Fu) | 3-Me | 2 | —Si(Me)$_2$— |
| 94 | Zr | Cl | 2-(2-Fu) | 3-Me, 5-Me | 3 | 2-(2-Fu) | 3-Me, 5-Me | 3 | —Si(Me)$_2$— |
| 95 | Zr | Cl | 2-(2-Fu) | 4-Me, 5-Me | 3 | 2-(2-Fu) | 4-Me, 5-Me | 3 | —Si(Me)$_2$— |
| 96 | Zr | Cl | 2-(2-Fu) | 4-Et, 5-Me | 3 | 2-(2-Fu) | 4-Et, 5-Me | 3 | —Si(Me)$_2$— |
| 97 | Zr | Cl | 2-(2-Fu) | 4-(i-Pr), 5-Me | 3 | 2-(2-Fu) | 4-(i-Pr), 5-Me | 3 | —Si(Me)$_2$— |
| 98 | Zr | Cl | 2-(2-Fu) | 4-(t-Bu), 5-Me | 3 | 2-(2-Fu) | 4-(t-Bu), 5-Me | 3 | —Si(Me)$_2$— |
| 99 | Zr | Cl | 2-(2-Fu) | 4-Ph, 5-Me | 3 | 2-(2-Fu) | 4-Ph, 5-Me | 3 | —Si(Me)$_2$— |
| 100 | Zr | Cl | 2-(2-Fu) | 3-Ph, 5-Me | 3 | 2-(2-Fu) | 3-Ph, 5-Me | 3 | —Si(Me)$_2$— |
| 101 | Zr | Cl | 2-(2-Fu) | 4-Me, 5-Me | 3 | 2-(2-Fu) | 4-Me, 5-Me | 3 | —Si(Et)$_2$— |
| 102 | Zr | Cl | 2-(2-Fu) | 4-Me, 5-Me | 3 | 2-(2-Fu) | 4-Me, 5-Me | 3 | —Si(Ph)$_2$— |
| 103 | Zr | Me | 2-(2-Fu) | 4-Me, 5-Me | 3 | 2-(2-Fu) | 4-Me, 5-Me | 3 | —Si(Me)$_2$— |
| 104 | Zr | Bzl | 2-(2-Fu) | 4-Me, 5-Me | 3 | 2-(2-Fu) | 4-Me, 5-Me | 3 | —Si(Me)$_2$— |
| 105 | Hf | Cl | 2-(2-Fu) | 4-Me, 5-Me | 3 | 2-(2-Fu) | 4-Me, 5-Me | 3 | —Si(Me)$_2$— |
| 106 | Ti | Cl | 2-(2-Fu) | 4-Me, 5-Me | 3 | 2-(2-Fu) | 4-Me, 5-Me | 3 | —Si(Me)$_2$— |
| 107 | Hf | Cl | 2-(2-Fu) | 3-Me, 5-Me | 3 | 2-(2-Fu) | 3-Me, 5-Me | 3 | —Si(Me)$_2$— |
| 108 | Ti | Cl | 2-(2-Fu) | 3-Me, 5-Me | 3 | 2-(2-Fu) | 3-Me, 5-Me | 3 | —Si(Me)$_2$— |
| 109 | Zr | Cl | 2-(3-Fu) | 4-Me, 5-Me | 3 | 2-(3-Fu) | 4-Me, 5-Me | 3 | —Si(Me)$_2$— |
| 110 | Zr | Cl | 2-(3-Fu) | 3-Me, 5-Me | 3 | 2-(3-Fu) | 3-Me, 5-Me | 3 | —Si(Me)$_2$— |
| 111 | Zr | Cl | 2-[2-(3-Me—Fu)] | 4-Me, 5-Me | 3 | 2-[2-(3-Me—Fu)] | 4-Me, 5-Me | 3 | —Si(Me)$_2$— |
| 112 | Zr | Cl | 2-[2-(3-Me—Fu)] | 3-Me, 5-Me | 3 | 2-[2-(3-Me—Fu)] | 3-Me, 5-Me | 3 | —Si(Me)$_2$— |
| 113 | Zr | Cl | 2-(2-Thie) | 4-Me, 5-Me | 3 | 2-(2-Thie) | 4-Me, 5-Me | 3 | —Si(Me)$_2$— |
| 114 | Zr | Cl | 2-(2-Thie) | 3-Me, 5-Me | 3 | 2-(2-Thie) | 3-Me, 5-Me | 3 | —Si(Me)$_2$— |
| 115 | Zr | Cl | 2-(2-Py) | 4-Me, 5-Me | 3 | 2-(2-Py) | 4-Me, 5-Me | 3 | —Si(Me)$_2$— |
| 116 | Zr | Cl | 2-(2-Py) | 3-Me, 5-Me | 3 | 2-(2-Py) | 3-Me, 5-Me | 3 | —Si(Me)$_2$— |
| 117 | Zr | Cl | 2-(2-BzFu) | 4-Me, 5-Me | 3 | 2-(2-BzFu) | 4-Me, 5-Me | 3 | —Si(Me)$_2$— |
| 118 | Zr | Cl | 2-(2-BzFu) | 3-Me, 5-Me | 3 | 2-(2-BzFu) | 3-Me, 5-Me | 3 | —Si(Me)$_2$— |
| 119 | Zr | Cl | 2-[2-(N—Me—Pyr)] | 4-Me, 5-Me | 3 | 2-[2-(N—Me—Pyr)] | 4-Me, 5-Me | 3 | —Si(Me)$_2$— |
| 120 | Zr | Cl | 2-[2-(N—Me—Pyr)] | 3-Me, 5-Me | 3 | 2-[2-(N—Me—Pyr)] | 3-Me, 5-Me | 3 | —Si(Me)$_2$— |

TABLE 5

| | | | CA¹: Cyclopentadienyl | | | CA²: Cyclopentadienyl | | | |
|---|---|---|---|---|---|---|---|---|---|
| No. | M | X | Ra | R¹ | p + m | Ra | R¹ | q + n | Y |
| 121 | Zr | Cl | 2-(2-Fu) | — | 1 | 2-(2-Fu) | — | 1 | —GeH$_2$— |
| 122 | Zr | Cl | 2-(2-Fu) | — | 1 | 2-(2-Fu) | — | 1 | —Ge(Me)$_2$— |
| 123 | Zr | Cl | 2-(2-Fu) | 5-Me | 2 | 2-(2-Fu) | 5-Me | 2 | —Ge(Me)$_2$— |
| 124 | Zr | Cl | 2-(2-Fu) | 4-Me | 2 | 2-(2-Fu) | 4-Me | 2 | —Ge(Me)$_2$— |
| 125 | Zr | Cl | 2-(2-Fu) | 4-OMe | 2 | 2-(2-Fu) | 4-OMe | 2 | —Ge(Me)$_2$— |
| 126 | Zr | Cl | 2-(2-Fu) | 4-OPh | 2 | 2-(2-Fu) | 4-OPh | 2 | —Ge(Me)$_2$— |
| 127 | Zr | Cl | 2-(2-Fu) | 4-Bzl | 2 | 2-(2-Fu) | 4-Bzl | 2 | —Ge(Me)$_2$— |
| 128 | Zr | Cl | 2-(2-Fu) | 4-Tol | 2 | 2-(2-Fu) | 4-Tol | 2 | —Ge(Me)$_2$— |
| 129 | Zr | Cl | 2-(2-Fu) | 4-OBzl | 2 | 2-(2-Fu) | 4-OBzl | 2 | —Ge(Me)$_2$— |

TABLE 5-continued

|     |     |     | CA¹: Cyclopentadienyl | | | CA²: Cyclopentadienyl | | | |
| --- | --- | --- | --- | --- | --- | --- | --- | --- | --- |
| No. | M | X | Ra | R¹ | p + m | Ra | R¹ | q + n | Y |
| 130 | Zr | Cl | 2-(2-Fu) | 4-TMS | 2 | 2-(2-Fu) | 4-TMS | 2 | —Ge(Me)₂— |
| 131 | Zr | Cl | 2-(2-Fu) | 4-(1-Pyr) | 2 | 2-(2-Fu) | 4-(1-Pyr) | 2 | —Ge(Me)₂— |
| 132 | Zr | Cl | 2-(2-Fu) | 4-(1-Indo) | 2 | 2-(2-Fu) | 4-(1-Indo) | 2 | —Ge(Me)₂— |
| 133 | Zr | Cl | 2-(2-Fu) | 3-Me | 2 | 2-(2-Fu) | 3-Me | 2 | —Ge(Me)₂— |
| 134 | Zr | Cl | 2-(2-Fu) | 3-Me, 5-Me | 3 | 2-(2-Fu) | 3-Me, 5-Me | 3 | —Ge(Me)₂— |
| 135 | Zr | Cl | 2-(2-Fu) | 4-Me, 5-Me | 3 | 2-(2-Fu) | 4-Me, 5-Me | 3 | —Ge(Me)₂— |
| 136 | Zr | Cl | 2-(2-Fu) | 4-Et, 5-Me | 3 | 2-(2-Fu) | 4-Et, 5-Me | 3 | —Ge(Me)₂— |
| 137 | Zr | Cl | 2-(2-Fu) | 4-(i-Pr), 5-Me | 3 | 2-(2-Fu) | 4-(i-Pr), 5-Me | 3 | —Ge(Me)₂— |
| 138 | Zr | Cl | 2-(2-Fu) | 4-(t-Bu), 5-Me | 3 | 2-(2-Fu) | 4-(t-Bu), 5-Me | 3 | —Ge(Me)₂— |
| 139 | Zr | Cl | 2-(2-Fu) | 4-Ph, 5-Me | 3 | 2-(2-Fu) | 4-Ph, 5-Me | 3 | —Ge(Me)₂— |
| 140 | Zr | Cl | 2-(2-Fu) | 3-Ph, 5-Me | 3 | 2-(2-Fu) | 3-Ph, 5-Me | 3 | —Ge(Me)₂— |
| 141 | Zr | Cl | 2-(2-Fu) | 4-Me, 5-Me | 3 | 2-(2-Fu) | 4-Me, 5-Me | 3 | —Ge(Et)₂— |
| 142 | Zr | Cl | 2-(2-Fu) | 4-Me, 5-Me | 3 | 2-(2-Fu) | 4-Me, 5-Me | 3 | —Ge(Ph)₂— |
| 143 | Zr | Me | 2-(2-Fu) | 4-Me, 5-Me | 3 | 2-(2-Fu) | 4-Me, 5-Me | 3 | —Ge(Me)₂— |
| 144 | Zr | Bzl | 2-(2-Fu) | 4-Me, 5-Me | 3 | 2-(2-Fu) | 4-Me, 5-Me | 3 | —Ge(Me)₂— |
| 145 | Hf | Cl | 2-(2-Fu) | 4-Me, 5-Me | 3 | 2-(2-Fu) | 4-Me, 5-Me | 3 | —Ge(Me)₂— |
| 146 | Ti | Cl | 2-(2-Fu) | 4-Me, 5-Me | 3 | 2-(2-Fu) | 4-Me, 5-Me | 3 | —Ge(Me)₂— |
| 147 | Hf | Cl | 2-(2-Fu) | 3-Me, 5-Me | 3 | 2-(2-Fu) | 3-Me, 5-Me | 3 | —Ge(Me)₂— |
| 148 | Ti | Cl | 2-(2-Fu) | 3-Me, 5-Me | 3 | 2-(2-Fu) | 3-Me, 5-Me | 3 | —Ge(Me)₂— |
| 149 | Zr | Cl | 2-(3-Fu) | 4-Me, 5-Me | 3 | 2-(3-Fu) | 4-Me, 5-Me | 3 | —Ge(Me)₂— |
| 150 | Zr | Cl | 2-(3-Fu) | 3-Me, 5-Me | 3 | 2-(3-Fu) | 3-Me, 5-Me | 3 | —Ge(Me)₂— |
| 151 | Zr | Cl | 2-[2-(3-Me—Fu)] | 4-Me, 5-Me | 3 | 2-[2-(3-Me—Fu)] | 4-Me, 5-Me | 3 | —Ge(Me)₂— |
| 152 | Zr | Cl | 2-[2-(3-Me—Fu)] | 3-Me, 5-Me | 3 | 2-[2-(3-Me—Fu)] | 3-Me, 5-Me | 3 | —Ge(Me)₂— |
| 153 | Zr | Cl | 2-(2-Thie) | 4-Me, 5-Me | 3 | 2-(2-Thie) | 4-Me, 5-Me | 3 | —Ge(Me)₂— |
| 154 | Zr | Cl | 2-(2-Thie) | 3-Me, 5-Me | 3 | 2-(2-Thie) | 3-Me, 5-Me | 3 | —Ge(Me)₂— |
| 155 | Zr | Cl | 2-(2-Py) | 4-Me, 5-Me | 3 | 2-(2-Py) | 4-Me, 5-Me | 3 | —Ge(Me)₂— |
| 156 | Zr | Cl | 2-(2-Py) | 3-Me, 5-Me | 3 | 2-(2-Py) | 3-Me, 5-Me | 3 | —Ge(Me)₂— |
| 157 | Zr | Cl | 2-(2-BzFu) | 4-Me, 5-Me | 3 | 2-(2-BzFu) | 4-Me, 5-Me | 3 | —Ge(Me)₂— |
| 158 | Zr | Cl | 2-(2-BzFu) | 3-Me, 5-Me | 3 | 2-(2-BzFu) | 3-Me, 5-Me | 3 | —Ge(Me)₂— |
| 159 | Zr | Cl | 2-[2-(N—Me—Pyr)] | 4-Me, 5-Me | 3 | 2-[2-(N—Me—Pyr)] | 4-Me, 5-Me | 3 | —Ge(Me)₂— |
| 160 | Zr | Cl | 2-[2-(N—Me—Pyr)] | 3-Me, 5-Me | 3 | 2-[2-(N—Me—Pyr)] | 3-Me, 5-Me | 3 | —Ge(Me)₂— |

TABLE 6

|     |     |     | CA¹: Cyclopentadienyl | | | CA²: Cyclopentadienyl | | | |
| --- | --- | --- | --- | --- | --- | --- | --- | --- | --- |
| No. | M | X | Ra | R¹ | p + m | Ra | R¹ | q + n | Y |
| 161 | Zr | Cl | 3-(2-Fu) | — | 1 | 3-(2-Fu) | — | 1 | —CH₂— |
| 162 | Zr | Cl | 3-(2-Fu) | — | 1 | 3-(2-Fu) | — | 1 | —C(Me)₂— |
| 163 | Zr | Cl | 3-(2-Fu) | 5-Me | 2 | 3-(2-Fu) | 5-Me | 2 | —C(Me)₂— |
| 164 | Zr | Cl | 3-(2-Fu) | 4-Me | 2 | 3-(2-Fu) | 4-Me | 2 | —C(Me)₂— |
| 165 | Zr | Cl | 3-(2-Fu) | 4-OMe | 2 | 3-(2-Fu) | 4-OMe | 2 | —C(Me)₂— |
| 166 | Zr | Cl | 3-(2-Fu) | 4-OPh | 2 | 3-(2-Fu) | 4-OPh | 2 | —C(Me)₂— |
| 167 | Zr | Cl | 3-(2-Fu) | 4-Bzl | 2 | 3-(2-Fu) | 4-Bzl | 2 | —C(Me)₂— |
| 168 | Zr | Cl | 3-(2-Fu) | 4-Tol | 2 | 3-(2-Fu) | 4-Tol | 2 | —C(Me)₂— |
| 169 | Zr | Cl | 3-(2-Fu) | 4-OBzl | 2 | 3-(2-Fu) | 4-OBzl | 2 | —C(Me)₂— |
| 170 | Zr | Cl | 3-(2-Fu) | 4-TMS | 2 | 3-(2-Fu) | 4-TMS | 2 | —C(Me)₂— |
| 171 | Zr | Cl | 3-(2-Fu) | 4-(1-Pyr) | 2 | 3-(2-Fu) | 4-(1-Pyr) | 2 | —C(Me)₂— |
| 172 | Zr | Cl | 3-(2-Fu) | 4-(1-Indo) | 2 | 3-(2-Fu) | 4-(1-Indo) | 2 | —C(Me)₂— |
| 173 | Zr | Cl | 3-(2-Fu) | 2-Me | 2 | 3-(2-Fu) | 2-Me | 2 | —C(Me)₂— |
| 174 | Zr | Cl | 3-(2-Fu) | 2-Me, 5-Me | 3 | 3-(2-Fu) | 2-Me, 5-Me | 3 | —C(Me)₂— |
| 175 | Zr | Cl | 3-(2-Fu) | 4-Me, 5-Me | 3 | 3-(2-Fu) | 4-Me, 5-Me | 3 | —C(Me)₂— |
| 176 | Zr | Cl | 3-(2-Fu) | 4-Et, 5-Me | 3 | 3-(2-Fu) | 4-Et, 5-Me | 3 | —C(Me)₂— |
| 177 | Zr | Cl | 3-(2-Fu) | 4-(i-Pr), 5-Me | 3 | 3-(2-Fu) | 4-(i-Pr), 5-Me | 3 | —C(Me)₂— |
| 178 | Zr | Cl | 3-(2-Fu) | 4-(t-Bu), 5-Me | 3 | 3-(2-Fu) | 4-(t-Bu), 5-Me | 3 | —C(Me)₂— |
| 179 | Zr | Cl | 3-(2-Fu) | 4-Ph, 5-Me | 3 | 3-(2-Fu) | 4-Ph, 5-Me | 3 | —C(Me)₂— |
| 180 | Zr | Cl | 3-(2-Fu) | 2-Ph, 5-Me | 3 | 3-(2-Fu) | 2-Ph, 5-Me | 3 | —C(Me)₂— |
| 181 | Zr | Cl | 3-(2-Fu) | 4-Me, 5-Me | 3 | 3-(2-Fu) | 4-Me, 5-Me | 3 | —C(Et)₂— |
| 182 | Zr | Cl | 3-(2-Fu) | 4-Me, 5-Me | 3 | 3-(2-Fu) | 4-Me, 5-Me | 3 | —C(Ph)₂— |
| 183 | Zr | Me | 3-(2-Fu) | 4-Me, 5-Me | 3 | 3-(2-Fu) | 4-Me, 5-Me | 3 | —C(Me)₂— |
| 184 | Zr | Bzl | 3-(2-Fu) | 4-Me, 5-Me | 3 | 3-(2-Fu) | 4-Me, 5-Me | 3 | —C(Me)₂— |
| 185 | Hf | Cl | 3-(2-Fu) | 4-Me, 5-Me | 3 | 3-(2-Fu) | 4-Me, 5-Me | 3 | —C(Me)₂— |
| 186 | Ti | Cl | 3-(2-Fu) | 4-Me, 5-Me | 3 | 3-(2-Fu) | 4-Me, 5-Me | 3 | —C(Me)₂— |
| 187 | Hf | Cl | 3-(2-Fu) | 2-Me, 5-Me | 3 | 3-(2-Fu) | 2-Me, 5-Me | 3 | —C(Me)₂— |
| 188 | Ti | Cl | 3-(2-Fu) | 2-Me, 5-Me | 3 | 3-(2-Fu) | 2-Me, 5-Me | 3 | —C(Me)₂— |
| 189 | Zr | Cl | 3-(3-Fu) | 4-Me, 5-Me | 3 | 3-(3-Fu) | 4-Me, 5-Me | 3 | —C(Me)₂— |
| 190 | Zr | Cl | 3-(3-Fu) | 2-Me, 5-Me | 3 | 3-(3-Fu) | 2-Me, 5-Me | 3 | —C(Me)₂— |
| 191 | Zr | Cl | 3-[2-(3-Me—Fu)] | 4-Me, 5-Me | 3 | 3-[2-(3-Me—Fu)] | 4-Me, 5-Me | 3 | —C(Me)₂— |
| 192 | Zr | Cl | 3-[2-(3-Me—Fu)] | 3-Me, 5-Me | 3 | 3-[2-(3-Me—Fu)] | 2-Me, 5-Me | 3 | —C(Me)₂— |
| 193 | Zr | Cl | 3-(2-Thie) | 4-Me, 5-Me | 3 | 3-(2-Thie) | 4-Me, 5-Me | 3 | —C(Me)₂— |
| 194 | Zr | Cl | 3-(2-Thie) | 2-Me, 5-Me | 3 | 3-(2-Thie) | 2-Me, 5-Me | 3 | —C(Me)₂— |

TABLE 6-continued

| | | | CA¹: Cyclopentadienyl | | | CA²: Cyclopentadienyl | | | |
|---|---|---|---|---|---|---|---|---|---|
| No. | M | X | Ra | R¹ | p + m | Ra | R¹ | q + n | Y |
| 195 | Zr | Cl | 3-(2-Py) | 4-Me, 5-Me | 3 | 3-(2-Py) | 4-Me, 5-Me | 3 | —C(Me)₂— |
| 196 | Zr | Cl | 3-(2-Py) | 2-Me, 5-Me | 3 | 3-(2-Py) | 2-Me, 5-Me | 3 | —C(Me)₂— |
| 197 | Zr | Cl | 3-(2-BzFu) | 4-Me, 5-Me | 3 | 3-(2-BzFu) | 4-Me, 5-Me | 3 | —C(Me)₂— |
| 198 | Zr | Cl | 3-(2-BzFu) | 2-Me, 5-Me | 3 | 3-(2-BzFu) | 2-Me, 5-Me | 3 | —C(Me)₂— |
| 199 | Zr | Cl | 3-[2-(N—Me—Pyr)] | 4-Me, 5-Me | 3 | 3-[2-(N—Me—Pyr)] | 4-Me, 5-Me | 3 | —C(Me)₂— |
| 200 | Zr | Cl | 3-[2-(N—Me—Pyr)] | 2-Me, 5-Me | 3 | 3-[2-(N—Me—Pyr)] | 2-Me, 5-Me | 3 | —C(Me)₂— |

TABLE 7

| | | | CA¹: Cyclopentadienyl | | | CA²: Cyclopentadienyl | | | |
|---|---|---|---|---|---|---|---|---|---|
| No. | M | X | Ra | R¹ | p + m | Ra | R¹ | q + n | Y |
| 201 | Zr | Cl | 3-(2-Fu) | — | 1 | 3-(2-Fu) | — | 1 | —CH₂CH₂— |
| 202 | Zr | Cl | 3-(2-Fu) | — | 1 | 3-(2-Fu) | — | 1 | —C₂(Me)₄— |
| 203 | Zr | Cl | 3-(2-Fu) | 5-Me | 2 | 3-(2-Fu) | 5-Me | 2 | —C₂(Me)₄— |
| 204 | Zr | Cl | 3-(2-Fu) | 4-Me | 2 | 3-(2-Fu) | 4-Me | 2 | —C₂(Me)₄— |
| 205 | Zr | Cl | 3-(2-Fu) | 4-OMe | 2 | 3-(2-Fu) | 4-OMe | 2 | —C₂(Me)₄— |
| 206 | Zr | Cl | 3-(2-Fu) | 4-OPh | 2 | 3-(2-Fu) | 4-OPh | 2 | —C₂(Me)₄— |
| 207 | Zr | Cl | 3-(2-Fu) | 4-Bzl | 2 | 3-(2-Fu) | 4-Bzl | 2 | —C₂(Me)₄— |
| 208 | Zr | Cl | 3-(2-Fu) | 4-Tol | 2 | 3-(2-Fu) | 4-Tol | 2 | —C₂(Me)₄— |
| 209 | Zr | Cl | 3-(2-Fu) | 4-OBzl | 2 | 3-(2-Fu) | 4-OBzl | 2 | —C₂(Me)₄— |
| 210 | Zr | Cl | 3-(2-Fu) | 4-TMS | 2 | 3-(2-Fu) | 4-TMS | 2 | —C₂(Me)₄— |
| 211 | Zr | Cl | 3-(2-Fu) | 4-(1-Pyr) | 2 | 3-(2-Fu) | 4-(1-Pyr) | 2 | —C₂(Me)₄— |
| 212 | Zr | Cl | 3-(2-Fu) | 4-(1-Indo) | 2 | 3-(2-Fu) | 4-(1-Indo) | 2 | —C₂(Me)₄— |
| 213 | Zr | Cl | 3-(2-Fu) | 2-Me | 2 | 3-(2-Fu) | 2-Me | 2 | —C₂(Me)₄— |
| 214 | Zr | Cl | 3-(2-Fu) | 2-Me, 5-Me | 3 | 3-(2-Fu) | 2-Me, 5-Me | 3 | —C₂(Me)₄— |
| 215 | Zr | Cl | 3-(2-Fu) | 4-Me, 5-Me | 3 | 3-(2-Fu) | 4-Me, 5-Me | 3 | —C₂(Me)₄— |
| 216 | Zr | Cl | 3-(2-Fu) | 4-Et, 5-Me | 3 | 3-(2-Fu) | 4-Et, 5-Me | 3 | —C₂(Me)₄— |
| 217 | Zr | Cl | 3-(2-Fu) | 4-(i-Pr), 5-Me | 3 | 3-(2-Fu) | 4-(i-Pr), 5-Me | 3 | —C₂(Me)₄— |
| 218 | Zr | Cl | 3-(2-Fu) | 4-(t-Bu), 5-Me | 3 | 3-(2-Fu) | 4-(t-Bu), 5-Me | 3 | —C₂(Me)₄— |
| 219 | Zr | Cl | 3-(2-Fu) | 4-Ph, 5-Me | 3 | 3-(2-Fu) | 4-Ph, 5-Me | 3 | —C₂(Me)₄— |
| 220 | Zr | Cl | 3-(2-Fu) | 2-Ph, 5-Me | 3 | 3-(2-Fu) | 2-Ph, 5-Me | 3 | —C₂(Me)₄— |
| 221 | Zr | Cl | 3-(2-Fu) | 4-Me, 5-Me | 3 | 3-(2-Fu) | 4-Me, 5-Me | 3 | —C₂(Et)₄— |
| 222 | Zr | Cl | 3-(2-Fu) | 4-Me, 5-Me | 3 | 3-(2-Fu) | 4-Me, 5-Me | 3 | —C₂(Ph)₄— |
| 223 | Zr | Me | 3-(2-Fu) | 4-Me, 5-Me | 3 | 3-(2-Fu) | 4-Me, 5-Me | 3 | —C₂(Me)₄— |
| 224 | Zr | Bzl | 3-(2-Fu) | 4-Me, 5-Me | 3 | 3-(2-Fu) | 4-Me, 5-Me | 3 | —C₂(Me)₄— |
| 225 | Hf | Cl | 3-(2-Fu) | 4-Me, 5-Me | 3 | 3-(2-Fu) | 4-Me, 5-Me | 3 | —C₂(Me)₄— |
| 226 | Ti | Cl | 3-(2-Fu) | 4-Me, 5-Me | 3 | 3-(2-Fu) | 4-Me, 5-Me | 3 | —C₂(Me)₄— |
| 227 | Hf | Cl | 3-(2-Fu) | 2-Me, 5-Me | 3 | 3-(2-Fu) | 2-Me, 5-Me | 3 | —C₂(Me)₄— |
| 228 | Ti | Cl | 3-(2-Fu) | 2-Me, 5-Me | 3 | 3-(2-Fu) | 2-Me, 5-Me | 3 | —C₂(Me)₄— |
| 229 | Zr | Cl | 3-(3-Fu) | 4-Me, 5-Me | 3 | 3-(3-Fu) | 4-Me, 5-Me | 3 | —C₂(Me)₄— |
| 230 | Zr | Cl | 3-(3-Fu) | 2-Me, 5-Me | 3 | 3-(3-Fu) | 2-Me, 5-Me | 3 | —C₂(Me)₄— |
| 231 | Zr | Cl | 3-[2-(3-Me—Fu)] | 4-Me, 5-Me | 3 | 3-[2-(3-Me—Fu)] | 4-Me, 5-Me | 3 | —C₂(Me)₄— |
| 232 | Zr | Cl | 3-[2-(3-Me—Fu)] | 2-Me, 5-Me | 3 | 3-[2-(3-Me—Fu)] | 2-Me, 5-Me | 3 | —C₂(Me)₄— |
| 233 | Zr | Cl | 3-(2-Thie) | 4-Me, 5-Me | 3 | 3-(2-Thie) | 4-Me, 5-Me | 3 | —C₂(Me)₄— |
| 234 | Zr | Cl | 3-(2-Thie) | 2-Me, 5-Me | 3 | 3-(2-Thie) | 2-Me, 5-Me | 3 | —C₂(Me)₄— |
| 235 | Zr | Cl | 3-(2-Py) | 4-Me, 5-Me | 3 | 3-(2-Py) | 4-Me, 5-Me | 3 | —C₂(Me)₄— |
| 236 | Zr | Cl | 3-(2-Py) | 2-Me, 5-Me | 3 | 3-(2-Py) | 2-Me, 5-Me | 3 | —C₂(Me)₄— |
| 237 | Zr | Cl | 3-(2-BzFu) | 4-Me, 5-Me | 3 | 3-(2-BzFu) | 4-Me, 5-Me | 3 | —C₂(Me)₄— |
| 238 | Zr | Cl | 3-(2-BzFu) | 2-Me, 5-Me | 3 | 3-(2-BzFu) | 2-Me, 5-Me | 3 | —C₂(Me)₄— |
| 239 | Zr | Cl | 3-[2-(N—Me—Pyr)] | 4-Me, 5-Me | 3 | 3-[2-(N—Me—Pyr)] | 4-Me, 5-Me | 3 | —C₂(Me)₄— |
| 240 | Zr | Cl | 3-[2-(N—Me—Pyr)] | 2-Me, 5-Me | 3 | 3-[2-(N—Me—Pyr)] | 2-Me, 5-Me | 3 | —C₂(Me)₄— |

TABLE 8

| | | | CA¹: Cyclopentadienyl | | | CA²: Cyclopentadienyl | | | |
|---|---|---|---|---|---|---|---|---|---|
| No. | M | X | Ra | R¹ | p + m | Ra | R¹ | q + n | Y |
| 241 | Zr | Cl | 3-(2-Fu) | — | 1 | 3-(2-Fu) | — | 1 | —SiH₂— |
| 242 | Zr | Cl | 3-(2-Fu) | — | 1 | 3-(2-Fu) | — | 1 | —Si(Me)₂— |
| 243 | Zr | Cl | 3-(2-Fu) | 5-Me | 2 | 3-(2-Fu) | 5-Me | 2 | —Si(Me)₂— |
| 244 | Zr | Cl | 3-(2-Fu) | 4-Me | 2 | 3-(2-Fu) | 4-Me | 2 | —Si(Me)₂— |
| 245 | Zr | Cl | 3-(2-Fu) | 4-OMe | 2 | 3-(2-Fu) | 4-OMe | 2 | —Si(Me)₂— |
| 246 | Zr | Cl | 3-(2-Fu) | 4-OPh | 2 | 3-(2-Fu) | 4-OPh | 2 | —Si(Me)₂— |
| 247 | Zr | Cl | 3-(2-Fu) | 4-Bzl | 2 | 3-(2-Fu) | 4-Bzl | 2 | —Si(Me)₂— |
| 248 | Zr | Cl | 3-(2-Fu) | 4-Tol | 2 | 3-(2-Fu) | 4-Tol | 2 | —Si(Me)₂— |
| 249 | Zr | Cl | 3-(2-Fu) | 4-OBzl | 2 | 3-(2-Fu) | 4-OBzl | 2 | —Si(Me)₂— |
| 250 | Zr | Cl | 3-(2-Fu) | 4-TMS | 2 | 3-(2-Fu) | 4-TMS | 2 | —Si(Me)₂— |

TABLE 8-continued

|  |  |  | CA$^1$: Cyclopentadienyl | | | CA$^2$: Cyclopentadienyl | | | |
| --- | --- | --- | --- | --- | --- | --- | --- | --- | --- |
| No. | M | X | Ra | R$^1$ | p + m | Ra | R$^1$ | q + n | Y |
| 251 | Zr | Cl | 3-(2-Fu) | 4-(1-Pyr) | 2 | 3-(2-Fu) | 4-(1-Pyr) | 2 | —Si(Me)$_2$— |
| 252 | Zr | Cl | 3-(2-Fu) | 4-(1-Indo) | 2 | 3-(2-Fu) | 4-(1-Indo) | 2 | —Si(Me)$_2$— |
| 253 | Zr | Cl | 3-(2-Fu) | 2-Me | 2 | 3-(2-Fu) | 2-Me | 2 | —Si(Me)$_2$— |
| 254 | Zr | Cl | 3-(2-Fu) | 2-Me, 5-Me | 3 | 3-(2-Fu) | 2-Me, 5-Me | 3 | —Si(Me)$_2$— |
| 255 | Zr | Cl | 3-(2-Fu) | 4-Me, 5-Me | 3 | 3-(2-Fu) | 4-Me, 5-Me | 3 | —Si(Me)$_2$— |
| 256 | Zr | Cl | 3-(2-Fu) | 4-Et, 5-Me | 3 | 3-(2-Fu) | 4-Et, 5-Me | 3 | —Si(Me)$_2$— |
| 257 | Zr | Cl | 3-(2-Fu) | 4-(i-Pr), 5-Me | 3 | 3-(2-Fu) | 4-(i-Pr), 5-Me | 3 | —Si(Me)$_2$— |
| 258 | Zr | Cl | 3-(2-Fu) | 4-(t-Bu), 5-Me | 3 | 3-(2-Fu) | 4-(t-Bu), 5-Me | 3 | —Si(Me)$_2$— |
| 259 | Zr | Cl | 3-(2-Fu) | 4-Ph, 5-Me | 3 | 3-(2-Fu) | 4-Ph, 5-Me | 3 | —Si(Me)$_2$— |
| 260 | Zr | Cl | 3-(2-Fu) | 2-Ph, 5-Me | 3 | 3-(2-Fu) | 2-Ph, 5-Me | 3 | —Si(Me)$_2$— |
| 261 | Zr | Cl | 3-(2-Fu) | 4-Me, 5-Me | 3 | 3-(2-Fu) | 4-Me, 5-Me | 3 | —Si(Et)$_2$— |
| 262 | Zr | Cl | 3-(2-Fu) | 4-Me, 5-Me | 3 | 3-(2-Fu) | 4-Me, 5-Me | 3 | —Si(Ph)$_2$— |
| 263 | Zr | Me | 3-(2-Fu) | 4-Me, 5-Me | 3 | 3-(2-Fu) | 4-Me, 5-Me | 3 | —Si(Me)$_2$— |
| 264 | Zr | Bzl | 3-(2-Fu) | 4-Me, 5-Me | 3 | 3-(2-Fu) | 4-Me, 5-Me | 3 | —Si(Me)$_2$— |
| 265 | Hf | Cl | 3-(2-Fu) | 4-Me, 5-Me | 3 | 3-(2-Fu) | 4-Me, 5-Me | 3 | —Si(Me)$_2$— |
| 266 | Ti | Cl | 3-(2-Fu) | 4-Me, 5-Me | 3 | 3-(2-Fu) | 4-Me, 5-Me | 3 | —Si(Me)$_2$— |
| 267 | Hf | Cl | 3-(2-Fu) | 2-Me, 5-Me | 3 | 3-(2-Fu) | 2-Me, 5-Me | 3 | —Si(Me)$_2$— |
| 268 | Ti | Cl | 3-(2-Fu) | 2-Me, 5-Me | 3 | 3-(2-Fu) | 2-Me, 5-Me | 3 | —Si(Me)$_2$— |
| 269 | Zr | Cl | 3-(3-Fu) | 4-Me, 5-Me | 3 | 3-(3-Fu) | 4-Me, 5-Me | 3 | —Si(Me)$_2$— |
| 270 | Zr | Cl | 3-(3-Fu) | 2-Me, 5-Me | 3 | 3-(3-Fu) | 2-Me, 5-Me | 3 | —Si(Me)$_2$— |
| 271 | Zr | Cl | 3-[2-(3-Me—Fu)] | 4-Me, 5-Me | 3 | 3-[2-(3-Me—Fu)] | 4-Me, 5-Me | 3 | —Si(Me)$_2$— |
| 272 | Zr | Cl | 3-[2-(3-Me—Fu)] | 2-Me, 5-Me | 3 | 3-[2-(3-Me—Fu)] | 2-Me, 5-Me | 3 | —Si(Me)$_2$— |
| 273 | Zr | Cl | 3-(2-Thie) | 4-Me, 5-Me | 3 | 3-(2-Thie) | 4-Me, 5-Me | 3 | —Si(Me)$_2$— |
| 274 | Zr | Cl | 3-(2-Thie) | 2-Me, 5-Me | 3 | 3-(2-Thie) | 2-Me, 5-Me | 3 | —Si(Me)$_2$— |
| 275 | Zr | Cl | 3-(2-Py) | 4-Me, 5-Me | 3 | 3-(2-Py) | 4-Me, 5-Me | 3 | —Si(Me)$_2$— |
| 276 | Zr | Cl | 3-(2-Py) | 2-Me, 5-Me | 3 | 3-(2-Py) | 2-Me, 5-Me | 3 | —Si(Me)$_2$— |
| 277 | Zr | Cl | 3-(2-BzFu) | 4-Me, 5-Me | 3 | 3-(2-BzFu) | 4-Me, 5-Me | 3 | —Si(Me)$_2$— |
| 278 | Zr | Cl | 3-(2-BzFu) | 2-Me, 5-Me | 3 | 3-(2-BzFu) | 2-Me, 5-Me | 3 | —Si(Me)$_2$— |
| 279 | Zr | Cl | 3-[2-(N—Me—Pyr)] | 4-Me, 5-Me | 3 | 3-[2-(N—Me—Pyr)] | 4-Me, 5-Me | 3 | —Si(Me)$_2$— |
| 280 | Zr | Cl | 3-[2-(N—Me—Pyr)] | 2-Me, 5-Me | 3 | 3-[2-(N—Me—Pyr)] | 2-Me, 5-Me | 3 | —Si(Me)$_2$— |

TABLE 9

|  |  |  | CA$^1$: Cyclopentadienyl | | | CA$^2$: Cyclopentadienyl | | | |
| --- | --- | --- | --- | --- | --- | --- | --- | --- | --- |
| No. | M | X | Ra | R$^1$ | p + m | Ra | R$^1$ | q + n | Y |
| 281 | Zr | Cl | 3-(2-Fu) | — | 1 | 3-(2-Fu) | — | 1 | —GeH$_2$— |
| 282 | Zr | Cl | 3-(2-Fu) | — | 1 | 3-(2-Fu) | — | 1 | —Ge(Me)$_2$— |
| 283 | Zr | Cl | 3-(2-Fu) | 5-Me | 2 | 3-(2-Fu) | 5-Me | 2 | —Ge(Me)$_2$— |
| 284 | Zr | Cl | 3-(2-Fu) | 4-Me | 2 | 3-(2-Fu) | 4-Me | 2 | —Ge(Me)$_2$— |
| 285 | Zr | Cl | 3-(2-Fu) | 4-OMe | 2 | 3-(2-Fu) | 4-OMe | 2 | —Ge(Me)$_2$— |
| 286 | Zr | Cl | 3-(2-Fu) | 4-OPh | 2 | 3-(2-Fu) | 4-OPh | 2 | —Ge(Me)$_2$— |
| 287 | Zr | Cl | 3-(2-Fu) | 4-Bzl | 2 | 3-(2-Fu) | 4-Bzl | 2 | —Ge(Me)$_2$— |
| 288 | Zr | Cl | 3-(2-Fu) | 4-Tol | 2 | 3-(2-Fu) | 4-Tol | 2 | —Ge(Me)$_2$— |
| 289 | Zr | Cl | 3-(2-Fu) | 4-OBzl | 2 | 3-(2-Fu) | 4-OBzl | 2 | —Ge(Me)$_2$— |
| 290 | Zr | Cl | 3-(2-Fu) | 4-TMS | 2 | 3-(2-Fu) | 4-TMS | 2 | —Ge(Me)$_2$— |
| 291 | Zr | Cl | 3-(2-Fu) | 4-(1-Pyr) | 2 | 3-(2-Fu) | 4-(1-Pyr) | 2 | —Ge(Me)$_2$— |
| 292 | Zr | Cl | 3-(2-Fu) | 4-(1-Indo) | 2 | 3-(2-Fu) | 4-(1-Indo) | 2 | —Ge(Me)$_2$— |
| 293 | Zr | Cl | 3-(2-Fu) | 2-Me | 2 | 3-(2-Fu) | 2-Me | 2 | —Ge(Me)$_2$— |
| 294 | Zr | Cl | 3-(2-Fu) | 2-Me, 5-Me | 3 | 3-(2-Fu) | 2-Me, 5-Me | 3 | —Ge(Me)$_2$— |
| 295 | Zr | Cl | 3-(2-Fu) | 4-Me, 5-Me | 3 | 3-(2-Fu) | 4-Me, 5-Me | 3 | —Ge(Me)$_2$— |
| 296 | Zr | Cl | 3-(2-Fu) | 4-Et, 5-Me | 3 | 3-(2-Fu) | 4-Et, 5-Me | 3 | —Ge(Me)$_2$— |
| 297 | Zr | Cl | 3-(2-Fu) | 4-(i-Pr), 5-Me | 3 | 3-(2-Fu) | 4-(i-Pr), 5-Me | 3 | —Ge(Me)$_2$— |
| 298 | Zr | Cl | 3-(2-Fu) | 4-(t-Bu), 5-Me | 3 | 3-(2-Fu) | 4-(t-Bu), 5-Me | 3 | —Ge(Me)$_2$— |
| 299 | Zr | Cl | 3-(2-Fu) | 4-Ph, 5-Me | 3 | 3-(2-Fu) | 4-Ph, 5-Me | 3 | —Ge(Me)$_2$— |
| 300 | Zr | Cl | 3-(2-Fu) | 2-Ph, 5-Me | 3 | 3-(2-Fu) | 2-Ph, 5-Me | 3 | —Ge(Me)$_2$— |
| 301 | Zr | Cl | 3-(2-Fu) | 4-Me, 5-Me | 3 | 3-(2-Fu) | 4-Me, 5-Me | 3 | —Ge(Et)$_2$— |
| 302 | Zr | Cl | 3-(2-Fu) | 4-Me, 5-Me | 3 | 3-(2-Fu) | 4-Me, 5-Me | 3 | —Ge(Ph)$_2$— |
| 303 | Zr | Me | 3-(2-Fu) | 4-Me, 5-Me | 3 | 3-(2-Fu) | 4-Me, 5-Me | 3 | —Ge(Me)$_2$— |
| 304 | Zr | Bzl | 3-(2-Fu) | 4-Me, 5-Me | 3 | 3-(2-Fu) | 4-Me, 5-Me | 3 | —Ge(Me)$_2$— |
| 305 | Hf | Cl | 3-(2-Fu) | 4-Me, 5-Me | 3 | 3-(2-Fu) | 4-Me, 5-Me | 3 | —Ge(Me)$_2$— |
| 306 | Ti | Cl | 3-(2-Fu) | 4-Me, 5-Me | 3 | 3-(2-Fu) | 4-Me, 5-Me | 3 | —Ge(Me)$_2$— |
| 307 | Hf | Cl | 3-(2-Fu) | 2-Me, 5-Me | 3 | 3-(2-Fu) | 2-Me, 5-Me | 3 | —Ge(Me)$_2$— |
| 308 | Ti | Cl | 3-(2-Fu) | 2-Me, 5-Me | 3 | 3-(2-Fu) | 2-Me, 5-Me | 3 | —Ge(Me)$_2$— |
| 309 | Zr | Cl | 3-(3-Fu) | 4-Me, 5-Me | 3 | 3-(3-Fu) | 4-Me, 5-Me | 3 | —Ge(Me)$_2$— |
| 310 | Zr | Cl | 3-(3-Fu) | 2-Me, 5-Me | 3 | 3-(3-Fu) | 2-Me, 5-Me | 3 | —Ge(Me)$_2$— |
| 311 | Zr | Cl | 3-[2-(3-Me—Fu)] | 4-Me, 5-Me | 3 | 3-[2-(3-Me—Fu)] | 4-Me, 5-Me | 3 | —Ge(Me)$_2$— |
| 312 | Zr | Cl | 3-[2-(3-Me—Fu)] | 2-Me, 5-Me | 3 | 3-[2-(3-Me—Fu)] | 2-Me, 5-Me | 3 | —Ge(Me)$_2$— |
| 313 | Zr | Cl | 3-(2-Thie) | 4-Me, 5-Me | 3 | 3-(2-Thie) | 4-Me, 5-Me | 3 | —Ge(Me)$_2$— |
| 314 | Zr | Cl | 3-(2-Thie) | 2-Me, 5-Me | 3 | 3-(2-Thie) | 2-Me, 5-Me | 3 | —Ge(Me)$_2$— |
| 315 | Zr | Cl | 3-(2-Py) | 4-Me, 5-Me | 3 | 3-(2-Py) | 4-Me, 5-Me | 3 | —Ge(Me)$_2$— |

TABLE 9-continued

|  |  |  | CA¹: Cyclopentadienyl | | | CA²: Cyclopentadienyl | | | |
| --- | --- | --- | --- | --- | --- | --- | --- | --- | --- |
| No. | M | X | Ra | R¹ | p + m | Ra | R¹ | q + n | Y |
| 316 | Zr | Cl | 3-(2-Py) | 2-Me, 5-Me | 3 | 3-(2-Py) | 2-Me, 5-Me | 3 | —Ge(Me)$_2$— |
| 317 | Zr | Cl | 3-(2-BzFu) | 4-Me, 5-Me | 3 | 3-(2-BzFu) | 4-Me, 5-Me | 3 | —Ge(Me)$_2$— |
| 318 | Zr | Cl | 3-(2-BzFu) | 2-Me, 5-Me | 3 | 3-(2-BzFu) | 2-Me, 5-Me | 3 | —Ge(Me)$_2$— |
| 319 | Zr | Cl | 3-[2-(N—Me—Pyr)] | 4-Me, 5-Me | 3 | 3-[2-(N—Me—Pyr)] | 4-Me, 5-Me | 3 | —Ge(Me)$_2$— |
| 320 | Zr | Cl | 3-[2-(N—Me—Pyr)] | 2-Me, 5-Me | 3 | 3-[2-(N—Me—Pyr)] | 2-Me, 5-Me | 3 | —Ge(Me)$_2$— |

TABLE 10

|  |  |  | CA¹: Indenyl | | | CA²: Indenyl | | | |
| --- | --- | --- | --- | --- | --- | --- | --- | --- | --- |
| No. | M | X | Ra | R¹ | p + m | Ra | R¹ | q + n | Y |
| 321 | Zr | Cl | 2-(2-Fu) | — | 1 | 2-(2-Fu) | — | 1 | —CH$_2$— |
| 322 | Zr | Cl | 2-(2-Fu) | — | 1 | 2-(2-Fu) | — | 1 | —C(Me)$_2$— |
| 323 | Zr | Cl | 2-(2-Fu) | 7-Me | 2 | 2-(2-Fu) | 7-Me | 2 | —C(Me)$_2$— |
| 324 | Zr | Cl | 2-(2-Fu) | 4-Me | 2 | 2-(2-Fu) | 4-Me | 2 | —C(Me)$_2$— |
| 325 | Zr | Cl | 2-(2-Fu) | 3-Me | 2 | 2-(2-Fu) | 3-Me | 2 | —C(Me)$_2$— |
| 326 | Zr | Cl | 2-(2-Fu) | 3-Me, 7-Me | 3 | 2-(2-Fu) | 3-Me, 7-Me | 3 | —C(Me)$_2$— |
| 327 | Zr | Cl | 2-(2-Fu) | 4-Me, 7-Me | 3 | 2-(2-Fu) | 4-Me, 7-Me | 3 | —C(Me)$_2$— |
| 328 | Zr | Cl | 2-(2-Fu) | 4-Cl | 2 | 2-(2-Fu) | 4-Cl | 2 | —C(Me)$_2$— |
| 329 | Zr | Cl | 2-(2-Fu) | 4-Et | 2 | 2-(2-Fu) | 4-Et | 2 | —C(Me)$_2$— |
| 330 | Zr | Cl | 2-(2-Fu) | 4-i-Pr | 2 | 2-(2-Fu) | 4-i-Pr | 2 | —C(Me)$_2$— |
| 331 | Zr | Cl | 2-(2-Fu) | 4-t-Bu | 2 | 2-(2-Fu) | 4-t-Bu | 2 | —C(Me)$_2$— |
| 332 | Zr | Cl | 2-(2-Fu) | 4-Ph | 2 | 2-(2-Fu) | 4-Ph | 2 | —C(Me)$_2$— |
| 333 | Zr | Cl | 2-(2-Fu) | 4-Np | 2 | 2-(2-Fu) | 4-Np | 2 | —C(Me)$_2$— |
| 334 | Zr | Cl | 2-(2-Fu) | 4-OMe | 2 | 2-(2-Fu) | 4-OMe | 2 | —C(Me)$_2$— |
| 335 | Zr | Cl | 2-(2-Fu) | 4-OPh | 2 | 2-(2-Fu) | 4-OPh | 2 | —C(Me)$_2$— |
| 336 | Zr | Cl | 2-(2-Fu) | 4-Bzl | 2 | 2-(2-Fu) | 4-Bzl | 2 | —C(Me)$_2$— |
| 337 | Zr | Cl | 2-(2-Fu) | 4-Tol | 2 | 2-(2-Fu) | 4-Tol | 2 | —C(Me)$_2$— |
| 338 | Zr | Cl | 2-(2-Fu) | 4-OBzl | 2 | 2-(2-Fu) | 4-OBzl | 2 | —C(Me)$_2$— |
| 339 | Zr | Cl | 2-(2-Fu) | 4-TMS | 2 | 2-(2-Fu) | 4-TMS | 2 | —C(Me)$_2$— |
| 340 | Zr | Cl | 2-(2-Fu) | 4-(1-Pyr) | 2 | 2-(2-Fu) | 4-(1-Pyr) | 2 | —C(Me)$_2$— |
| 341 | Zr | Cl | 2-(2-Fu) | 4-(1-Indo) | 2 | 2-(2-Fu) | 4-(1-Indo) | 2 | —C(Et)$_2$— |
| 342 | Zr | Cl | 2-(2-Fu), 4-(2-Fu) | — | 2 | 2-(2-Fu), 4-(2-Fu) | — | 2 | —C(Ph)$_2$— |
| 343 | Zr | Cl | 2-(2-Fu), 4-(2-Thie) | — | 2 | 2-(2-Fu), 4-(2-Thie) | — | 2 | —C(Me)$_2$— |
| 344 | Zr | Cl | 2-(2-Fu), 4-(2-BzFu) | — | 2 | 2-(2-Fu), 4-(2-BzFu) | — | 2 | —C(Me)$_2$— |
| 345 | Zr | Cl | 2-(2-Fu), 4-(2-Py) | — | 2 | 2-(2-Fu), 4-(2-Py) | — | 2 | —C(Me)$_2$— |
| 346 | Zr | Cl | 2-(2-Fu), 4-(1-MePyr) | — | 2 | 2-(2-Fu), 4-(1-MePyr) | — | 2 | —C(Me)$_2$— |
| 347 | Zr | Cl | 2-(2-Fu) | 4-Et, 7-Et | 3 | 2-(2-Fu) | 4-Et, 7-Et | 3 | —C(Me)$_2$— |
| 348 | Zr | Cl | 2-(2-Fu) | 4-i-Pr, 7-i-Pr | 3 | 2-(2-Fu) | 4-i-Pr, 7-i-Pr | 3 | —C(Me)$_2$— |
| 349 | Zr | Cl | 2-(2-Fu) | 4-t-Bu, 7-t-Bu | 3 | 2-(2-Fu) | 4-t-Bu, 7-t-Bu | 3 | —C(Me)$_2$— |
| 350 | Zr | Cl | 2-(2-Fu) | 4-Ph, 7-Ph | 3 | 2-(2-Fu) | 4-Ph, 7-Ph | 3 | —C(Me)$_2$— |
| 351 | Zr | Cl | 2-(2-Fu) | 3-Ph, 7-Me | 3 | 2-(2-Fu) | 3-Ph, 7-Me | 3 | —C(Me)$_2$— |
| 352 | Zr | Cl | 2-(2-Fu) | 4-Me, 7-Me | 3 | 2-(2-Fu) | 4-Me, 7-Me | 3 | —C(Et)$_2$— |
| 353 | Zr | Cl | 2-(2-Fu) | 4-Me, 7-Me | 3 | 2-(2-Fu) | 4-Me, 7-Me | 3 | —C(Ph)$_2$— |
| 354 | Zr | Me | 2-(2-Fu) | 4-Ph | 2 | 2-(2-Fu) | 4-Ph | 2 | —C(Me)$_2$— |
| 355 | Zr | Bzl | 2-(2-Fu) | 4-Ph | 2 | 2-(2-Fu) | 4-Ph | 2 | —C(Me)$_2$— |
| 356 | Hf | Cl | 2-(2-Fu) | 4-Ph | 2 | 2-(2-Fu) | 4-Ph | 2 | —C(Me)$_2$— |
| 357 | Ti | Cl | 2-(2-Fu) | 4-Ph | 2 | 2-(2-Fu) | 4-Ph | 2 | —C(Me)$_2$— |
| 358 | Hf | Cl | 2-(2-Fu) | 3-Me, 7-Me | 3 | 2-(2-Fu) | 3-Me, 7-Me | 3 | —C(Me)$_2$— |
| 359 | Ti | Cl | 2-(2-Fu) | 3-Me, 7-Me | 3 | 2-(2-Fu) | 3-Me, 7-Me | 3 | —C(Me)$_2$— |
| 360 | Zr | Cl | 2-(3-Fu) | 4-Ph | 2 | 2-(3-Fu) | 4-Ph | 2 | —C(Me)$_2$— |
| 361 | Zr | Cl | 2-(3-Fu) | 4-Ph | 2 | 2-(3-Fu) | 4-Ph | 2 | —C(Me)$_2$— |
| 362 | Zr | Cl | 2-[2-(3-Me—Fu)] | 4-Ph | 2 | 2-[2-(3-Me—Fu)] | 4-Ph | 2 | —C(Me)$_2$— |
| 363 | Zr | Cl | 2-[2-(3-Me—Fu)] | — | 1 | 2-[2-(3-Me—Fu)] | — | 1 | —C(Me)$_2$— |
| 364 | Zr | Cl | 2-(2-Thie) | 4-Ph | 2 | 2-(2-Thie) | 4-Ph | 2 | —C(Me)$_2$— |
| 365 | Zr | Cl | 2-(2-Thie) | — | 1 | 2-(2-Thie) | — | 1 | —C(Me)$_2$— |
| 366 | Zr | Cl | 2-(2-Py) | 4-Ph | 2 | 2-(2-Py) | 4-Ph | 2 | —C(Me)$_2$— |
| 367 | Zr | Cl | 2-(2-Py) | — | 1 | 2-(2-Py) | — | 1 | —C(Me)$_2$— |
| 368 | Zr | Cl | 2-(2-BzFu) | 4-Ph | 2 | 2-(2-BzFu) | 4-Ph | 2 | —C(Me)$_2$— |
| 369 | Zr | Cl | 2-(2-BzFu) | — | 1 | 2-(2-BzFu) | — | 1 | —C(Me)$_2$— |
| 370 | Zr | Cl | 2-[2-(1-Me—Pyr)] | 4-Ph | 2 | 2-[2-(1-Me—Pyr)] | 4-Ph | 2 | —C(Me)$_2$— |
| 371 | Zr | Cl | 2-[2-(1-Me—Pyr)] | — | 1 | 2-[2-(1-Me—Pyr)] | — | 1 | —C(Me)$_2$— |

TABLE 11

| No. | M | X | CA¹: Indenyl Ra | R¹ | p + m | CA²: Indenyl Ra | R¹ | q + n | Y |
|---|---|---|---|---|---|---|---|---|---|
| 372 | Zr | Cl | 2-(2-Fu) | — | 1 | 2-(2-Fu) | — | 1 | —CH$_2$CH$_2$— |
| 373 | Zr | Cl | 2-(2-Fu) | — | 1 | 2-(2-Fu) | — | 1 | —C$_2$(Me)$_4$— |
| 374 | Zr | Cl | 2-(2-Fu) | 7-Me | 2 | 2-(2-Fu) | 7-Me | 2 | —C$_2$(Me)$_4$— |
| 375 | Zr | Cl | 2-(2-Fu) | 4-Me | 2 | 2-(2-Fu) | 4-Me | 2 | —C$_2$(Me)$_4$— |
| 376 | Zr | Cl | 2-(2-Fu) | 3-Me | 2 | 2-(2-Fu) | 3-Me | 2 | —C$_2$(Me)$_4$— |
| 377 | Zr | Cl | 2-(2-Fu) | 3-Me, 7-Me | 3 | 2-(2-Fu) | 3-Me, 7-Me | 3 | —C$_2$(Me)$_4$— |
| 378 | Zr | Cl | 2-(2-Fu) | 4-Me, 7-Me | 3 | 2-(2-Fu) | 4-Me, 7-Me | 3 | —C$_2$(Me)$_4$— |
| 379 | Zr | Cl | 2-(2-Fu) | 4-Cl | 2 | 2-(2-Fu) | 4-Cl | 2 | —C$_2$(Me)$_4$— |
| 380 | Zr | Cl | 2-(2-Fu) | 4-Et | 2 | 2-(2-Fu) | 4-Et | 2 | —C$_2$(Me)$_4$— |
| 381 | Zr | Cl | 2-(2-Fu) | 4-i-Pr | 2 | 2-(2-Fu) | 4-i-Pr | 2 | —C$_2$(Me)$_4$— |
| 382 | Zr | Cl | 2-(2-Fu) | 4-t-Bu | 2 | 2-(2-Fu) | 4-t-Bu | 2 | —C$_2$(Me)$_4$— |
| 383 | Zr | Cl | 2-(2-Fu) | 4-Ph | 2 | 2-(2-Fu) | 4-Ph | 2 | —C$_2$(Me)$_4$— |
| 384 | Zr | Cl | 2-(2-Fu) | 4-Np | 2 | 2-(2-Fu) | 4-Np | 2 | —C$_2$(Me)$_4$— |
| 385 | Zr | Cl | 2-(2-Fu) | 4-OMe | 2 | 2-(2-Fu) | 4-OMe | 2 | —C$_2$(Me)$_4$— |
| 386 | Zr | Cl | 2-(2-Fu) | 4-OPh | 2 | 2-(2-Fu) | 4-OPh | 2 | —C$_2$(Me)$_4$— |
| 387 | Zr | Cl | 2-(2-Fu) | 4-Bzl | 2 | 2-(2-Fu) | 4-Bzl | 2 | —C$_2$(Me)$_4$— |
| 388 | Zr | Cl | 2-(2-Fu) | 4-Tol | 2 | 2-(2-Fu) | 4-Tol | 2 | —C$_2$(Me)$_4$— |
| 389 | Zr | Cl | 2-(2-Fu) | 4-OBzl | 2 | 2-(2-Fu) | 4-OBzl | 2 | —C$_2$(Me)$_4$— |
| 390 | Zr | Cl | 2-(2-Fu) | 4-TMS | 2 | 2-(2-Fu) | 4-TMS | 2 | —C$_2$(Me)$_4$— |
| 391 | Zr | Cl | 2-(2-Fu) | 4-(1-Pyr) | 2 | 2-(2-Fu) | 4-(1-Pyr) | 2 | —C$_2$(Me)$_4$— |
| 392 | Zr | Cl | 2-(2-Fu) | 4-(1-Indo) | 2 | 2-(2-Fu) | 4-(1-Indo) | 2 | —C$_2$(Me)$_4$— |
| 393 | Zr | Cl | 2-(2-Fu), 4-(2-Fu) | — | 2 | 2-(2-Fu), 4-(2-Fu) | — | 2 | —C$_2$(Me)$_4$— |
| 394 | Zr | Cl | 2-(2-Fu), 4-(2-Thie) | — | 2 | 2-(2-Fu), 4-(2-Thie) | — | 2 | —C$_2$(Me)$_4$— |
| 395 | Zr | Cl | 2-(2-Fu), 4-(2-BzFu) | — | 2 | 2-(2-Fu), 4-(2-BzFu) | — | 2 | —C$_2$(Me)$_4$— |
| 396 | Zr | Cl | 2-(2-Fu), 4-(2-Py) | — | 2 | 2-(2-Fu), 4-(2-Py) | — | 2 | —C$_2$(Me)$_4$— |
| 397 | Zr | Cl | 2-(2-Fu), 4-(1-MePyr) | — | 2 | 2-(2-Fu), 4-(1-MePyr) | — | 2 | —C$_2$(Me)$_4$— |
| 398 | Zr | Cl | 2-(2-Fu) | 4-Et, 7-Et | 3 | 2-(2-Fu) | 4-Et, 7-Et | 3 | —C$_2$(Me)$_4$— |
| 399 | Zr | Cl | 2-(2-Fu) | 4-i-Pr, 7-i-Pr | 3 | 2-(2-Fu) | 4-i-Pr, 7-i-Pr | 3 | —C$_2$(Me)$_4$— |
| 400 | Zr | Cl | 2-(2-Fu) | 4-t-Bu, 7-t-Bu | 3 | 2-(2-Fu) | 4-t-Bu, 7-t-Bu | 3 | —C$_2$(Me)$_4$— |
| 401 | Zr | Cl | 2-(2-Fu) | 4-Ph, 7-Ph | 3 | 2-(2-Fu) | 4-Ph, 7-Ph | 3 | —C$_2$(Me)$_4$— |
| 402 | Zr | Cl | 2-(2-Fu) | 3-Ph, 7-Me | 3 | 2-(2-Fu) | 3-Ph, 7-Me | 3 | —C$_2$(Me)$_4$— |
| 403 | Zr | Cl | 2-(2-Fu) | 4-Me, 7-Me | 3 | 2-(2-Fu) | 4-Me, 7-Me | 3 | —C$_2$(Et)$_4$— |
| 404 | Zr | Cl | 2-(2-Fu) | 4-Me, 7-Me | 3 | 2-(2-Fu) | 4-Me, 7-Me | 3 | —C$_2$(Ph)$_4$— |
| 405 | Zr | Me | 2-(2-Fu) | 4-Ph | 2 | 2-(2-Fu) | 4-Ph | 2 | —C$_2$(Me)$_4$— |
| 406 | Zr | Bzl | 2-(2-Fu) | 4-Ph | 2 | 2-(2-Fu) | 4-Ph | 2 | —C$_2$(Me)$_4$— |
| 407 | Hf | Cl | 2-(2-Fu) | 4-Ph | 2 | 2-(2-Fu) | 4-Ph | 2 | —C$_2$(Me)$_4$— |
| 408 | Ti | Cl | 2-(2-Fu) | 4-Ph | 2 | 2-(2-Fu) | 4-Ph | 2 | —C$_2$(Me)$_4$— |
| 409 | Hf | Cl | 2-(2-Fu) | 3-Me, 7-Me | 3 | 2-(2-Fu) | 3-Me, 7-Me | 3 | —C$_2$(Me)$_4$— |
| 410 | Ti | Cl | 2-(2-Fu) | 3-Me, 7-Me | 3 | 2-(2-Fu) | 3-Me, 7-Me | 3 | —C$_2$(Me)$_4$— |
| 411 | Zr | Cl | 2-(3-Fu) | 4-Ph | 2 | 2-(3-Fu) | 4-Ph | 2 | —C$_2$(Me)$_4$— |
| 412 | Zr | Cl | 2-(3-Fu) | 4-Ph | 2 | 2-(3-Fu) | 4-Ph | 2 | —C$_2$(Me)$_4$— |
| 413 | Zr | Cl | 2-[2-(3-Me—Fu)] | 4-Ph | 2 | 2-[2-(3-Me—Fu)] | 4-Ph | 2 | —C$_2$(Me)$_4$— |
| 414 | Zr | Cl | 2-[2-(3-Me—Fu)] | — | 1 | 2-[2-(3-Me—Fu)] | — | 1 | —C$_2$(Me)$_4$— |
| 415 | Zr | Cl | 2-(2-Thie) | 4-Ph | 2 | 2-(2-Thie) | 4-Ph | 2 | —C$_2$(Me)$_4$— |
| 416 | Zr | Cl | 2-(2-Thie) | — | 1 | 2-(2-Thie) | — | 1 | —C$_2$(Me)$_4$— |
| 417 | Zr | Cl | 2-(2-Py) | 4-Ph | 2 | 2-(2-Py) | 4-Ph | 2 | —C$_2$(Me)$_4$— |
| 418 | Zr | Cl | 2-(2-Py) | — | 1 | 2-(2-Py) | — | 1 | —C$_2$(Me)$_4$— |
| 419 | Zr | Cl | 2-(2-BzFu) | 4-Ph | 2 | 2-(2-BzFu) | 4-Ph | 2 | —C$_2$(Me)$_4$— |
| 420 | Zr | Cl | 2-(2-BzFu) | — | 1 | 2-(2-BzFu) | — | 1 | —C$_2$(Me)$_4$— |
| 421 | Zr | Cl | 2-[2-(1-Me—Pyr)] | 4-Ph | 2 | 2-[2-(1-Me—Pyr)] | 4-Ph | 2 | —C$_2$(Me)$_4$— |
| 422 | Zr | Cl | 2-[2-(1-Me—Pyr)] | — | 1 | 2-[2-(1-Me—Pyr)] | — | 1 | —C$_2$(Me)$_4$— |

TABLE 12

| No. | M | X | CA¹: Indenyl Ra | R¹ | p + m | CA²: Indenyl Ra | R¹ | q + n | Y |
|---|---|---|---|---|---|---|---|---|---|
| 423 | Zr | Cl | 2-(2-Fu) | — | 1 | 2-(2-Fu) | — | 1 | —SiH$_2$— |
| 424 | Zr | Cl | 2-(2-Fu) | — | 1 | 2-(2-Fu) | — | 1 | —Si(Me)$_2$— |
| 425 | Zr | Cl | 2-(2-Fu) | 7-Me | 2 | 2-(2-Fu) | 7-Me | 2 | —Si(Me)$_2$— |
| 426 | Zr | Cl | 2-(2-Fu) | 4-Me | 2 | 2-(2-Fu) | 4-Me | 2 | —Si(Me)$_2$— |
| 427 | Zr | Cl | 2-(2-Fu) | 3-Me | 2 | 2-(2-Fu) | 3-Me | 2 | —Si(Me)$_2$— |
| 428 | Zr | Cl | 2-(2-Fu) | 3-Me, 7-Me | 3 | 2-(2-Fu) | 3-Me, 7-Me | 3 | —Si(Me)$_2$— |
| 429 | Zr | Cl | 2-(2-Fu) | 4-Me, 7-Me | 3 | 2-(2-Fu) | 4-Me, 7-Me | 3 | —Si(Me)$_2$— |
| 430 | Zr | Cl | 2-(2-Fu) | 4-Cl | 2 | 2-(2-Fu) | 4-Cl | 2 | —Si(Me)$_2$— |
| 431 | Zr | Cl | 2-(2-Fu) | 4-Et | 2 | 2-(2-Fu) | 4-Et | 2 | —Si(Me)$_2$— |
| 432 | Zr | Cl | 2-(2-Fu) | 4-i-Pr | 2 | 2-(2-Fu) | 4-i-Pr | 2 | —Si(Me)$_2$— |
| 433 | Zr | Cl | 2-(2-Fu) | 4-t-Bu | 2 | 2-(2-Fu) | 4-t-Bu | 2 | —Si(Me)$_2$— |
| 434 | Zr | Cl | 2-(2-Fu) | 4-Ph | 2 | 2-(2-Fu) | 4-Ph | 2 | —Si(Me)$_2$— |
| 435 | Zr | Cl | 2-(2-Fu) | 4-Np | 2 | 2-(2-Fu) | 4-Np | 2 | —Si(Me)$_2$— |
| 436 | Zr | Cl | 2-(2-Fu) | 4-OMe | 2 | 2-(2-Fu) | 4-OMe | 2 | —Si(Me)$_2$— |

TABLE 12-continued

| | | | CA¹: Indenyl | | | CA²: Indenyl | | | |
|---|---|---|---|---|---|---|---|---|---|
| No. | M | X | Ra | R¹ | p + m | Ra | R¹ | q + n | Y |
| 437 | Zr | Cl | 2-(2-Fu) | 4-OPh | 2 | 2-(2-Fu) | 4-OPh | 2 | —Si(Me)₂— |
| 438 | Zr | Cl | 2-(2-Fu) | 4-Bzl | 2 | 2-(2-Fu) | 4-Bzl | 2 | —Si(Me)₂— |
| 439 | Zr | Cl | 2-(2-Fu) | 4-Tol | 2 | 2-(2-Fu) | 4-Tol | 2 | —Si(Me)₂— |
| 440 | Zr | Cl | 2-(2-Fu) | 4-OBzl | 2 | 2-(2-Fu) | 4-OBzl | 2 | —Si(Me)₂— |
| 441 | Zr | Cl | 2-(2-Fu) | 4-TMS | 2 | 2-(2-Fu) | 4-TMS | 2 | —Si(Me)₂— |
| 442 | Zr | Cl | 2-(2-Fu) | 4-(1-Pyr) | 2 | 2-(2-Fu) | 4-(1-Pyr) | 2 | —Si(Me)₂— |
| 443 | Zr | Cl | 2-(2-Fu) | 4-(1-Indo) | 2 | 2-(2-Fu) | 4-(1-Indo) | 2 | —Si(Me)₂— |
| 444 | Zr | Cl | 2-(2-Fu), 4-(2-Fu) | — | 2 | 2-(2-Fu), 4-(2-Fu) | — | 2 | —Si(Me)₂— |
| 445 | Zr | Cl | 2-(2-Fu), 4-(2-Thie) | — | 2 | 2-(2-Fu), 4-(2-Thie) | — | 2 | —Si(Me)₂— |
| 446 | Zr | Cl | 2-(2-Fu), 4-(2-BzFu) | — | 2 | 2-(2-Fu), 4-(2-BzFu) | — | 2 | —Si(Me)₂— |
| 447 | Zr | Cl | 2-(2-Fu), 4-(2-Py) | — | 2 | 2-(2-Fu), 4-(2-Py) | — | 2 | —Si(Me)₂— |
| 448 | Zr | Cl | 2-(2-Fu), 4-(1-MePyr) | — | 2 | 2-(2-Fu), 4-(1-MePyr) | — | 2 | —Si(Me)₂— |
| 449 | Zr | Cl | 2-(2-Fu) | 4-Et, 7-Et | 3 | 2-(2-Fu) | 4-Et, 7-Et | 3 | —Si(Me)₂— |
| 450 | Zr | Cl | 2-(2-Fu) | 4-i-Pr, 7-i-Pr | 3 | 2-(2-Fu) | 4-i-Pr, 7-i-Pr | 3 | —Si(Me)₂— |
| 451 | Zr | Cl | 2-(2-Fu) | 4-t-Bu, 7-t-Bu | 3 | 2-(2-Fu) | 4-t-Bu, 7-t-Bu | 3 | —Si(Me)₂— |
| 452 | Zr | Cl | 2-(2-Fu) | 4-Ph, 7-Ph | 3 | 2-(2-Fu) | 4-Ph, 7-Ph | 3 | —Si(Me)₂— |
| 453 | Zr | Cl | 2-(2-Fu) | 3-Ph, 7-Me | 3 | 2-(2-Fu) | 3-Ph, 7-Me | 3 | —Si(Me)₂— |
| 454 | Zr | Cl | 2-(2-Fu) | 4-Me, 7-Me | 3 | 2-(2-Fu) | 4-Me, 7-Me | 3 | —Si(Et)₂— |
| 455 | Zr | Cl | 2-(2-Fu) | 4-Me, 7-Me | 3 | 2-(2-Fu) | 4-Me, 7-Me | 3 | —Si(Ph)₂— |
| 456 | Zr | Me | 2-(2-Fu) | 4-Ph | 2 | 2-(2-Fu) | 4-Ph | 2 | —Si(Me)₂— |
| 457 | Zr | Bzl | 2-(2-Fu) | 4-Ph | 2 | 2-(2-Fu) | 4-Ph | 2 | —Si(Me)₂— |
| 458 | Hf | Cl | 2-(2-Fu) | 4-Ph | 2 | 2-(2-Fu) | 4-Ph | 2 | —Si(Me)₂— |
| 459 | Ti | Cl | 2-(2-Fu) | 4-Ph | 2 | 2-(2-Fu) | 4-Ph | 2 | —Si(Me)₂— |
| 460 | Hf | Cl | 2-(2-Fu) | 3-Me, 7-Me | 3 | 2-(2-Fu) | 3-Me, 7-Me | 3 | —Si(Me)₂— |
| 461 | Ti | Cl | 2-(2-Fu) | 3-Me, 7-Me | 3 | 2-(2-Fu) | 3-Me, 7-Me | 3 | —Si(Me)₂— |
| 462 | Zr | Cl | 2-(3-Fu) | 4-Ph | 2 | 2-(3-Fu) | 4-Ph | 2 | —Si(Me)₂— |
| 463 | Zr | Cl | 2-(3-Fu) | 4-Ph | 2 | 2-(3-Fu) | 4-Ph | 2 | —Si(Me)₂— |
| 464 | Zr | Cl | 2-[2-(3-Me—Fu)] | 4-Ph | 2 | 2-[2-(3-Me—Fu)] | 4-Ph | 2 | —Si(Me)₂— |
| 465 | Zr | Cl | 2-[2-(3-Me—Fu)] | — | 1 | 2-[2-(3-Me—Fu)] | — | 1 | —Si(Me)₂— |
| 466 | Zr | Cl | 2-(2-Thie) | 4-Ph | 2 | 2-(2-Thie) | 4-Ph | 2 | —Si(Me)₂— |
| 467 | Zr | Cl | 2-(2-Thie) | — | 1 | 2-(2-Thie) | — | 1 | —Si(Me)₂— |
| 468 | Zr | Cl | 2-(2-Py) | 4-Ph | 2 | 2-(2-Py) | 4-Ph | 2 | —Si(Me)₂— |
| 469 | Zr | Cl | 2-(2-Py) | — | 1 | 2-(2-Py) | — | 1 | —Si(Me)₂— |
| 470 | Zr | Cl | 2-(2-BzFu) | 4-Ph | 2 | 2-(2-BzFu) | 4-Ph | 2 | —Si(Me)₂— |
| 471 | Zr | Cl | 2-(2-BzFu) | — | 1 | 2-(2-BzFu) | — | 1 | —Si(Me)₂— |
| 472 | Zr | Cl | 2-[2-(1-Me—Pyr)] | 4-Ph | 2 | 2-[2-(1-Me—Pyr)] | 4-Ph | 2 | —Si(Me)₂— |
| 473 | Zr | Cl | 2-[2-(1-Me—Pyr)] | — | 1 | 2-[2-(1-Me—Pyr)] | — | 1 | —Si(Me)₂— |

TABLE 13

| | | | CA¹: Indenyl | | | CA²: Indenyl | | | |
|---|---|---|---|---|---|---|---|---|---|
| No. | M | X | Ra¹ | R¹ | p + m | Ra² | R¹ | q + n | Y |
| 474 | Zr | Cl | 2-(2-Fu) | — | 1 | 2-(2-Fu) | — | 1 | —GeH₂— |
| 475 | Zr | Cl | 2-(2-Fu) | — | 1 | 2-(2-Fu) | — | 1 | —Ge(Me)₂— |
| 476 | Zr | Cl | 2-(2-Fu) | 7-Me | 2 | 2-(2-Fu) | 7-Me | 2 | —Ge(Me)₂— |
| 477 | Zr | Cl | 2-(2-Fu) | 4-Me | 2 | 2-(2-Fu) | 4-Me | 2 | —Ge(Me)₂— |
| 478 | Zr | Cl | 2-(2-Fu) | 3-Me | 2 | 2-(2-Fu) | 3-Me | 2 | —Ge(Me)₂— |
| 479 | Zr | Cl | 2-(2-Fu) | 3-Me, 7-Me | 3 | 2-(2-Fu) | 3-Me, 7-Me | 3 | —Ge(Me)₂— |
| 480 | Zr | Cl | 2-(2-Fu) | 4-Me, 7-Me | 3 | 2-(2-Fu) | 4-Me, 7-Me | 3 | —Ge(Me)₂— |
| 481 | Zr | Cl | 2-(2-Fu) | 4-Cl | 2 | 2-(2-Fu) | 4-Cl | 2 | —Ge(Me)₂— |
| 482 | Zr | Cl | 2-(2-Fu) | 4-Et | 2 | 2-(2-Fu) | 4-Et | 2 | —Ge(Me)₂— |
| 483 | Zr | Cl | 2-(2-Fu) | 4-i-Pr | 2 | 2-(2-Fu) | 4-i-Pr | 2 | —Ge(Me)₂— |
| 484 | Zr | Cl | 2-(2-Fu) | 4-t-Bu | 2 | 2-(2-Fu) | 4-t-Bu | 2 | —Ge(Me)₂— |
| 485 | Zr | Cl | 2-(2-Fu) | 4-Ph | 2 | 2-(2-Fu) | 4-Ph | 2 | —Ge(Me)₂— |
| 486 | Zr | Cl | 2-(2-Fu) | 4-Np | 2 | 2-(2-Fu) | 4-Np | 2 | —Ge(Me)₂— |
| 487 | Zr | Cl | 2-(2-Fu) | 4-OMe | 2 | 2-(2-Fu) | 4-OMe | 2 | —Ge(Me)₂— |
| 488 | Zr | Cl | 2-(2-Fu) | 4-OPh | 2 | 2-(2-Fu) | 4-OPh | 2 | —Ge(Me)₂— |
| 489 | Zr | Cl | 2-(2-Fu) | 4-Bzl | 2 | 2-(2-Fu) | 4-Bzl | 2 | —Ge(Me)₂— |
| 490 | Zr | Cl | 2-(2-Fu) | 4-Tol | 2 | 2-(2-Fu) | 4-Tol | 2 | —Ge(Me)₂— |
| 491 | Zr | Cl | 2-(2-Fu) | 4-OBzl | 2 | 2-(2-Fu) | 4-OBzl | 2 | —Ge(Me)₂— |
| 492 | Zr | Cl | 2-(2-Fu) | 4-TMS | 2 | 2-(2-Fu) | 4-TMS | 2 | —Ge(Me)₂— |
| 493 | Zr | Cl | 2-(2-Fu) | 4-(1-Pyr) | 2 | 2-(2-Fu) | 4-(1-Pyr) | 2 | —Ge(Me)₂— |
| 494 | Zr | Cl | 2-(2-Fu) | 4-(1-Indo) | 2 | 2-(2-Fu) | 4-(1-Indo) | 2 | —Ge(Me)₂— |
| 495 | Zr | Cl | 2-(2-Fu), 4-(2-Fu) | — | 2 | 2-(2-Fu), 4-(2-Fu) | — | 2 | —Ge(Me)₂— |
| 496 | Zr | Cl | 2-(2-Fu), 4-(2-Thie) | — | 2 | 2-(2-Fu), 4-(2-Thie) | — | 2 | —Ge(Me)₂— |
| 497 | Zr | Cl | 2-(2-Fu), 4-(2-BzFu) | — | 2 | 2-(2-Fu), 4-(2-BzFu) | — | 2 | —Ge(Me)₂— |
| 498 | Zr | Cl | 2-(2-Fu), 4-(2-Py) | — | 2 | 2-(2-Fu), 4-(2-Py) | — | 2 | —Ge(Me)₂— |
| 499 | Zr | Cl | 2-(2-Fu), 4-(1-MePyr) | — | 2 | 2-(2-Fu), 4-(1-MePyr) | — | 2 | —Ge(Me)₂— |
| 500 | Zr | Cl | 2-(2-Fu) | 4-Et, 7-Et | 3 | 2-(2-Fu) | 4-Et, 7-Et | 3 | —Ge(Me)₂— |
| 501 | Zr | Cl | 2-(2-Fu) | 4-i-Pr, 7-i-Pr | 3 | 2-(2-Fu) | 4-i-Pr, 7-i-Pr | 3 | —Ge(Me)₂— |

TABLE 13-continued

|  |  |  | CA¹: Indenyl | | | CA²: Indenyl | | | |
|---|---|---|---|---|---|---|---|---|---|
| No. | M | X | Ra¹ | R¹ | p + m | Ra² | R¹ | q + n | Y |
| 502 | Zr | Cl | 2-(2-Fu) | 4-t-Bu, 7-t-Bu | 3 | 2-(2-Fu) | 4-t-Bu, 7-t-Bu | 3 | —Ge(Me)₂— |
| 503 | Zr | Cl | 2-(2-Fu) | 4-Ph, 7-Ph | 3 | 2-(2-Fu) | 4-Ph, 7-Ph | 3 | —Ge(Me)₂— |
| 504 | Zr | Cl | 2-(2-Fu) | 3-Ph, 7-Me | 3 | 2-(2-Fu) | 3-Ph, 7-Me | 3 | —Ge(Me)₂— |
| 505 | Zr | Cl | 2-(2-Fu) | 4-Me, 7-Me | 3 | 2-(2-Fu) | 4-Me, 7-Me | 3 | —Ge(Et)₂— |
| 506 | Zr | Cl | 2-(2-Fu) | 4-Me, 7-Me | 3 | 2-(2-Fu) | 4-Me, 7-Me | 3 | —Ge(Ph)₂— |
| 507 | Zr | Me | 2-(2-Fu) | 4-Ph | 2 | 2-(2-Fu) | 4-Ph | 2 | —Ge(Me)₂— |
| 508 | Zr | Bzl | 2-(2-Fu) | 4-Ph | 2 | 2-(2-Fu) | 4-Ph | 2 | —Ge(Me)₂— |
| 509 | Hf | Cl | 2-(2-Fu) | 4-Ph | 2 | 2-(2-Fu) | 4-Ph | 2 | —Ge(Me)₂— |
| 510 | Ti | Cl | 2-(2-Fu) | 4-Ph | 2 | 2-(2-Fu) | 4-Ph | 2 | —Ge(Me)₂— |
| 511 | Hf | Cl | 2-(2-Fu) | 3-Me, 7-Me | 3 | 2-(2-Fu) | 3-Me, 7-Me | 3 | —Ge(Me)₂— |
| 512 | Ti | Cl | 2-(2-Fu) | 3-Me, 7-Me | 3 | 2-(2-Fu) | 3-Me, 7-Me | 3 | —Ge(Me)₂— |
| 513 | Zr | Cl | 2-(3-Fu) | 4-Ph | 2 | 2-(3-Fu) | 4-Ph | 2 | —Ge(Me)₂— |
| 514 | Zr | Cl | 2-(3-Fu) | 4-Ph | 2 | 2-(3-Fu) | 4-Ph | 2 | —Ge(Me)₂— |
| 515 | Zr | Cl | 2-[2-(3-Me—Fu)] | 4-Ph | 2 | 2-[2-(3-Me—Fu)] | 4-Ph | 2 | —Ge(Me)₂— |
| 516 | Zr | Cl | 2-[2-(3-Me—Fu)] | — | 1 | 2-[2-(3-Me—Fu)] | — | 1 | —Ge(Me)₂— |
| 517 | Zr | Cl | 2-(2-Thie) | 4-Ph | 2 | 2-(2-Thie) | 4-Ph | 2 | —Ge(Me)₂— |
| 518 | Zr | Cl | 2-(2-Thie) | — | 1 | 2-(2-Thie) | — | 1 | —Ge(Me)₂— |
| 519 | Zr | Cl | 2-(2-Py) | 4-Ph | 2 | 2-(2-Py) | 4-Ph | 2 | —Ge(Me)₂— |
| 520 | Zr | Cl | 2-(2-Py) | — | 1 | 2-(2-Py) | — | 1 | —Ge(Me)₂— |
| 521 | Zr | Cl | 2-(2-BzFu) | 4-Ph | 2 | 2-(2-BzFu) | 4-Ph | 2 | —Ge(Me)₂— |
| 522 | Zr | Cl | 2-(2-BzFu) | — | 1 | 2-(2-BzFu) | — | 1 | —Ge(Me)₂— |
| 523 | Zr | Cl | 2-[2-(1-Me—Pyr)] | 4-Ph | 2 | 2-[2-(1-Me—Pyr)] | 4-Ph | 2 | —Ge(Me)₂— |
| 524 | Zr | Cl | 2-[2-(1-Me—Pyr)] | — | 1 | 2-[2-(1-Me—Pyr)] | — | 1 | —Ge(Me)₂— |

TABLE 14

|  |  |  | CA¹: Tetrahydroindenyl | | | CA²: Tetrahydroindenyl | | | |
|---|---|---|---|---|---|---|---|---|---|
| No. | M | X | Ra | R¹ | p + m | Ra | R¹ | q + n | Y |
| 525 | Zr | Cl | 2-(2-Fu) | — | 1 | 2-(2-Fu) | — | 1 | —CH₂— |
| 526 | Zr | Cl | 2-(2-Fu) | — | 1 | 2-(2-Fu) | — | 1 | —C(Me)₂— |
| 527 | Zr | Cl | 2-(2-Fu) | 7-Me | 2 | 2-(2-Fu) | 7-Me | 2 | —C(Me)₂— |
| 528 | Zr | Cl | 2-(2-Fu) | 4-Me | 2 | 2-(2-Fu) | 4-Me | 2 | —C(Me)₂— |
| 529 | Zr | Cl | 2-(2-Fu) | 3-Me | 2 | 2-(2-Fu) | 3-Me | 2 | —C(Me)₂— |
| 530 | Zr | Cl | 2-(2-Fu) | 3-Me, 7-Me | 3 | 2-(2-Fu) | 3-Me, 7-Me | 3 | —C(Me)₂— |
| 531 | Zr | Cl | 2-(2-Fu) | 4-Me, 7-Me | 3 | 2-(2-Fu) | 4-Me, 7-Me | 3 | —C(Me)₂— |
| 532 | Zr | Cl | 2-(2-Fu) | 4-Cl | 2 | 2-(2-Fu) | 4-Cl | 2 | —C(Me)₂— |
| 533 | Zr | Cl | 2-(2-Fu) | 4-Et | 2 | 2-(2-Fu) | 4-Et | 2 | —C(Me)₂— |
| 534 | Zr | Cl | 2-(2-Fu) | 4-i-Pr | 2 | 2-(2-Fu) | 4-i-Pr | 2 | —C(Me)₂— |
| 535 | Zr | Cl | 2-(2-Fu) | 4-t-Bu | 2 | 2-(2-Fu) | 4-t-Bu | 2 | —C(Me)₂— |
| 536 | Zr | Cl | 2-(2-Fu) | 4-Ph | 2 | 2-(2-Fu) | 4-Ph | 2 | —C(Me)₂— |
| 537 | Zr | Cl | 2-(2-Fu) | 4-Np | 2 | 2-(2-Fu) | 4-Np | 2 | —C(Me)₂— |
| 538 | Zr | Cl | 2-(2-Fu) | 4-OMe | 2 | 2-(2-Fu) | 4-OMe | 2 | —C(Me)₂— |
| 539 | Zr | Cl | 2-(2-Fu) | 4-OPh | 2 | 2-(2-Fu) | 4-OPh | 2 | —C(Me)₂— |
| 540 | Zr | Cl | 2-(2-Fu) | 4-Bzl | 2 | 2-(2-Fu) | 4-Bzl | 2 | —C(Me)₂— |
| 541 | Zr | Cl | 2-(2-Fu) | 4-Tol | 2 | 2-(2-Fu) | 4-Tol | 2 | —C(Me)₂— |
| 542 | Zr | Cl | 2-(2-Fu) | 4-OBzl | 2 | 2-(2-Fu) | 4-OBzl | 2 | —C(Me)₂— |
| 543 | Zr | Cl | 2-(2-Fu) | 4-TMS | 2 | 2-(2-Fu) | 4-TMS | 2 | —C(Me)₂— |
| 544 | Zr | Cl | 2-(2-Fu) | 4-(1-Pyr) | 2 | 2-(2-Fu) | 4-(1-Pyr) | 2 | —C(Me)₂— |
| 545 | Zr | Cl | 2-(2-Fu) | 4-(1-Indo) | 2 | 2-(2-Fu) | 4-(1-Indo) | 2 | —C(Me)₂— |
| 546 | Zr | Cl | 2-(2-Fu), 4-(2-Fu) | — | 2 | 2-(2-Fu), 4-(2-Fu) | — | 2 | —C(Me)₂— |
| 547 | Zr | Cl | 2-(2-Fu), 4-(2-Thie) | — | 2 | 2-(2-Fu), 4-(2-Thie) | — | 2 | —C(Me)₂— |
| 548 | Zr | Cl | 2-(2-Fu), 4-(2-BzFu) | — | 2 | 2-(2-Fu), 4-(2-BzFu) | — | 2 | —C(Me)₂— |
| 549 | Zr | Cl | 2-(2-Fu), 4-(2-Py) | — | 2 | 2-(2-Fu), 4-(2-Py) | — | 2 | —C(Me)₂— |
| 550 | Zr | Cl | 2-(2-Fu), 4-(1-MePyr) | — | 2 | 2-(2-Fu), 4-(1-MePyr) | — | 2 | —C(Me)₂— |
| 551 | Zr | Cl | 2-(2-Fu) | 4-Et, 7-Et | 3 | 2-(2-Fu) | 4-Et, 7-Et | 3 | —C(Me)₂— |
| 552 | Zr | Cl | 2-(2-Fu) | 4-i-Pr, 7-i-Pr | 3 | 2-(2-Fu) | 4-i-Pr, 7-i-Pr | 3 | —C(Me)₂— |
| 553 | Zr | Cl | 2-(2-Fu) | 4-t-Bu, 7-t-Bu | 3 | 2-(2-Fu) | 4-t-Bu, 7-t-Bu | 3 | —C(Me)₂— |
| 554 | Zr | Cl | 2-(2-Fu) | 4-Ph, 7-Ph | 3 | 2-(2-Fu) | 4-Ph, 7-Ph | 3 | —C(Me)₂— |
| 555 | Zr | Cl | 2-(2-Fu) | 3-Ph, 7-Me | 3 | 2-(2-Fu) | 3-Ph, 7-Me | 3 | —C(Me)₂— |
| 556 | Zr | Cl | 2-(2-Fu) | 4-Me, 7-Me | 3 | 2-(2-Fu) | 4-Me, 7-Me | 3 | —C(Et)₂— |
| 557 | Zr | Cl | 2-(2-Fu) | 4-Me, 7-Me | 3 | 2-(2-Fu) | 4-Me, 7-Me | 3 | —C(Ph)₂— |
| 558 | Zr | Me | 2-(2-Fu) | 4-Ph | 2 | 2-(2-Fu) | 4-Ph | 2 | —C(Me)₂— |
| 559 | Zr | Bzl | 2-(2-Fu) | 4-Ph | 2 | 2-(2-Fu) | 4-Ph | 2 | —C(Me)₂— |
| 560 | Hf | Cl | 2-(2-Fu) | 4-Ph | 2 | 2-(2-Fu) | 4-Ph | 2 | —C(Me)₂— |
| 561 | Ti | Cl | 2-(2-Fu) | 4-Ph | 2 | 2-(2-Fu) | 4-Ph | 2 | —C(Me)₂— |
| 562 | Hf | Cl | 2-(2-Fu) | 3-Me, 7-Me | 3 | 2-(2-Fu) | 3-Me, 7-Me | 3 | —C(Me)₂— |
| 563 | Ti | Cl | 2-(2-Fu) | 3-Me, 7-Me | 3 | 2-(2-Fu) | 3-Me, 7-Me | 3 | —C(Me)₂— |
| 564 | Zr | Cl | 2-(3-Fu) | 4-Ph | 2 | 2-(3-Fu) | 4-Ph | 2 | —C(Me)₂— |
| 565 | Zr | Cl | 2-(3-Fu) | 4-Ph | 2 | 2-(3-Fu) | 4-Ph | 2 | —C(Me)₂— |
| 566 | Zr | Cl | 2-[2-(3-Me—Fu)] | 4-Ph | 2 | 2-[2-(3-Me—Fu)] | 4-Ph | 2 | —C(Me)₂— |

TABLE 14-continued

|  |  |  | CA¹: Tetrahydroindenyl | | | CA²: Tetrahydroindenyl | | | |
| --- | --- | --- | --- | --- | --- | --- | --- | --- | --- |
| No. | M | X | Ra | R¹ | p + m | Ra | R¹ | q + n | Y |
| 567 | Zr | Cl | 2-[2-(3-Me—Fu)] | — | 1 | 2-[2-(3-Me—Fu)] | — | 1 | —C(Me)$_2$— |
| 568 | Zr | Cl | 2-(2-Thie) | 4-Ph | 2 | 2-(2-Thie) | 4-Ph | 2 | —C(Me)$_2$— |
| 569 | Zr | Cl | 2-(2-Thie) | — | 1 | 2-(2-Thie) | — | 1 | —C(Me)$_2$— |
| 570 | Zr | Cl | 2-(2-Py) | 4-Ph | 2 | 2-(2-Py) | 4-Ph | 2 | —C(Me)$_2$— |
| 571 | Zr | Cl | 2-(2-Py) | — | 1 | 2-(2-Py) | — | 1 | —C(Me)$_2$— |
| 572 | Zr | Cl | 2-(2-BzFu) | 4-Ph | 2 | 2-(2-BzFu) | 4-Ph | 2 | —C(Me)$_2$— |
| 573 | Zr | Cl | 2-(2-BzFu) | — | 1 | 2-(2-BzFu) | — | 1 | —C(Me)$_2$— |
| 574 | Zr | Cl | 2-[2-(1-Me—Pyr)] | 4-Ph | 2 | 2-[2-(1-Me—Pyr)] | 4-Ph | 2 | —C(Me)$_2$— |
| 575 | Zr | Cl | 2-[2-(1-Me—Pyr)] | — | 1 | 2-[2-(1-Me—Pyr)] | — | 1 | —C(Me)$_2$— |

TABLE 15

|  |  |  | CA¹: Tetrahydroindenyl | | | CA²: Tetrahydroindenyl | | | |
| --- | --- | --- | --- | --- | --- | --- | --- | --- | --- |
| No. | M | X | Ra | R¹ | p + m | Ra | R¹ | q + n | Y |
| 576 | Zr | Cl | 2-(2-Fu) | — | 1 | 2-(2-Fu) | — | 1 | —CH$_2$CH$_2$— |
| 577 | Zr | Cl | 2-(2-Fu) | — | 1 | 2-(2-Fu) | — | 1 | —C$_2$(Me)$_4$— |
| 578 | Zr | Cl | 2-(2-Fu) | 7-Me | 2 | 2-(2-Fu) | 7-Me | 2 | —C$_2$(Me)$_4$— |
| 579 | Zr | Cl | 2-(2-Fu) | 4-Me | 2 | 2-(2-Fu) | 4-Me | 2 | —C$_2$(Me)$_4$— |
| 580 | Zr | Cl | 2-(2-Fu) | 3-Me | 2 | 2-(2-Fu) | 3-Me | 2 | —C$_2$(Me)$_4$— |
| 581 | Zr | Cl | 2-(2-Fu) | 3-Me, 7-Me | 3 | 2-(2-Fu) | 3-Me, 7-Me | 3 | —C$_2$(Me)$_4$— |
| 582 | Zr | Cl | 2-(2-Fu) | 4-Me, 7-Me | 3 | 2-(2-Fu) | 4-Me, 7-Me | 3 | —C$_2$(Me)$_4$— |
| 583 | Zr | Cl | 2-(2-Fu) | 4-Cl | 2 | 2-(2-Fu) | 4-Cl | 2 | —C$_2$(Me)$_4$— |
| 584 | Zr | Cl | 2-(2-Fu) | 4-Et | 2 | 2-(2-Fu) | 4-Et | 2 | —C$_2$(Me)$_4$— |
| 585 | Zr | Cl | 2-(2-Fu) | 4-I—Pr | 2 | 2-(2-Fu) | 4-I—Pr | 2 | —C$_2$(Me)$_4$— |
| 586 | Zr | Cl | 2-(2-Fu) | 4-t-Bu | 2 | 2-(2-Fu) | 4-t-Bu | 2 | —C$_2$(Me)$_4$— |
| 587 | Zr | Cl | 2-(2-Fu) | 4-Ph | 2 | 2-(2-Fu) | 4-Ph | 2 | —C$_2$(Me)$_4$— |
| 588 | Zr | Cl | 2-(2-Fu) | 4-Np | 2 | 2-(2-Fu) | 4-Np | 2 | —C$_2$(Me)$_4$— |
| 589 | Zr | Cl | 2-(2-Fu) | 4-OMe | 2 | 2-(2-Fu) | 4-OMe | 2 | —C$_2$(Me)$_4$— |
| 590 | Zr | Cl | 2-(2-Fu) | 4-OPh | 2 | 2-(2-Fu) | 4-OPh | 2 | —C$_2$(Me)$_4$— |
| 591 | Zr | Cl | 2-(2-Fu) | 4-Bzl | 2 | 2-(2-Fu) | 4-Bzl | 2 | —C$_2$(Me)$_4$— |
| 592 | Zr | Cl | 2-(2-Fu) | 4-Tol | 2 | 2-(2-Fu) | 4-Tol | 2 | —C$_2$(Me)$_4$— |
| 593 | Zr | Cl | 2-(2-Fu) | 4-OBzl | 2 | 2-(2-Fu) | 4-OBzl | 2 | —C$_2$(Me)$_4$— |
| 594 | Zr | Cl | 2-(2-Fu) | 4-TMS | 2 | 2-(2-Fu) | 4-TMS | 2 | —C$_2$(Me)$_4$— |
| 595 | Zr | Cl | 2-(2-Fu) | 4-(1-Pyr) | 2 | 2-(2-Fu) | 4-(1-Pyr) | 2 | —C$_2$(Me)$_4$— |
| 596 | Zr | Cl | 2-(2-Fu) | 4-(1-Indo) | 2 | 2-(2-Fu) | 4-(1-Indo) | 2 | —C$_2$(Me)$_4$— |
| 597 | Zr | Cl | 2-(2-Fu), 4-(2-Fu) | — | 2 | 2-(2-Fu), 4-(2-Fu) | — | 2 | —C$_2$(Me)$_4$— |
| 598 | Zr | Cl | 2-(2-Fu), 4-(2-Thie) | — | 2 | 2-(2-Fu), 4-(2-Thie) | — | 2 | —C$_2$(Me)$_4$— |
| 599 | Zr | Cl | 2-(2-Fu), 4-(2-BzFu) | — | 2 | 2-(2-Fu), 4-(2-BzFu) | — | 2 | —C$_2$(Me)$_4$— |
| 600 | Zr | Cl | 2-(2-Fu), 4-(2-Py) | — | 2 | 2-(2-Fu), 4-(2-Py) | — | 2 | —C$_2$(Me)$_4$— |
| 601 | Zr | Cl | 2-(2-Fu), 4-(1-MePyr) | — | 2 | 2-(2-Fu), 4-(1-MePyr) | — | 2 | —C$_2$(Me)$_4$— |
| 602 | Zr | Cl | 2-(2-Fu) | 4-Et, 7-Et | 3 | 2-(2-Fu) | 4-Et, 7-Et | 3 | —C$_2$(Me)$_4$— |
| 603 | Zr | Cl | 2-(2-Fu) | 4-I—Pr, 7-I—Pr | 3 | 2-(2-Fu) | 4-I—Pr, 7-I—Pr | 3 | —C$_2$(Me)$_4$— |
| 604 | Zr | Cl | 2-(2-Fu) | 4-t-Bu, 7-t-Bu | 3 | 2-(2-Fu) | 4-t-Bu, 7-t-Bu | 3 | —C$_2$(Me)$_4$— |
| 605 | Zr | Cl | 2-(2-Fu) | 4-Ph, 7-Ph | 3 | 2-(2-Fu) | 4-Ph, 7-Ph | 3 | —C$_2$(Me)$_4$— |
| 606 | Zr | Cl | 2-(2-Fu) | 3-Ph, 7-Me | 3 | 2-(2-Fu) | 3-Ph, 7-Me | 3 | —C$_2$(Me)$_4$— |
| 607 | Zr | Cl | 2-(2-Fu) | 4-Me, 7-Me | 3 | 2-(2-Fu) | 4-Me, 7-Me | 3 | —C$_2$(Et)$_4$— |
| 608 | Zr | Cl | 2-(2-Fu) | 4-Me, 7-Me | 3 | 2-(2-Fu) | 4-Me, 7-Me | 3 | —C$_2$(Ph)$_4$— |
| 609 | Zr | Me | 2-(2-Fu) | 4-Ph | 2 | 2-(2-Fu) | 4-Ph | 2 | —C$_2$(Me)$_4$— |
| 610 | Zr | Bzl | 2-(2-Fu) | 4-Ph | 2 | 2-(2-Fu) | 4-Ph | 2 | —C$_2$(Me)$_4$— |
| 611 | Hf | Cl | 2-(2-Fu) | 4-Ph | 2 | 2-(2-Fu) | 4-Ph | 2 | —C$_2$(Me)$_4$— |
| 612 | Ti | Cl | 2-(2-Fu) | 4-Ph | 2 | 2-(2-Fu) | 4-Ph | 2 | —C$_2$(Me)$_4$— |
| 613 | Hf | Cl | 2-(2-Fu) | 3-Me, 7-Me | 3 | 2-(2-Fu) | 3-Me, 7-Me | 3 | —C$_2$(Me)$_4$— |
| 614 | Ti | Cl | 2-(2-Fu) | 3-Me, 7-Me | 3 | 2-(2-Fu) | 3-Me, 7-Me | 3 | —C$_2$(Me)$_4$— |
| 615 | Zr | Cl | 2-(3-Fu) | 4-Ph | 2 | 2-(3-Fu) | 4-Ph | 2 | —C$_2$(Me)$_4$— |
| 616 | Zr | Cl | 2-(3-Fu) | 4-Ph | 2 | 2-(3-Fu) | 4-Ph | 2 | —C$_2$(Me)$_4$— |
| 617 | Zr | Cl | 2-[2-(3-Me—Fu)] | 4-Ph | 2 | 2-[2-(3-Me—Fu)] | 4-Ph | 2 | —C$_2$(Me)$_4$— |
| 618 | Zr | Cl | 2-[2-(3-Me—Fu)] | — | 1 | 2-[2-(3-Me—Fu)] | — | 1 | —C$_2$(Me)$_4$— |
| 619 | Zr | Cl | 2-(2-Thie) | 4-Ph | 2 | 2-(2-Thie) | 4-Ph | 2 | —C$_2$(Me)$_4$— |
| 620 | Zr | Cl | 2-(2-Thie) | — | 1 | 2-(2-Thie) | — | 1 | —C$_2$(Me)$_4$— |
| 621 | Zr | Cl | 2-(2-Py) | 4-Ph | 2 | 2-(2-Py) | 4-Ph | 2 | —C$_2$(Me)$_4$— |
| 622 | Zr | Cl | 2-(2-Py) | — | 1 | 2-(2-Py) | — | 1 | —C$_2$(Me)$_4$— |
| 623 | Zr | Cl | 2-(2-BzFu) | 4-Ph | 2 | 2-(2-BzFu) | 4-Ph | 2 | —C$_2$(Me)$_4$— |
| 624 | Zr | Cl | 2-(2-BzFu) | — | 1 | 2-(2-BzFu) | — | 1 | —C$_2$(Me)$_4$— |
| 625 | Zr | Cl | 2-[2-(N—Me—Pyr)] | 4-Ph | 2 | 2-[2-(N—Me—Pyr)] | 4-Ph | 2 | —C$_2$(Me)$_4$— |
| 626 | Zr | Cl | 2-[2-(N—Me—Pyr)] | — | 1 | 2-[2-(N—Me—Pyr)] | — | 1 | —C$_2$(Me)$_4$— |

TABLE 16

|  |  |  | CA¹: Tetrahydroindenyl | | | CA²: Tetrahydroindenyl | | | |
| --- | --- | --- | --- | --- | --- | --- | --- | --- | --- |
| No. | M | X | Ra | R¹ | p + m | Ra | R¹ | q + n | Y |
| 627 | Zr | Cl | 2-(2-Fu) | — | 1 | 2-(2-Fu) | — | 1 | —SiH$_2$— |
| 628 | Zr | Cl | 2-(2-Fu) | — | 1 | 2-(2-Fu) | — | 1 | —Si(Me)$_2$— |
| 629 | Zr | Cl | 2-(2-Fu) | 7-Me | 2 | 2-(2-Fu) | 7-Me | 2 | —Si(Me)$_2$— |
| 630 | Zr | Cl | 2-(2-Fu) | 4-Me | 2 | 2-(2-Fu) | 4-Me | 2 | —Si(Me)$_2$— |
| 631 | Zr | Cl | 2-(2-Fu) | 3-Me | 2 | 2-(2-Fu) | 3-Me | 2 | —Si(Me)$_2$— |
| 632 | Zr | Cl | 2-(2-Fu) | 3-Me, 7-Me | 3 | 2-(2-Fu) | 3-Me, 7-Me | 3 | —Si(Me)$_2$— |
| 633 | Zr | Cl | 2-(2-Fu) | 4-Me, 7-Me | 3 | 2-(2-Fu) | 4-Me, 7-Me | 3 | —Si(Me)$_2$— |
| 634 | Zr | Cl | 2-(2-Fu) | 4-Cl | 2 | 2-(2-Fu) | 4-Cl | 2 | —Si(Me)$_2$— |
| 635 | Zr | Cl | 2-(2-Fu) | 4-Et | 2 | 2-(2-Fu) | 4-Et | 2 | —Si(Me)$_2$— |
| 636 | Zr | Cl | 2-(2-Fu) | 4-I—Pr | 2 | 2-(2-Fu) | 4-I—Pr | 2 | —Si(Me)$_2$— |
| 637 | Zr | Cl | 2-(2-Fu) | 4-t-Bu | 2 | 2-(2-Fu) | 4-t-Bu | 2 | —Si(Me)$_2$— |
| 638 | Zr | Cl | 2-(2-Fu) | 4-Ph | 2 | 2-(2-Fu) | 4-Ph | 2 | —Si(Me)$_2$— |
| 639 | Zr | Cl | 2-(2-Fu) | 4-Np | 2 | 2-(2-Fu) | 4-Np | 2 | —Si(Me)$_2$— |
| 640 | Zr | Cl | 2-(2-Fu) | 4-OMe | 2 | 2-(2-Fu) | 4-OMe | 2 | —Si(Me)$_2$— |
| 641 | Zr | Cl | 2-(2-Fu) | 4-OPh | 2 | 2-(2-Fu) | 4-OPh | 2 | —Si(Me)$_2$— |
| 642 | Zr | Cl | 2-(2-Fu) | 4-Bzl | 2 | 2-(2-Fu) | 4-Bzl | 2 | —Si(Me)$_2$— |
| 643 | Zr | Cl | 2-(2-Fu) | 4-Tol | 2 | 2-(2-Fu) | 4-Tol | 2 | —Si(Me)$_2$— |
| 644 | Zr | Cl | 2-(2-Fu) | 4-OBzl | 2 | 2-(2-Fu) | 4-OBzl | 2 | —Si(Me)$_2$— |
| 645 | Zr | Cl | 2-(2-Fu) | 4-TMS | 2 | 2-(2-Fu) | 4-TMS | 2 | —Si(Me)$_2$— |
| 646 | Zr | Cl | 2-(2-Fu) | 4-(1-Pyr) | 2 | 2-(2-Fu) | 4-(1-Pyr) | 2 | —Si(Me)$_2$— |
| 647 | Zr | Cl | 2-(2-Fu) | 4-(1-Indo) | 2 | 2-(2-Fu) | 4-(1-Indo) | 2 | —Si(Me)$_2$— |
| 648 | Zr | Cl | 2-(2-Fu), 4-(2-Fu) | — | 2 | 2-(2-Fu), 4-(2-Fu) | — | 2 | —Si(Me)$_2$— |
| 649 | Zr | Cl | 2-(2-Fu), 4-(2-Thie) | — | 2 | 2-(2-Fu), 4-(2-Thie) | — | 2 | —Si(Me)$_2$— |
| 650 | Zr | Cl | 2-(2-Fu), 4-(2-BzFu) | — | 2 | 2-(2-Fu), 4-(2-BzFu) | — | 2 | —Si(Me)$_2$— |
| 651 | Zr | Cl | 2-(2-Fu), 4-(2-Py) | — | 2 | 2-(2-Fu), 4-(2-Py) | — | 2 | —Si(Me)$_2$— |
| 652 | Zr | Cl | 2-(2-Fu), 4-(1-MePyr) | — | 2 | 2-(2-Fu), 4-(1-MePyr) | — | 2 | —Si(Me)$_2$— |
| 653 | Zr | Cl | 2-(2-Fu) | 4-Et, 7-Et | 3 | 2-(2-Fu) | 4-Et, 7-Et | 3 | —Si(Me)$_2$— |
| 654 | Zr | Cl | 2-(2-Fu) | 4-I—Pr, 7-I—Pr | 3 | 2-(2-Fu) | 4-I—Pr, 7-I—Pr | 3 | —Si(Me)$_2$— |
| 655 | Zr | Cl | 2-(2-Fu) | 4-t-Bu, 7-t-Bu | 3 | 2-(2-Fu) | 4-t-Bu, 7-t-Bu | 3 | —Si(Me)$_2$— |
| 656 | Zr | Cl | 2-(2-Fu) | 4-Ph, 7-Ph | 3 | 2-(2-Fu) | 4-Ph, 7-Ph | 3 | —Si(Me)$_2$— |
| 657 | Zr | Cl | 2-(2-Fu) | 3-Ph, 7-Me | 3 | 2-(2-Fu) | 3-Ph, 7-Me | 3 | —Si(Me)$_2$— |
| 658 | Zr | Cl | 2-(2-Fu) | 4-Me, 7-Me | 3 | 2-(2-Fu) | 4-Me, 7-Me | 3 | —Si(Et)$_2$— |
| 659 | Zr | Cl | 2-(2-Fu) | 4-Me, 7-Me | 3 | 2-(2-Fu) | 4-Me, 7-Me | 3 | —Si(Ph)$_2$— |
| 660 | Zr | Me | 2-(2-Fu) | 4-Ph | 2 | 2-(2-Fu) | 4-Ph | 2 | —Si(Me)$_2$— |
| 661 | Zr | Bzl | 2-(2-Fu) | 4-Ph | 2 | 2-(2-Fu) | 4-Ph | 2 | —Si(Me)$_2$— |
| 662 | Hf | Cl | 2-(2-Fu) | 4-Ph | 2 | 2-(2-Fu) | 4-Ph | 2 | —Si(Me)$_2$— |
| 663 | Ti | Cl | 2-(2-Fu) | 4-Ph | 2 | 2-(2-Fu) | 4-Ph | 2 | —Si(Me)$_2$— |
| 664 | Hf | Cl | 2-(2-Fu) | 3-Me, 7-Me | 3 | 2-(2-Fu) | 3-Me, 7-Me | 3 | —Si(Me)$_2$— |
| 665 | Ti | Cl | 2-(2-Fu) | 3-Me, 7-Me | 3 | 2-(2-Fu) | 3-Me, 7-Me | 3 | —Si(Me)$_2$— |
| 666 | Zr | Cl | 2-(3-Fu) | 4-Ph | 2 | 2-(3-Fu) | 4-Ph | 2 | —Si(Me)$_2$— |
| 667 | Zr | Cl | 2-(3-Fu) | 4-Ph | 2 | 2-(3-Fu) | 4-Ph | 2 | —Si(Me)$_2$— |
| 668 | Zr | Cl | 2-[2-(3-Me—Fu)] | 4-Ph | 2 | 2-[2-(3-Me—Fu)] | 4-Ph | 2 | —Si(Me)$_2$— |
| 669 | Zr | Cl | 2-[2-(3-Me—Fu)] | — | 1 | 2-[2-(3-Me—Fu)] | — | 1 | —Si(Me)$_2$— |
| 670 | Zr | Cl | 2-(2-Thie) | 4-Ph | 2 | 2-(2-Thie) | 4-Ph | 2 | —Si(Me)$_2$— |
| 671 | Zr | Cl | 2-(2-Thie) | — | 1 | 2-(2-Thie) | — | 1 | —Si(Me)$_2$— |
| 672 | Zr | Cl | 2-(2-Py) | 4-Ph | 2 | 2-(2-Py) | 4-Ph | 2 | —Si(Me)$_2$— |
| 673 | Zr | Cl | 2-(2-Py) | — | 1 | 2-(2-Py) | — | 1 | —Si(Me)$_2$— |
| 674 | Zr | Cl | 2-(2-BzFu) | 4-Ph | 2 | 2-(2-BzFu) | 4-Ph | 2 | —Si(Me)$_2$— |
| 675 | Zr | Cl | 2-(2-BzFu) | — | 1 | 2-(2-BzFu) | — | 1 | —Si(Me)$_2$— |
| 676 | Zr | Cl | 2-[2-(N—Me—Pyr)] | 4-Ph | 2 | 2-[2-(N—Me—Pyr)] | 4-Ph | 2 | —Si(Me)$_2$— |
| 677 | Zr | Cl | 2-[2-(N—Me—Pyr)] | — | 1 | 2-[2-(N—Me—Pyr)] | — | 1 | —Si(Me)$_2$— |

TABLE 17

|  |  |  | CA¹: Tetrahydroindenyl | | | CA²: Tetrahydroindenyl | | | |
| --- | --- | --- | --- | --- | --- | --- | --- | --- | --- |
| No. | M | X | Ra | R¹ | p + m | Ra | R¹ | q + n | Y |
| 678 | Zr | Cl | 2-(2-Fu) | — | 1 | 2-(2-Fu) | — | 1 | —GeH$_2$— |
| 679 | Zr | Cl | 2-(2-Fu) | — | 1 | 2-(2-Fu) | — | 1 | —Ge(Me)$_2$— |
| 680 | Zr | Cl | 2-(2-Fu) | 7-Me | 2 | 2-(2-Fu) | 7-Me | 2 | —Ge(Me)$_2$— |
| 681 | Zr | Cl | 2-(2-Fu) | 4-Me | 2 | 2-(2-Fu) | 4-Me | 2 | —Ge(Me)$_2$— |
| 682 | Zr | Cl | 2-(2-Fu) | 3-Me | 2 | 2-(2-Fu) | 3-Me | 2 | —Ge(Me)$_2$— |
| 683 | Zr | Cl | 2-(2-Fu) | 3-Me, 7-Me | 3 | 2-(2-Fu) | 3-Me, 7-Me | 3 | —Ge(Me)$_2$— |
| 684 | Zr | Cl | 2-(2-Fu) | 4-Me, 7-Me | 3 | 2-(2-Fu) | 4-Me, 7-Me | 3 | —Ge(Me)$_2$— |
| 685 | Zr | Cl | 2-(2-Fu) | 4-Cl | 2 | 2-(2-Fu) | 4-Cl | 2 | —Ge(Me)$_2$— |
| 686 | Zr | Cl | 2-(2-Fu) | 4-Et | 2 | 2-(2-Fu) | 4-Et | 2 | —Ge(Me)$_2$— |
| 687 | Zr | Cl | 2-(2-Fu) | 4-I—Pr | 2 | 2-(2-Fu) | 4-I—Pr | 2 | —Ge(Me)$_2$— |
| 688 | Zr | Cl | 2-(2-Fu) | 4-t-Bu | 2 | 2-(2-Fu) | 4-t-Bu | 2 | —Ge(Me)$_2$— |
| 689 | Zr | Cl | 2-(2-Fu) | 4-Ph | 2 | 2-(2-Fu) | 4-Ph | 2 | —Ge(Me)$_2$— |
| 690 | Zr | Cl | 2-(2-Fu) | 4-Np | 2 | 2-(2-Fu) | 4-Np | 2 | —Ge(Me)$_2$— |
| 691 | Zr | Cl | 2-(2-Fu) | 4-OMe | 2 | 2-(2-Fu) | 4-OMe | 2 | —Ge(Me)$_2$— |

TABLE 17-continued

| | | | CA¹: Tetrahydroindenyl | | | CA²: Tetrahydroindenyl | | | |
|---|---|---|---|---|---|---|---|---|---|
| No. | M | X | Ra | R¹ | p + m | Ra | R¹ | q + n | Y |
| 692 | Zr | Cl | 2-(2-Fu) | 4-OPh | 2 | 2-(2-Fu) | 4-OPh | 2 | —Ge(Me)$_2$— |
| 693 | Zr | Cl | 2-(2-Fu) | 4-Bzl | 2 | 2-(2-Fu) | 4-Bzl | 2 | —Ge(Me)$_2$— |
| 694 | Zr | Cl | 2-(2-Fu) | 4-Tol | 2 | 2-(2-Fu) | 4-Tol | 2 | —Ge(Me)$_2$— |
| 695 | Zr | Cl | 2-(2-Fu) | 4-OBzl | 2 | 2-(2-Fu) | 4-OBzl | 2 | —Ge(Me)$_2$— |
| 696 | Zr | Cl | 2-(2-Fu) | 4-TMS | 2 | 2-(2-Fu) | 4-TMS | 2 | —Ge(Me)$_2$— |
| 697 | Zr | Cl | 2-(2-Fu) | 4-(1-Pyr) | 2 | 2-(2-Fu) | 4-(1-Pyr) | 2 | —Ge(Me)$_2$— |
| 698 | Zr | Cl | 2-(2-Fu) | 4-(1-Indo) | 2 | 2-(2-Fu) | 4-(1-Indo) | 2 | —Ge(Me)$_2$— |
| 699 | Zr | Cl | 2-(2-Fu), 4-(2-Fu) | — | 2 | 2-(2-Fu), 4-(2-Fu) | — | 2 | —Ge(Me)$_2$— |
| 700 | Zr | Cl | 2-(2-Fu), 4-(2-Thie) | — | 2 | 2-(2-Fu), 4-(2-Thie) | — | 2 | —Ge(Me)$_2$— |
| 701 | Zr | Cl | 2-(2-Fu), 4-(2-BzFu) | — | 2 | 2-(2-Fu), 4-(2-BzFu) | — | 2 | —Ge(Me)$_2$— |
| 702 | Zr | Cl | 2-(2-Fu), 4-(2-Py) | — | 2 | 2-(2-Fu), 4-(2-Py) | — | 2 | —Ge(Me)$_2$— |
| 703 | Zr | Cl | 2-(2-Fu), 4-(1-MePyr) | — | 2 | 2-(2-Fu), 4-(1-MePyr) | — | 2 | —Ge(Me)$_2$— |
| 704 | Zr | Cl | 2-(2-Fu) | 4-Et, 7-Et | 3 | 2-(2-Fu) | 4-Et, 7-Et | 3 | —Ge(Me)$_2$— |
| 705 | Zr | Cl | 2-(2-Fu) | 4-I—Pr, 7-I—Pr | 3 | 2-(2-Fu) | 4-I—Pr, 7-I—Pr | 3 | —Ge(Me)$_2$— |
| 706 | Zr | Cl | 2-(2-Fu) | 4-t-Bu, 7-t-Bu | 3 | 2-(2-Fu) | 4-t-Bu, 7-t-Bu | 3 | —Ge(Me)$_2$— |
| 707 | Zr | Cl | 2-(2-Fu) | 4-Ph, 7-Ph | 3 | 2-(2-Fu) | 4-Ph, 7-Ph | 3 | —Ge(Me)$_2$— |
| 708 | Zr | Cl | 2-(2-Fu) | 3-Ph, 7-Me | 3 | 2-(2-Fu) | 3-Ph, 7-Me | 3 | —Ge(Me)$_2$— |
| 709 | Zr | Cl | 2-(2-Fu) | 4-Me, 7-Me | 3 | 2-(2-Fu) | 4-Me, 7-Me | 3 | —Ge(Et)$_2$— |
| 710 | Zr | Cl | 2-(2-Fu) | 4-Me, 7-Me | 3 | 2-(2-Fu) | 4-Me, 7-Me | 3 | —Ge(Ph)$_2$— |
| 711 | Zr | Me | 2-(2-Fu) | 4-Ph | 2 | 2-(2-Fu) | 4-Ph | 2 | —Ge(Me)$_2$— |
| 712 | Zr | Bzl | 2-(2-Fu) | 4-Ph | 2 | 2-(2-Fu) | 4-Ph | 2 | —Ge(Me)$_2$— |
| 713 | Hf | Cl | 2-(2-Fu) | 4-Ph | 2 | 2-(2-Fu) | 4-Ph | 2 | —Ge(Me)$_2$— |
| 714 | Ti | Cl | 2-(2-Fu) | 4-Ph | 2 | 2-(2-Fu) | 4-Ph | 2 | —Ge(Me)$_2$— |
| 715 | Hf | Cl | 2-(2-Fu) | 3-Me, 7-Me | 3 | 2-(2-Fu) | 3-Me, 7-Me | 3 | —Ge(Me)$_2$— |
| 716 | Ti | Cl | 2-(2-Fu) | 3-Me, 7-Me | 3 | 2-(2-Fu) | 3-Me, 7-Me | 3 | —Ge(Me)$_2$— |
| 717 | Zr | Cl | 2-(3-Fu) | 4-Ph | 2 | 2-(3-Fu) | 4-Ph | 2 | —Ge(Me)$_2$— |
| 718 | Zr | Cl | 2-(3-Fu) | 4-Ph | 2 | 2-(3-Fu) | 4-Ph | 2 | —Ge(Me)$_2$— |
| 719 | Zr | Cl | 2-[2-(3-Me—Fu)] | 4-Ph | 2 | 2-[2-(3-Me—Fu)] | 4-Ph | 2 | —Ge(Me)$_2$— |
| 720 | Zr | Cl | 2-[2-(3-Me—Fu)] | — | 1 | 2-[2-(3-Me—Fu)] | — | 1 | —Ge(Me)$_2$— |
| 721 | Zr | Cl | 2-(2-Thie) | 4-Ph | 2 | 2-(2-Thie) | 4-Ph | 2 | —Ge(Me)$_2$— |
| 722 | Zr | Cl | 2-(2-Thie) | — | 1 | 2-(2-Thie) | — | 1 | —Ge(Me)$_2$— |
| 723 | Zr | Cl | 2-(2-Py) | 4-Ph | 2 | 2-(2-Py) | 4-Ph | 2 | —Ge(Me)$_2$— |
| 724 | Zr | Cl | 2-(2-Py) | — | 1 | 2-(2-Py) | — | 1 | —Ge(Me)$_2$— |
| 725 | Zr | Cl | 2-(2-BzFu) | 4-Ph | 2 | 2-(2-BzFu) | 4-Ph | 2 | —Ge(Me)$_2$— |
| 726 | Zr | Cl | 2-(2-BzFu) | — | 1 | 2-(2-BzFu) | — | 1 | —Ge(Me)$_2$— |
| 727 | Zr | Cl | 2-[2-(N—Me—Pyr)] | 4-Ph | 2 | 2-[2-(N—Me—Pyr)] | 4-Ph | 2 | —Ge(Me)$_2$— |
| 728 | Zr | Cl | 2-[2-(N—Me—Pyr)] | — | 1 | 2-[2-(N—Me—Pyr)] | — | 1 | —Ge(Me)$_2$— |

TABLE 18

| | | | CA¹: Benzoindenyl | | | CA²: Benzoindenyl | | | |
|---|---|---|---|---|---|---|---|---|---|
| No. | M | X | Ra | R¹ | p + m | Ra | R¹ | q + n | Y |
| 729 | Zr | Cl | 2-(2-Fu) | — | 1 | 2-(2-Fu) | — | 1 | —SiH$_2$— |
| 730 | Zr | Cl | 2-(2-Fu) | — | 1 | 2-(2-Fu) | — | 1 | —Si(Me)$_2$— |
| 731 | Zr | Cl | 2-(2-Fu) | 9-Me | 2 | 2-(2-Fu) | 9-Me | 2 | —Si(Me)$_2$— |
| 732 | Zr | Cl | 2-(2-Fu) | 5-Me | 2 | 2-(2-Fu) | 5-Me | 2 | —Si(Me)$_2$— |
| 733 | Zr | Cl | 2-(2-Fu) | 3-Me | 2 | 2-(2-Fu) | 3-Me | 2 | —Si(Me)$_2$— |
| 734 | Zr | Cl | 2-(2-Fu) | 3-Me, 9-Me | 3 | 2-(2-Fu) | 3-Me, 9-Me | 3 | —Si(Me)$_2$— |
| 735 | Zr | Cl | 2-(2-Fu) | 5-Me, 9-Me | 3 | 2-(2-Fu) | 5-Me, 9-Me | 3 | —Si(Me)$_2$— |
| 736 | Zr | Cl | 2-(2-Fu) | 5-Cl | 2 | 2-(2-Fu) | 5-Cl | 2 | —Si(Me)$_2$— |
| 737 | Zr | Cl | 2-(2-Fu) | 5-Et | 2 | 2-(2-Fu) | 5-Et | 2 | —Si(Me)$_2$— |
| 738 | Zr | Cl | 2-(2-Fu) | 5-i-Pr | 2 | 2-(2-Fu) | 5-i-Pr | 2 | —Si(Me)$_2$— |
| 739 | Zr | Cl | 2-(2-Fu) | 5-t-Bu | 2 | 2-(2-Fu) | 5-t-Bu | 2 | —Si(Me)$_2$— |
| 740 | Zr | Cl | 2-(2-Fu) | 5-Ph | 2 | 2-(2-Fu) | 5-Ph | 2 | —Si(Me)$_2$— |
| 741 | Zr | Cl | 2-(2-Fu) | 5-Np | 2 | 2-(2-Fu) | 5-Np | 2 | —Si(Me)$_2$— |
| 742 | Zr | Cl | 2-(2-Fu) | 5-OMe | 2 | 2-(2-Fu) | 5-OMe | 2 | —Si(Me)$_2$— |
| 743 | Zr | Cl | 2-(2-Fu) | 5-OPh | 2 | 2-(2-Fu) | 5-OPh | 2 | —Si(Me)$_2$— |
| 744 | Zr | Cl | 2-(2-Fu) | 5-Bzl | 2 | 2-(2-Fu) | 5-Bzl | 2 | —Si(Me)$_2$— |
| 745 | Zr | Cl | 2-(2-Fu) | 5-Tol | 2 | 2-(2-Fu) | 5-Tol | 2 | —Si(Me)$_2$— |
| 746 | Zr | Cl | 2-(2-Fu) | 5-OBzl | 2 | 2-(2-Fu) | 5-OBzl | 2 | —Si(Me)$_2$— |
| 747 | Zr | Cl | 2-(2-Fu) | 5-TMS | 2 | 2-(2-Fu) | 5-TMS | 2 | —Si(Me)$_2$— |
| 748 | Zr | Cl | 2-(2-Fu) | 5-(1-Pyr) | 2 | 2-(2-Fu) | 5-(1-Pyr) | 2 | —Si(Me)$_2$— |
| 749 | Zr | Cl | 2-(2-Fu) | 5-(1-Indo) | 2 | 2-(2-Fu) | 5-(1-Indo) | 2 | —Si(Me)$_2$— |
| 750 | Zr | Cl | 2-(2-Fu), 5-(2-Fu) | — | 2 | 2-(2-Fu), 5-(2-Fu) | — | 2 | —Si(Me)$_2$— |
| 751 | Zr | Cl | 2-(2-Fu), 5-(2-Thie) | — | 2 | 2-(2-Fu), 5-(2-Thie) | — | 2 | —Si(Me)$_2$— |
| 752 | Zr | Cl | 2-(2-Fu), 5-(2-BzFu) | — | 2 | 2-(2-Fu), 5-(2-BzFu) | — | 2 | —Si(Me)$_2$— |
| 753 | Zr | Cl | 2-(2-Fu), 5-(2-Py) | — | 2 | 2-(2-Fu), 5-(2-Py) | — | 2 | —Si(Me)$_2$— |
| 754 | Zr | Cl | 2-(2-Fu), 5-[2-(1-MePyr)] | — | 2 | 2-(2-Fu), 5-[2-(1-MePyr)] | — | 2 | —Si(Me)$_2$— |
| 755 | Zr | Cl | 2-(2-Fu) | 5-Et, 9-Et | 3 | 2-(2-Fu) | 5-Et, 9-Et | 3 | —Si(Me)$_2$— |
| 756 | Zr | Cl | 2-(2-Fu) | 5-i-Pr, 9-i-Pr | 3 | 2-(2-Fu) | 5-i-Pr, 9-i-Pr | 3 | —Si(Me)$_2$— |

TABLE 18-continued

| No. | M | X | Ra | R¹ | p + m | Ra | R¹ | q + n | Y |
|---|---|---|---|---|---|---|---|---|---|
| 757 | Zr | Cl | 2-(2-Fu) | 5-t-Bu, 9-t-Bu | 3 | 2-(2-Fu) | 5-t-Bu, 9-t-Bu | 3 | —Si(Me)$_2$— |
| 758 | Zr | Cl | 2-(2-Fu) | 5-Ph, 9-Ph | 3 | 2-(2-Fu) | 5-Ph, 9-Ph | 3 | —Si(Me)$_2$— |
| 759 | Zr | Cl | 2-(2-Fu) | 3-Ph, 9-Me | 3 | 2-(2-Fu) | 3-Ph, 9-Me | 3 | —Si(Me)$_2$— |
| 760 | Zr | Cl | 2-(2-Fu) | 5-Me, 9-Me | 3 | 2-(2-Fu) | 5-Me, 9-Me | 3 | —Si(Et)$_2$— |
| 761 | Zr | Cl | 2-(2-Fu) | 5-Me, 9-Me | 3 | 2-(2-Fu) | 5-Me, 9-Me | 3 | —Si(Ph)$_2$— |
| 762 | Zr | Me | 2-(2-Fu) | 5-Ph | 2 | 2-(2-Fu) | 5-Ph | 2 | —Si(Me)$_2$— |
| 763 | Zr | Bzl | 2-(2-Fu) | 5-Ph | 2 | 2-(2-Fu) | 5-Ph | 2 | —Si(Me)$_2$— |
| 764 | Hf | Cl | 2-(2-Fu) | 5-Ph | 2 | 2-(2-Fu) | 5-Ph | 2 | —Si(Me)$_2$— |
| 765 | Ti | Cl | 2-(2-Fu) | 5-Ph | 2 | 2-(2-Fu) | 5-Ph | 2 | —Si(Me)$_2$— |
| 766 | Hf | Cl | 2-(2-Fu) | 3-Me, 9-Me | 3 | 2-(2-Fu) | 3-Me, 9-Me | 3 | —Si(Me)$_2$— |
| 767 | Ti | Cl | 2-(2-Fu) | 3-Me, 9-Me | 3 | 2-(2-Fu) | 3-Me, 9-Me | 3 | —Si(Me)$_2$— |
| 768 | Zr | Cl | 2-(3-Fu) | 5-Ph | 2 | 2-(3-Fu) | 5-Ph | 2 | —Si(Me)$_2$— |
| 769 | Zr | Cl | 2-(3-Fu) | 5-Ph | 2 | 2-(3-Fu) | 5-Ph | 2 | —Si(Me)$_2$— |
| 770 | Zr | Cl | 2-[2-(3-Me—Fu)] | 5-Ph | 2 | 2-[2-(3-Me—Fu)] | 5-Ph | 2 | —Si(Me)$_2$— |
| 771 | Zr | Cl | 2-[2-(3-Me—Fu)] | — | 1 | 2-[2-(3-Me—Fu)] | — | 1 | —Si(Me)$_2$— |
| 772 | Zr | Cl | 2-(2-Thie) | 5-Ph | 2 | 2-(2-Thie) | 5-Ph | 2 | —Si(Me)$_2$— |
| 773 | Zr | Cl | 2-(2-Thie) | — | 1 | 2-(2-Thie) | — | 1 | —Si(Me)$_2$— |
| 774 | Zr | Cl | 2-(2-Py) | 5-Ph | 2 | 2-(2-Py) | 5-Ph | 2 | —Si(Me)$_2$— |
| 775 | Zr | Cl | 2-(2-Py) | — | 1 | 2-(2-Py) | — | 1 | —Si(Me)$_2$— |
| 776 | Zr | Cl | 2-(2-BzFu) | 5-Ph | 2 | 2-(2-BzFu) | 5-Ph | 2 | —Si(Me)$_2$— |
| 777 | Zr | Cl | 2-(2-BzFu) | — | 1 | 2-(2-BzFu) | — | 1 | —Si(Me)$_2$— |
| 778 | Zr | Cl | 2-[2-(N—Me—Pyr)] | 5-Ph | 2 | 2-[2-(N—Me—Pyr)] | 5-Ph | 2 | —Si(Me)$_2$— |
| 779 | Zr | Cl | 2-[2-(N—Me—Pyr)] | — | 1 | 2-[2-(N—Me—Pyr)] | — | 1 | —Si(Me)$_2$— |

TABLE 19

| No. | M | X | Ra | R¹ | p + m | Ra | R¹ | q + n | Y |
|---|---|---|---|---|---|---|---|---|---|
| 780 | Zr | Cl | 2-(2-Fu) | — | 1 | 2-(2-Fu) | — | 1 | —GeH$_2$— |
| 781 | Zr | Cl | 2-(2-Fu) | — | 1 | 2-(2-Fu) | — | 1 | —Ge(Me)$_2$— |
| 782 | Zr | Cl | 2-(2-Fu) | 9-Me | 2 | 2-(2-Fu) | 9-Me | 2 | —Ge(Me)$_2$— |
| 783 | Zr | Cl | 2-(2-Fu) | 5-Me | 2 | 2-(2-Fu) | 5-Me | 2 | —Ge(Me)$_2$— |
| 784 | Zr | Cl | 2-(2-Fu) | 3-Me | 2 | 2-(2-Fu) | 3-Me | 2 | —Ge(Me)$_2$— |
| 785 | Zr | Cl | 2-(2-Fu) | 3-Me, 9-Me | 3 | 2-(2-Fu) | 3-Me, 9-Me | 3 | —Ge(Me)$_2$— |
| 786 | Zr | Cl | 2-(2-Fu) | 5-Me, 9-Me | 3 | 2-(2-Fu) | 5-Me, 9-Me | 3 | —Ge(Me)$_2$— |
| 787 | Zr | Cl | 2-(2-Fu) | 5-Cl | 2 | 2-(2-Fu) | 5-Cl | 2 | —Ge(Me)$_2$— |
| 788 | Zr | Cl | 2-(2-Fu) | 5-Et | 2 | 2-(2-Fu) | 5-Et | 2 | —Ge(Me)$_2$— |
| 789 | Zr | Cl | 2-(2-Fu) | 5-i-Pr | 2 | 2-(2-Fu) | 5-i-Pr | 2 | —Ge(Me)$_2$— |
| 790 | Zr | Cl | 2-(2-Fu) | 5-t-Bu | 2 | 2-(2-Fu) | 5-t-Bu | 2 | —Ge(Me)$_2$— |
| 791 | Zr | Cl | 2-(2-Fu) | 5-Ph | 2 | 2-(2-Fu) | 5-Ph | 2 | —Ge(Me)$_2$— |
| 792 | Zr | Cl | 2-(2-Fu) | 5-Np | 2 | 2-(2-Fu) | 5-Np | 2 | —Ge(Me)$_2$— |
| 793 | Zr | Cl | 2-(2-Fu) | 5-OMe | 2 | 2-(2-Fu) | 5-OMe | 2 | —Ge(Me)$_2$— |
| 794 | Zr | Cl | 2-(2-Fu) | 5-OPh | 2 | 2-(2-Fu) | 5-OPh | 2 | —Ge(Me)$_2$— |
| 795 | Zr | Cl | 2-(2-Fu) | 5-Bzl | 2 | 2-(2-Fu) | 5-Bzl | 2 | —Ge(Me)$_2$— |
| 796 | Zr | Cl | 2-(2-Fu) | 5-Tol | 2 | 2-(2-Fu) | 5-Tol | 2 | —Ge(Me)$_2$— |
| 797 | Zr | Cl | 2-(2-Fu) | 5-OBzl | 2 | 2-(2-Fu) | 5-OBzl | 2 | —Ge(Me)$_2$— |
| 798 | Zr | Cl | 2-(2-Fu) | 5-TMS | 2 | 2-(2-Fu) | 5-TMS | 2 | —Ge(Me)$_2$— |
| 799 | Zr | Cl | 2-(2-Fu) | 5-(1-Pyr) | 2 | 2-(2-Fu) | 5-(1-Pyr) | 2 | —Ge(Me)$_2$— |
| 800 | Zr | Cl | 2-(2-Fu) | 5-(1-Indo) | 2 | 2-(2-Fu) | 5-(1-Indo) | 2 | —Ge(Me)$_2$— |
| 801 | Zr | Cl | 2-(2-Fu), 5-(2-Fu) | — | 2 | 2-(2-Fu), 5-(2-Fu) | — | 2 | —Ge(Me)$_2$— |
| 802 | Zr | Cl | 2-(2-Fu), 5-(2-Thie) | — | 2 | 2-(2-Fu), 5-(2-Thie) | — | 2 | —Ge(Me)$_2$— |
| 803 | Zr | Cl | 2-(2-Fu), 5-(2-BzFu) | — | 2 | 2-(2-Fu), 5-(2-BzFu) | — | 2 | —Ge(Me)$_2$— |
| 804 | Zr | Cl | 2-(2-Fu), 5-(2-Py) | — | 2 | 2-(2-Fu), 5-(2-Py) | — | 2 | —Ge(Me)$_2$— |
| 805 | Zr | Cl | 2-(2-Fu), 5-[2-(1-MePyr)] | — | 2 | 2-(2-Fu), 5-[2-(1-MePyr)] | — | 2 | —Ge(Me)$_2$— |
| 806 | Zr | Cl | 2-(2-Fu) | 5-Et, 9-Et | 3 | 2-(2-Fu) | 5-Et, 9-Et | 3 | —Ge(Me)$_2$— |
| 807 | Zr | Cl | 2-(2-Fu) | 5-i-Pr, 9-i-Pr | 3 | 2-(2-Fu) | 5-i-Pr, 9-i-Pr | 3 | —Ge(Me)$_2$— |
| 808 | Zr | Cl | 2-(2-Fu) | 5-t-Bu, 9-t-Bu | 3 | 2-(2-Fu) | 5-t-Bu, 9-t-Bu | 3 | —Ge(Me)$_2$— |
| 809 | Zr | Cl | 2-(2-Fu) | 5-Ph, 9-Ph | 3 | 2-(2-Fu) | 5-Ph, 9-Ph | 3 | —Ge(Me)$_2$— |
| 810 | Zr | Cl | 2-(2-Fu) | 3-Ph, 9-Me | 3 | 2-(2-Fu) | 3-Ph, 9-Me | 3 | —Ge(Me)$_2$— |
| 811 | Zr | Cl | 2-(2-Fu) | 5-Me, 9-Me | 3 | 2-(2-Fu) | 5-Me, 9-Me | 3 | —Ge(Et)$_2$— |
| 812 | Zr | Cl | 2-(2-Fu) | 5-Me, 9-Me | 3 | 2-(2-Fu) | 5-Me, 9-Me | 3 | —Ge(Ph)$_2$— |
| 813 | Zr | Me | 2-(2-Fu) | 5-Ph | 2 | 2-(2-Fu) | 5-Ph | 2 | —Ge(Me)$_2$— |
| 814 | Zr | Bzl | 2-(2-Fu) | 5-Ph | 2 | 2-(2-Fu) | 5-Ph | 2 | —Ge(Me)$_2$— |
| 815 | Hf | Cl | 2-(2-Fu) | 5-Ph | 2 | 2-(2-Fu) | 5-Ph | 2 | —Ge(Me)$_2$— |
| 816 | Ti | Cl | 2-(2-Fu) | 5-Ph | 2 | 2-(2-Fu) | 5-Ph | 2 | —Ge(Me)$_2$— |
| 817 | Hf | Cl | 2-(2-Fu) | 3-Me, 9-Me | 3 | 2-(2-Fu) | 3-Me, 9-Me | 3 | —Ge(Me)$_2$— |
| 818 | Ti | Cl | 2-(2-Fu) | 3-Me, 9-Me | 3 | 2-(2-Fu) | 3-Me, 9-Me | 3 | —Ge(Me)$_2$— |
| 819 | Zr | Cl | 2-(3-Fu) | 5-Ph | 2 | 2-(3-Fu) | 5-Ph | 2 | —Ge(Me)$_2$— |
| 820 | Zr | Cl | 2-(3-Fu) | 5-Ph | 2 | 2-(3-Fu) | 5-Ph | 2 | —Ge(Me)$_2$— |
| 821 | Zr | Cl | 2-[2-(3-Me—Fu)] | 5-Ph | 2 | 2-[2-(3-Me—Fu)] | 5-Ph | 2 | —Ge(Me)$_2$— |

TABLE 19-continued

| | | | CA¹: Benzoindenyl | | | CA²: Benzoindenyl | | | |
|---|---|---|---|---|---|---|---|---|---|
| No. | M | X | Ra | R¹ | p + m | Ra | R¹ | q + n | Y |
| 822 | Zr | Cl | 2-[2-(3-Me—Fu)] | — | 1 | 2-[2-(3-Me—Fu)] | — | 1 | —Ge(Me)₂— |
| 823 | Zr | Cl | 2-(2-Thie) | 5-Ph | 2 | 2-(2-Thie) | 5-Ph | 2 | —Ge(Me)₂— |
| 824 | Zr | Cl | 2-(2-Thie) | — | 1 | 2-(2-Thie) | — | 1 | —Ge(Me)₂— |
| 825 | Zr | Cl | 2-(2-Py) | 5-Ph | 2 | 2-(2-Py) | 5-Ph | 2 | —Ge(Me)₂— |
| 826 | Zr | Cl | 2-(2-Py) | — | 1 | 2-(2-Py) | — | 1 | —Ge(Me)₂— |
| 827 | Zr | Cl | 2-(2-BzFu) | 5-Ph | 2 | 2-(2-BzFu) | 5-Ph | 2 | —Ge(Me)₂— |
| 828 | Zr | Cl | 2-(2-BzFu) | — | 1 | 2-(2-BzFu) | — | 1 | —Ge(Me)₂— |
| 829 | Zr | Cl | 2-[2-(N—Me—Pyr)] | 5-Ph | 2 | 2-[2-(N—Me—Pyr)] | 5-Ph | 2 | —Ge(Me)₂— |
| 830 | Zr | Cl | 2-[2-(N—Me—Pyr)] | — | 1 | 2-[2-(N—Me—Pyr)] | — | 1 | —Ge(Me)₂— |

TABLE 20

| | | | CA¹: Cyclopentadienyl | | | Z: —(R¹)N— | |
|---|---|---|---|---|---|---|---|
| No. | M | X | Ra | R¹ | p + m | R¹ | Y |
| 831 | Ti | Cl | 2-(2-Fu) | — | 1 | t-Bu | —SiH₂— |
| 832 | Ti | Cl | 2-(2-Fu) | — | 1 | t-Bu | —Si(Me)₂— |
| 833 | Ti | Cl | 2-(2-Fu) | 5-Me | 2 | t-Bu | —Si(Me)₂— |
| 834 | Ti | Cl | 2-(2-Fu) | 4-Me | 2 | t-Bu | —Si(Me)₂— |
| 835 | Ti | Cl | 2-(2-Fu) | 4-OMe | 2 | t-Bu | —Si(Me)₂— |
| 836 | Ti | Cl | 2-(2-Fu) | 4-OPh | 2 | t-Bu | —Si(Me)₂— |
| 837 | Ti | Cl | 2-(2-Fu) | 4-Bzl | 2 | t-Bu | —Si(Me)₂— |
| 838 | Ti | Cl | 2-(2-Fu) | 4-Tol | 2 | t-Bu | —Si(Me)₂— |
| 839 | Ti | Cl | 2-(2-Fu) | 4-OBzl | 2 | t-Bu | —Si(Me)₂— |
| 840 | Ti | Cl | 2-(2-Fu) | 4-TMS | 2 | t-Bu | —Si(Me)₂— |
| 841 | Ti | Cl | 2-(2-Fu) | 4-(1-Pyr) | 2 | t-Bu | —Si(Me)₂— |
| 842 | Ti | Cl | 2-(2-Fu) | 4-(1-Indo) | 2 | t-Bu | —Si(Me)₂— |
| 843 | Ti | Cl | 2-(2-Fu) | 3-Me | 2 | t-Bu | —Si(Me)₂— |
| 844 | Ti | Cl | 2-(2-Fu) | 3-Me, 5-Me | 3 | t-Bu | —Si(Me)₂— |
| 845 | Ti | Cl | 2-(2-Fu) | 4-Me, 5-Me | 3 | t-Bu | —Si(Me)₂— |
| 846 | Ti | Cl | 2-(2-Fu) | 4-Et, 5-Me | 3 | t-Bu | —Si(Me)₂— |
| 847 | Ti | Cl | 2-(2-Fu) | 4-(i-Pr), 5-Me | 3 | t-Bu | —Si(Me)₂— |
| 848 | Ti | Cl | 2-(2-Fu) | 4-(t-Bu), 5-Me | 3 | t-Bu | —Si(Me)₂— |
| 849 | Ti | Cl | 2-(2-Fu) | 4-Ph, 5-Me | 3 | t-Bu | —Si(Me)₂— |
| 850 | Ti | Cl | 2-(2-Fu) | 3-Ph, 5-Me | 3 | t-Bu | —Si(Me)₂— |
| 851 | Ti | Cl | 2-(2-Fu) | 4-Me, 5-Me | 3 | Ph | —Si(Me)₂— |
| 852 | Ti | Cl | 2-(2-Fu) | 4-Me, 5-Me | 3 | Me | —Si(Et)₂— |
| 853 | Ti | Cl | 2-(2-Fu) | 4-Me, 5-Me | 3 | Me | —Si(Ph)₂— |
| 854 | Ti | Me | 2-(2-Fu) | 4-Me, 5-Me | 3 | Me | —Si(Me)₂— |
| 855 | Ti | Bzl | 2-(2-Fu) | 4-Me, 5-Me | 3 | Me | —Si(Me)₂— |
| 856 | Hf | Cl | 2-(2-Fu) | 4-Me, 5-Me | 3 | Me | —Si(Me)₂— |
| 857 | Zr | Cl | 2-(2-Fu) | 4-Me, 5-Me | 3 | Me | —Si(Me)₂— |
| 858 | Hf | Cl | 2-(2-Fu) | 3-Me, 5-Me | 3 | Me | —Si(Me)₂— |
| 859 | Zr | Cl | 2-(2-Fu) | 3-Me, 5-Me | 3 | Me | —Si(Me)₂— |
| 860 | Hf | Cl | 2-(2-Fu) | 4-Me, 5-Me | 3 | t-Bu | —Si(Me)₂— |
| 861 | Zr | Cl | 2-(2-Fu) | 4-Me, 5-Me | 3 | t-Bu | —Si(Me)₂— |
| 862 | Hf | Cl | 2-(2-Fu) | 3-Me, 5-Me | 3 | t-Bu | —Si(Me)₂— |
| 863 | Zr | Cl | 2-(2-Fu) | 3-Me, 5-Me | 3 | t-Bu | —Si(Me)₂— |
| 864 | Ti | Cl | 2-(3-Fu) | 4-Me, 5-Me | 3 | t-Bu | —Si(Me)₂— |
| 865 | Ti | Cl | 2-(3-Fu) | 3-Me, 5-Me | 3 | Me | —Si(Me)₂— |
| 866 | Ti | Cl | 2-[2-(3-Me—Fu)] | 4-Me, 5-Me | 3 | t-Bu | —Si(Me)₂— |
| 867 | Ti | Cl | 2-[2-(3-Me—Fu)] | 3-Me, 5-Me | 3 | Me | —Si(Me)₂— |
| 868 | Ti | Cl | 2-(2-Thie) | 4-Me, 5-Me | 3 | t-Bu | —Si(Me)₂— |
| 869 | Ti | Cl | 2-(2-Thie) | 3-Me, 5-Me | 3 | Me | —Si(Me)₂— |
| 870 | Ti | Cl | 2-(2-Py) | 4-Me, 5-Me | 3 | t-Bu | —Si(Me)₂— |
| 871 | Ti | Cl | 2-(2-Py) | 3-Me, 5-Me | 3 | Me | —Si(Me)₂— |
| 872 | Ti | Cl | 2-(2-BzFu) | 4-Me, 5-Me | 3 | t-Bu | —Si(Me)₂— |
| 873 | Ti | Cl | 2-(2-BzFu) | 3-Me, 5-Me | 3 | Me | —Si(Me)₂— |
| 874 | Ti | Cl | 2-[2-(1-Me—Pyr)] | 4-Me, 5-Me | 3 | t-Bu | —Si(Me)₂— |
| 875 | Ti | Cl | 2-[2-(1-Me—Pyr)] | 3-Me, 5-Me | 3 | Me | —Si(Me)₂— |

TABLE 21

| | | | CA¹: Cyclopentadienyl | | | Z: —(R¹)N— | |
|---|---|---|---|---|---|---|---|
| No. | M | X | Ra | R¹ | p + m | R¹ | Y |
| 876 | Ti | Cl | 2-(2-Fu) | — | 1 | t-Bu | —GeH₂— |
| 877 | Ti | Cl | 2-(2-Fu) | — | 1 | t-Bu | —Ge(Me)₂— |

TABLE 21-continued

| | | | CA¹: Cyclopentadienyl | | | Z: —(R¹)N— | |
|---|---|---|---|---|---|---|---|
| No. | M | X | Ra | R¹ | p + m | R¹ | Y |
| 878 | Ti | Cl | 2-(2-Fu) | 5-Me | 2 | t-Bu | —Ge(Me)₂— |
| 879 | Ti | Cl | 2-(2-Fu) | 4-Me | 2 | t-Bu | —Ge(Me)₂— |
| 880 | Ti | Cl | 2-(2-Fu) | 4-Ome | 2 | t-Bu | —Ge(Me)₂— |
| 881 | Ti | Cl | 2-(2-Fu) | 4-Oph | 2 | t-Bu | —Ge(Me)₂— |
| 882 | Ti | Cl | 2-(2-Fu) | 4-Bzl | 2 | t-Bu | —Ge(Me)₂— |
| 883 | Ti | Cl | 2-(2-Fu) | 4-Tol | 2 | t-Bu | —Ge(Me)₂— |
| 884 | Ti | Cl | 2-(2-Fu) | 4-OBzl | 2 | t-Bu | —Ge(Me)₂— |
| 885 | Ti | Cl | 2-(2-Fu) | 4-TMS | 2 | t-Bu | —Ge(Me)₂— |
| 886 | Ti | Cl | 2-(2-Fu) | 4-(1-Pyr) | 2 | t-Bu | —Ge(Me)₂— |
| 887 | Ti | Cl | 2-(2-Fu) | 4-(1-Indo) | 2 | t-Bu | —Ge(Me)₂— |
| 888 | Ti | Cl | 2-(2-Fu) | 3-Me | 2 | t-Bu | —Ge(Me)₂— |
| 889 | Ti | Cl | 2-(2-Fu) | 3-Me, 5-Me | 3 | t-Bu | —Ge(Me)₂— |
| 890 | Ti | Cl | 2-(2-Fu) | 4-Me, 5-Me | 3 | t-Bu | —Ge(Me)₂— |
| 891 | Ti | Cl | 2-(2-Fu) | 4-Et, 5-Me | 3 | t-Bu | —Ge(Me)₂— |
| 892 | Ti | Cl | 2-(2-Fu) | 4-(i-Pr), 5-Me | 3 | t-Bu | —Ge(Me)₂— |
| 893 | Ti | Cl | 2-(2-Fu) | 4-(t-Bu), 5-Me | 3 | t-Bu | —Ge(Me)₂— |
| 894 | Ti | Cl | 2-(2-Fu) | 4-Ph, 5-Me | 3 | t-Bu | —Ge(Me)₂— |
| 895 | Ti | Cl | 2-(2-Fu) | 3-Ph, 5-Me | 3 | t-Bu | —Ge(Me)₂— |
| 896 | Ti | Cl | 2-(2-Fu) | 4-Me, 5-Me | 3 | Ph | —Ge(Me)₂— |
| 897 | Ti | Cl | 2-(2-Fu) | 4-Me, 5-Me | 3 | Me | —Ge(Et)₂— |
| 898 | Ti | Cl | 2-(2-Fu) | 4-Me, 5-Me | 3 | Me | —Ge(Ph)₂— |
| 899 | Ti | Me | 2-(2-Fu) | 4-Me, 5-Me | 3 | Me | —Ge(Me)₂— |
| 900 | Ti | Bzl | 2-(2-Fu) | 4-Me, 5-Me | 3 | Me | —Ge(Me)₂— |
| 901 | Hf | Cl | 2-(2-Fu) | 4-Me, 5-Me | 3 | Me | —Ge(Me)₂— |
| 902 | Zr | Cl | 2-(2-Fu) | 4-Me, 5-Me | 3 | Me | —Ge(Me)₂— |
| 903 | Hf | Cl | 2-(2-Fu) | 3-Me, 5-Me | 3 | Me | —Ge(Me)₂— |
| 904 | Zr | Cl | 2-(2-Fu) | 3-Me, 5-Me | 3 | Me | —Ge(Me)₂— |
| 905 | Hf | Cl | 2-(2-Fu) | 4-Me, 5-Me | 3 | t-Bu | —Ge(Me)₂— |
| 906 | Zr | Cl | 2-(2-Fu) | 4-Me, 5-Me | 3 | t-Bu | —Ge(Me)₂— |
| 907 | Hf | Cl | 2-(2-Fu) | 3-Me, 5-Me | 3 | t-Bu | —Ge(Me)₂— |
| 908 | Zr | Cl | 2-(2-Fu) | 3-Me, 5-Me | 3 | t-Bu | —Ge(Me)₂— |
| 909 | Ti | Cl | 2-(3-Fu) | 4-Me, 5-Me | 3 | t-Bu | —Ge(Me)₂— |
| 910 | Ti | Cl | 2-(3-Fu) | 3-Me, 5-Me | 3 | Me | —Ge(Me)₂— |
| 911 | Ti | Cl | 2-[2-(3-Me—Fu)] | 4-Me, 5-Me | 3 | t-Bu | —Ge(Me)₂— |
| 912 | Ti | Cl | 2-[2-(3-Me—Fu)] | 3-Me, 5-Me | 3 | Me | —Ge(Me)₂— |
| 913 | Ti | Cl | 2-(2-Thie) | 4-Me, 5-Me | 3 | t-Bu | —Ge(Me)₂— |
| 914 | Ti | Cl | 2-(2-Thie) | 3-Me, 5-Me | 3 | Me | —Ge(Me)₂— |
| 915 | Ti | Cl | 2-(2-Py) | 4-Me, 5-Me | 3 | t-Bu | —Ge(Me)₂— |
| 916 | Ti | Cl | 2-(2-Py) | 3-Me, 5-Me | 3 | Me | —Ge(Me)₂— |
| 917 | Ti | Cl | 2-(2-BzFu) | 4-Me, 5-Me | 3 | t-Bu | —Ge(Me)₂— |
| 918 | Ti | Cl | 2-(2-BzFu) | 3-Me, 5-Me | 3 | Me | —Ge(Me)₂— |
| 919 | Ti | Cl | 2-[2-(1-Me—Pyr)] | 4-Me, 5-Me | 3 | t-Bu | —Ge(Me)₂— |
| 920 | Ti | Cl | 2-[2-(1-Me—Pyr)] | 3-Me, 5-Me | 3 | Me | —Ge(Me)₂— |

TABLE 22

| | | | CA¹: Indenyl | | | CA²: Indenyl | | | |
|---|---|---|---|---|---|---|---|---|---|
| No. | M | X | Ra | R¹ | p + m | Ra | R¹ | q + n | Y |
| 921 | Zr | Cl | 2-[2-(5-Me—Fu)] | — | 1 | 2-[2-(5-Me—Fu)] | — | 1 | —Si(Me)₂— |
| 922 | Zr | Cl | 2-[2-(4,5-Me₂—Fu)] | — | 1 | 2-[2-(4,5-Me₂—Fu)] | — | 1 | —Si(Me)₂— |
| 923 | Zr | Cl | 2-[2-(5-t-Bu—Fu)] | — | 1 | 2-[2-(5-t-Bu—Fu)] | — | 1 | —Si(Me)₂— |
| 924 | Zr | Cl | 2-[2-(5-TMS—Fu)] | — | 1 | 2-[2-(5-TMS—Fu)] | — | 1 | —Si(Me)₂— |
| 925 | Zr | Cl | 2-[2-(5-ViMe₂Si—Fu)] | — | 1 | 2-[2-(5-ViMe₂Si—Fu)] | — | 1 | —Si(Me)₂— |
| 926 | Zr | Cl | 2-[2-(5-Me—Fu)] | 4-Ph | 2 | 2-[2-(5-Me—Fu)] | 4-Ph | 2 | —Si(Me)₂— |
| 927 | Zr | Cl | 2-[2-(4,5-Me₂—Fu)] | 4-Ph | 2 | 2-[2-(4,5-Me₂—Fu)] | 4-Ph | 2 | —Si(Me)₂— |
| 928 | Zr | Cl | 2-[2-(5-t-Bu—Fu)] | 4-Ph | 2 | 2-[2-(5-t-Bu—Fu)] | 4-Ph | 2 | —Si(Me)₂— |
| 929 | Zr | Cl | 2-[2-(5-TMS—Fu)] | 4-Ph | 2 | 2-[2-(5-TMS—Fu)] | 4-Ph | 2 | —Si(Me)₂— |
| 930 | Zr | Cl | 2-[2-(5-ViMe₂Si—Fu)] | 4-Ph | 2 | 2-[2-(5-ViMe₂Si—Fu)] | 4-Ph | 2 | —Si(Me)₂— |
| 931 | Zr | Cl | 2-[2-(5-Me—Fu)] | 4-Np | 2 | 2-[2-(5-Me—Fu)] | 4-Np | 2 | —Si(Me)₂— |
| 932 | Zr | Cl | 2-[2-(4,5-Me₂—Fu)] | 4-Np | 2 | 2-[2-(4,5-Me₂—Fu)] | 4-Np | 2 | —Si(Me)₂— |
| 933 | Zr | Cl | 2-[2-(5-t-Bu—Fu)] | 4-Np | 2 | 2-[2-(5-t-Bu—Fu)] | 4-Np | 2 | —Si(Me)₂— |
| 934 | Zr | Cl | 2-[2-(5-TMS—Fu)] | 4-Np | 2 | 2-[2-(5-TMS—Fu)] | 4-Np | 2 | —Si(Me)₂— |
| 935 | Zr | Cl | 2-[2-(5-ViMe₂Si—Fu)] | 4-Np | 2 | 2-[2-(5-ViMe₂Si—Fu)] | 4-Np | 2 | —Si(Me)₂— |

TABLE 23

| | | | CA¹: Cyclopentadienyl | | | CA²: Cyclopentadienyl | | | |
|---|---|---|---|---|---|---|---|---|---|
| No. | M | X | Ra | R¹ | p + m | Ra | R¹ | q + n | Y |
| 936 | Zr | Cl | 2-[2-(5-Me—Fu)] | 3-Me, 5-Me | 3 | 2-[2-(5-Me—Fu)] | 3-Me, 5-Me | 3 | —Si(Me)$_2$— |
| 937 | Zr | Cl | 2-[2-(4,5-Me$_2$—Fu)] | 3-Me, 5-Me | 3 | 2-[2-(4,5-Me$_2$—Fu)] | 3-Me, 5-Me | 3 | —Si(Me)$_2$— |
| 938 | Zr | Cl | 2-[2-(5-t-Bu—Fu)] | 3-Me, 5-Me | 3 | 2-[2-(5-t-Bu—Fu)] | 3-Me, 5-Me | 3 | —Si(Me)$_2$— |
| 939 | Zr | Cl | 2-[2-(5-TMS—Fu)] | 3-Me, 5-Me | 3 | 2-[2-(5-TMS—Fu)] | 3-Me, 5-Me | 3 | —Si(Me)$_2$— |
| 940 | Zr | Cl | 2-[2-(5-ViMe$_2$Si—Fu)] | 3-Me, 5-Me | 3 | 2-[2-(5-ViMe$_2$Si—Fu)] | 3-Me, 5-Me | 3 | —Si(Me)$_2$— |
| 941 | Zr | Cl | 2-[2-(5-Me—Fu)] | 4-Me, 5-Me | 3 | 2-[2-(5-Me—Fu)] | 4-Me, 5-Me | 3 | —Si(Me)$_2$— |
| 942 | Zr | Cl | 2-[2-(4,5-Me$_2$—Fu)] | 4-Me, 5-Me | 3 | 2-[2-(4,5-Me$_2$—Fu)] | 4-Me, 5-Me | 3 | —Si(Me)$_2$— |
| 943 | Zr | Cl | 2-[2-(5-t-Bu—Fu)] | 4-Me, 5-Me | 3 | 2-[2-(5-t-Bu—Fu)] | 4-Me, 5-Me | 3 | —Si(Me)$_2$— |
| 944 | Zr | Cl | 2-[2-(5-TMS—Fu)] | 4-Me, 5-Me | 3 | 2-[2-(5-TMS—Fu)] | 4-Me, 5-Me | 3 | —Si(Me)$_2$— |
| 945 | Zr | Cl | 2-[2-(5-ViMe$_2$Si—Fu)] | 4-Me, 5-Me | 3 | 2-[2-(5-ViMe$_2$Si—Fu)] | 4-Me, 5-Me | 3 | —Si(Me)$_2$— |
| 946 | Zr | Cl | 2-[2-(5-Me—Fu)] | 4-Ph, 5-Me | 3 | 2-[2-(5-Me—Fu)] | 4-Ph, 5-Me | 3 | —Si(Me)$_2$— |
| 947 | Zr | Cl | 2-[2-(4,5-Me$_2$—Fu)] | 4-Ph, 5-Me | 3 | 2-[2-(4,5-Me$_2$—Fu)] | 4-Ph, 5-Me | 3 | —Si(Me)$_2$— |
| 948 | Zr | Cl | 2-[2-(5-t-Bu—Fu)] | 4-Ph, 5-Me | 3 | 2-[2-(5-t-Bu—Fu)] | 4-Ph, 5-Me | 3 | —Si(Me)$_2$— |
| 949 | Zr | Cl | 2-[2-(5-TMS—Fu)] | 4-Ph, 5-Me | 3 | 2-[2-(5-TMS—Fu)] | 4-Ph, 5-Me | 3 | —Si(Me)$_2$— |
| 950 | Zr | Cl | 2-[2-(5-ViMe$_2$Si—Fu)] | 4-Ph, 5-Me | 3 | 2-[2-(5-ViMe$_2$Si—Fu)] | 4-Ph, 5-Me | 3 | —Si(Me)$_2$— |

TABLE 24

| | | | CA¹: Benzoindenyl | | | CA²: Benzoindenyl | | | |
|---|---|---|---|---|---|---|---|---|---|
| No. | M | X | Ra | R¹ | p + m | Ra | R¹ | q + n | Y |
| 951 | Zr | Cl | 2-[2-(5-Me—Fu)] | — | 1 | 2-[2-(5-Me—Fu)] | — | 1 | —Si(Me)$_2$— |
| 952 | Zr | Cl | 2-[2-(4,5-Me$_2$—Fu)] | — | 1 | 2-[2-(4,5-Me$_2$—Fu)] | — | 1 | —Si(Me)$_2$— |
| 953 | Zr | Cl | 2-[2-(5-t-Bu—Fu)] | — | 1 | 2-[2-(5-t-Bu—Fu)] | — | 1 | —Si(Me)$_2$— |
| 954 | Zr | Cl | 2-[2-(5-TMS—Fu)] | — | 1 | 2-[2-(5-TMS—Fu)] | — | 1 | —Si(Me)$_2$— |
| 955 | Zr | Cl | 2-[2-(5-ViMe$_2$Si—Fu)] | — | 1 | 2-[2-(5-ViMe$_2$Si—Fu)] | — | 1 | —Si(Me)$_2$— |

TABLE 25

| | | | CA¹: Azulenyl | | | CA²: Azulenyl | | | |
|---|---|---|---|---|---|---|---|---|---|
| No. | M | X | Ra | R¹ | p + m | Ra | R¹ | q + n | Y |
| 956 | Zr | Cl | 2-(2-Fu) | — | 1 | 2-(2-Fu) | — | 1 | —Si(Me)$_2$— |
| 957 | Zr | Cl | 2-(2-Fu) | — | 1 | 2-(2-Fu) | — | 1 | —Si(Me)$_2$— |
| 958 | Zr | Cl | 2-[2-(5-Me—Fu)] | — | 1 | 2-[2-(5-Me—Fu)] | — | 1 | —Si(Me)$_2$— |
| 959 | Zr | Cl | 2-[2-(4,5-Me$_2$—Fu)] | — | 1 | 2-[2-(4,5-Me$_2$—Fu)] | — | 1 | —Si(Me)$_2$— |
| 960 | Zr | Cl | 2-[2-(5-t-Bu—Fu)] | — | 1 | 2-[2-(5-t-Bu—Fu)] | — | 1 | —Si(Me)$_2$— |
| 961 | Zr | Cl | 2-[2-(5-TMS—Fu)] | — | 1 | 2-[2-(5-TMS—Fu)] | — | 1 | —Si(Me)$_2$— |
| 962 | Zr | Cl | 2-[2-(5-ViMe$_2$Si—Fu)] | — | 1 | 2-[2-(5-ViMe$_2$Si—Fu)] | — | 1 | —Si(Me)$_2$— |
| 963 | Zr | Cl | 2-(2-Fu) | 4-Ph | 2 | 2-(2-Fu) | 4-Ph | 2 | —Si(Me)$_2$— |
| 964 | Zr | Cl | 2-(2-BzFu) | 4-Ph | 2 | 2-(2-BzFu) | 4-Ph | 2 | —Si(Me)$_2$— |
| 965 | Zr | Cl | 2-[2-(5-Me—Fu)] | 4-Ph | 2 | 2-[2-(5-Me—Fu)] | 4-Ph | 2 | —Si(Me)$_2$— |
| 966 | Zr | Cl | 2-[2-(4,5-Me$_2$—Fu)] | 4-Ph | 2 | 2-[2-(4,5-Me$_2$—Fu)] | 4-Ph | 2 | —Si(Me)$_2$— |
| 967 | Zr | Cl | 2-[2-(5-t-Bu—Fu)] | 4-Ph | 2 | 2-[2-(5-t-Bu—Fu)] | 4-Ph | 2 | —Si(Me)$_2$— |
| 968 | Zr | Cl | 2-[2-(5-TMS—Fu)] | 4-Ph | 2 | 2-[2-(5-TMS—Fu)] | 4-Ph | 2 | —Si(Me)$_2$— |
| 969 | Zr | Cl | 2-[2-(5-ViMe$_2$Si—Fu)] | 4-Ph | 2 | 2-[2-(5-ViMe$_2$Si—Fu)] | 4-Ph | 2 | —Si(Me)$_2$— |
| 970 | Zr | Cl | 2-(2-Fu) | 4-Np | 2 | 2-(2-Fu) | 4-Np | 2 | —Si(Me)$_2$— |
| 971 | Zr | Cl | 2-(2-BzFu) | 4-Np | 2 | 2-(2-BzFu) | 4-Np | 2 | —Si(Me)$_2$— |
| 972 | Zr | Cl | 2-[2-(5-Me—Fu)] | 4-Np | 2 | 2-[2-(5-Me—Fu)] | 4-Np | 2 | —Si(Me)$_2$— |
| 973 | Zr | Cl | 2-[2-(4,5-Me$_2$—Fu)] | 4-Np | 2 | 2-[2-(4,5-Me$_2$—Fu)] | 4-Np | 2 | —Si(Me)$_2$— |
| 974 | Zr | Cl | 2-[2-(5-t-Bu—Fu)] | 4-Np | 2 | 2-[2-(5-t-Bu—Fu)] | 4-Np | 2 | —Si(Me)$_2$— |
| 975 | Zr | Cl | 2-[2-(5-TMS—Fu)] | 4-Np | 2 | 2-[2-(5-TMS—Fu)] | 4-Np | 2 | —Si(Me)$_2$— |
| 976 | Zr | Cl | 2-[2-(5-ViMe$_2$Si—Fu)] | 4-Np | 2 | 2-[2-(5-ViMe$_2$Si—Fu)] | 4-Np | 2 | —Si(Me)$_2$— |
| 977 | Zr | Cl | 4-(2-Fu) | — | 1 | 4-(2-Fu) | — | 1 | —Si(Me)$_2$— |
| 978 | Zr | Cl | 4-(2-BzFu) | — | 1 | 4-(2-BzFu) | — | 1 | —Si(Me)$_2$— |
| 979 | Zr | Cl | 4-[2-(5-Me—Fu)] | — | 1 | 4-[2-(5-Me—Fu)] | — | 1 | —Si(Me)$_2$— |
| 980 | Zr | Cl | 4-[2-(4,5-Me$_2$—Fu)] | — | 1 | 4-[2-(4,5-Me$_2$—Fu)] | — | 1 | —Si(Me)$_2$— |
| 981 | Zr | Cl | 4-[2-(5-t-Bu—Fu)] | — | 1 | 4-[2-(5-t-Bu—Fu)] | — | 1 | —Si(Me)$_2$— |
| 982 | Zr | Cl | 4-[2-(5-TMS—Fu)] | — | 1 | 4-[2-(5-TMS—Fu)] | — | 1 | —Si(Me)$_2$— |
| 983 | Zr | Cl | 4-[2-(5-ViMe$_2$Si—Fu)] | — | 1 | 4-[2-(5-ViMe$_2$Si—Fu)] | — | 1 | —Si(Me)$_2$— |
| 984 | Zr | Cl | 4-[2-(5-ViMe$_2$Si—Fu)] | — | 1 | 4-[2-(5-ViMe$_2$Si—Fu)] | — | 1 | —Si(Me)$_2$— |
| 985 | Zr | Cl | 4-(2-Fu) | 2-Me | 2 | 4-(2-Fu) | 2-Me | 2 | —Si(Me)$_2$— |
| 986 | Zr | Cl | 4-(2-BzFu) | 2-Me | 2 | 4-(2-BzFu) | 2-Me | 2 | —Si(Me)$_2$— |

TABLE 25-continued

|  |  |  | CA¹: Azulenyl | | | CA²: Azulenyl | | | |
| --- | --- | --- | --- | --- | --- | --- | --- | --- | --- |
| No. | M | X | Ra | R¹ | p + m | Ra | R¹ | q + n | Y |
| 987 | Zr | Cl | 4-[2-(5-Me—Fu)] | 2-Me | 2 | 4-[2-(5-Me—Fu)] | 2-Me | 2 | —Si(Me)₂— |
| 988 | Zr | Cl | 4-[2-(4,5-Me₂—Fu)] | 2-Me | 2 | 4-[2-(4,5-Me₂—Fu)] | 2-Me | 2 | —Si(Me)₂— |
| 989 | Zr | Cl | 4-[2-(5-t-Bu—Fu)] | 2-Me | 2 | 4-[2-(5-t-Bu—Fu)] | 2-Me | 2 | —Si(Me)₂— |
| 990 | Zr | Cl | 4-[2-(5-TMS—Fu)] | 2-Me | 2 | 4-[2-(5-TMS—Fu)] | 2-Me | 2 | —Si(Me)₂— |
| 991 | Zr | Cl | 4-[2-(5-ViMe₂Si—Fu)] | 2-Me | 2 | 4-[2-(5-ViMe₂Si—Fu)] | 2-Me | 2 | —Si(Me)₂— |

What is claimed is:

1. A metallocene compound represented by the following formula (1)

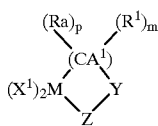

(1)

wherein $CA^1$ represents a cycloalkadienyl group selected from the group consisting of a cyclopentadienyl group, an indenyl group, a tetrahydroindenyl group, a benzoindenyl group, a fluorenyl group and an azulenyl group;

each $R^1$ represents independently a halogen atom, a hydrocarbon group of 1–20 carbons, a halogenated hydrocarbon group, a silyl group substituted by said hydrocarbon group or said halogenated hydrocarbon group, an amino group substituted by said hydrocarbon group or a monocyclic or polycyclic amino group;

each Ra represents independently a monocyclic or polycyclic heteroaromatic group containing a heteroatom selected from the group consisting of an oxygen atom, a sulfur atom and a nitrogen atom in a 5- or 6-membered ring, the heteroaromatic group being optionally substituted by $R^1$ as defined above, provided that the heteroatom in Ra is not directly attached to the 6-membered ring in the cycloalkadienyl group ($CA^1$, $CA^2$);

p is an integer of 1–8;

m is 0 or an integer of 1–8;

Z represents a linking group selected from the group consisting of $(CA^1)(R^1)_m(Ra)_p$, $(CA^2)(Ra)_q(R^1)_n$, —O—, —S—, —NR¹— and —PR¹— wherein $CA^2$ represents an unsubstituted or substituted cycloalkadienyl group; $CA^1$, m, p, Ra and $R^1$ have the same meanings as defined above, Ra may be identical with or different from said Ra on $CA^1$ and $R^1$ may be identical with or different from said $R^1$ on $CA^1$; and q and n are each independently 0 or an integer of 1–8;

Y represents a divalent linking group selected from the group consisting of —C(R²)₂—, —C₂(R²)₄—, —C₆(R²)₁₀—, —C₆(R²)₄—, —Si(R²)₂—, —Ge(R²)₂— and —Sn(R²)₂— wherein each R² represents independently a hydrogen atom, a halogen atom, a hydrocarbon group of 1–20 carbons, a halogenated hydrocarbon group or a silyl group substituted by said hydrocarbon group or said halogenated hydrocarbon group;

M represents a transition metal atom selected from the group consisting of Ti, Zr and Hf; and each $X^1$ represents independently a halogen atom, a hydrocarbon group of 1–20 carbons, a halogenated hydrocarbon group or a silyl group substituted by said hydrocarbon group or said halogenated hydrocarbon group.

2. The metallocene compound of claim 1 wherein Z represents $(CA^2)(Ra)_q(R^1)_n$, which is represented by the following formula (2)

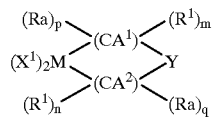

(2)

wherein $CA^1$, $CA^2$, Ra, $R^1$, p, q, m, n, Y, M and $X^1$ have each the meanings as defined above.

3. The metallocene compound of claim 1 wherein Z represents $(CA^1)(R^1)_m(Ra)_p$, which is represented by the following formula (2A)

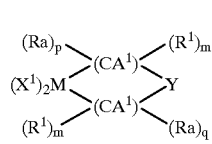

(2A)

wherein $CA^1$, Ra, $R^1$, p, m, Y, M and $X^1$ have each the meanings as defined above.

4. The metallocene compound of claim 1 wherein at least one of Ra is substituted on the 5-membered ring in the cycloalkadienyl group.

5. The metallocene compound of claim 1 wherein at least one of Ra is substituted at the 2- or 3-position of a cyclopentadienyl group, an indenyl group, a tetrahydroindenyl group, a benzoindenyl group or an azulenyl group.

6. The metallocene compound of claim 1 wherein each Ra is independently an unsubstituted heteroaromatic group and is selected from the group consisting of furyl, thienyl, pyridyl, benzofuryl, benzothienyl, quinolyl, pyrrolyl and indolyl.

7. The metallocene compound of claim 1 wherein each Ra is independently a heteroaromatic group substituted by $R^1$ as defined above and is selected from the group consisting of substituted furyl, substituted thienyl, substituted pyridyl, substituted benzofuryl, substituted benzothienyl, substituted quinolyl, substituted pyrrolyl and substituted indolyl.

8. The metallocene compound of claim 1 wherein the hydrocarbon group of 1–20 carbons as defined for $R^1$, $R^2$ and $X^1$ is an alkyl group of 1–20 carbons, an aryl group of 6–20 carbons, an aralkyl group of 7–20 carbons, an alkoxy group of 1–20 carbons, an aryloxy group of 6–20 carbons or an aralkyloxy group of 7–20 carbons.

9. The metallocene compound of claim 1 wherein each of $CA^1$ and $CA^2$ is a cyclopentadienyl group or an indenyl group;

Ra is furyl or thienyl present at the 2-position of $CA^1$ and $CA^2$ or furyl or thienyl present at the 3-position of $CA^1$ and $CA^2$;

M is Ti, Zr or Hf;

$X^1$ is a chlorine atom; and

Y is a dimethylsilylene group.

10. The metallocene compound of claim 1 wherein each of $CA^1$ and $CA^2$ is a cyclopentadienyl group;

Ra is substituted furyl present at the 2-position of $CA^1$ and $CA^2$;

M is Ti, Zr or Hf;

$X^1$ is a chlorine atom; and

Y is a dimethylsilylene group.

11. The metallocene compound of claim 1 wherein Z is $-NR^1-$, which is represented by the following formula (3a)

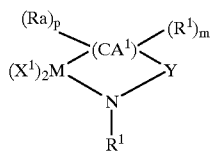  (3a)

wherein $CA^1$, Ra, $R^1$, p, m, Y, M and $X^1$ have respectively the meanings as defined above.

12. A process for the preparation of the metallocene compound of claim 1, which comprises:

(a) reacting a substituted cycloalkadiene anion represented by the following formula (4Aa)

$(Ra)_p(R^1)_m(CA^1)^-$—  (4Aa)

with a binding agent represented by the following formula (5A) at a molar ratio of 2:1, $X^2-Y-X^2$  (5A)

wherein Y has the meaning as defined above and $X^2$ represents a hydrogen atom or a halogen atom, said substituted cycloalkadiene anion being prepared by reacting a substituted cycloalkadiene represented by the following formula (4A)

$(Ra)_p(R^1)_m(CA^1)H$  (4A)

wherein $CA^1$, Ra, $R^1$, p and m have respectively the meanings as defined above, with a metal salt type base to effect an anionization; or reacting a substituted cycloalkadiene anion represented by following formula (4Aa) with any one of the compounds represented by the following formulas (5B) to (5F) at a molar ratio of 1:1, $X^2-Y-(CA^2)(R^1)_n(Ra)_q$  (5B)

$X^2-Y-(R^1)NH$  (5C)

$X^2-Y-OH$  (5D)

$X^2-Y-SH$  (5E)

$X^2-Y-(R^1)PH$  (5F)

in which Y, $CA^2$, Ra, $R^1$ and $X^2$ have respectively the meanings as defined above, to form a compound represented by the following formula (6)

$(Ra)_p(R^1)_m(CA^1)-Y-Z^1$  (6)

wherein $Z^1$ represents $(CA^1)(R^1)_m(Ra)_p$, $(CA^2)(R^1)_n(Ra)_q$, $(R^1)NH$, $-OH$, $-SH$ or $(R^1)PH$, and then (b) reacting a dianion represented by the following formula (6A)

$(Ra)_p(R^1)_m(CA^1)^- - Y-Z^- -$  (6A)

wherein each symbol has the meaning as defined above, with a transition metal compound represented by the following formula (7)

$(X^1)_2-M-(X^3)_2$  (7)

wherein M and $X^1$ have the meaning as defined above and $X^1$ represents hydrogen or a halogen atom, said dianion being prepared by reacting the compound represented by said formula (6) with a metal salt type base to anionize each of the cycloalkadienyl ring and $Z^1$.

13. The process of claim 12 wherein the substituted cycloalkadiene anion and the binding agent represented by said formula (5A) are allowed to react at a molar ratio of 2:1 in step (a) to produce the metallocene compound of claim 3.

14. The process of claim 12 wherein the substituted cycloalkadiene anion and the compound represented by said formula (5B) are allowed to react at a molar ratio of 1:1 in step (a) to produce the metallocene compound of claim 2.

15. The process of claim 12 wherein the compound represented by said formula (5B) is prepared by reacting a substituted cycloalkadiene anion represented by the following formula (4Ba)

$-(CA^2)(R^1)_n(Ra)_q$  (4Ba)

wherein each symbol has the meaning as defined above with a binding agent represented by said formula (5A) at a molar ratio of 1:1, said cycloalkadiene anion being prepared by reacting a substituted cycloalkadiene represented by the following formula (4B)

$H(CA^2)(R^1)_n(Ra)_q$  (4B)

wherein each symbol has the meaning as defined above, with a metal salt type base to effect an anionization.

16. The process of claim 12 wherein each of Ra in formulas (4A) and (5B) is independently furyl, thienyl, pyridyl, benzofuryl, benzothienyl, quinolyl, pyrrolyl having a bond at other positions than 1-position, or indolyl.

17. The process of claim 12 wherein the compound represented by formula (5A) is dialkyldichloromethane, tetraalkyl-1,2-dichloroethane, dialkyldichlorosilane, dialkyldichlorogermane or dialkyldichlorotin.

18. The process of claim 12 wherein the transition metal compound represented by formula (7) is titanium tetrachloride, dialkyl titanium dichloride, zirconium tetrachloride, dialkyl zirconium dichloride, hafnium tetrachloride or dialkyl hafnium dichloride.

19. The process of claim 12 wherein the metal salt type base is methyllithium, n-butyllithium, t-butyllithium, lithium hydride, sodium hydride or potassium hydride.

20. A catalyst for olefin polymerization comprising the metallocene compound of claim 1 and an aluminoxane.

21. A catalyst for olefin polymerization comprising the metallocene compound of claim 1, an aluminoxane and a support in the form of finely divided particles.

22. The catalyst of claim 21 wherein a reaction product of the metallocene compound and the aluminoxane is carried on the support.

23. The catalyst of claim 21 wherein the support is finely divided inorganic particles.

24. A process for the production of an olefin polymer which comprises polymerizing an olefin in the presence of the catalyst as defined in claim 20.

25. The process of claim 24 wherein the olefin is propylene or a mixed olefin of propylene and other olefins than propylene.

26. A process for the production of an olefin polymer which comprises polymerizing an olefin in the presence of the catalyst as defined in claim 21 and an organic aluminum compound.

27. The process of claim 26 wherein the olefin is propylene or a mixed olefin of propylene and other olefins than propylene.

28. The process of claim 26 wherein the organic aluminum compound is triethylaluminum or tri-iso-butylaluminum.

29. The metallocene compound of claim 1 wherein at least one of Ra is substituted on the 5-membered ring in the cycloalkadienyl group and Ra is selected from the group consisting of furyl, benzofuryl, thienyl and benzothienyl.

30. The metallocene compound of claim 1 wherein at least one of Ra is substituted on the 5-membered ring in the cycloalkadienyl group, Ra is selected from the group consisting of furyl, benzofuryl, thienyl and benzothienyl and M is Ti, Zr or Hf.

* * * * *